(12) United States Patent
Nicoli et al.

(10) Patent No.: US 7,150,996 B2
(45) Date of Patent: Dec. 19, 2006

(54) STABILITY ASSESSMENT OF DISPERSIONS AND EMULSIONS

(75) Inventors: David F. Nicoli, Goleta, CA (US); David F. Driscoll, Bridgewater, MA (US); Bruce R. Bistrian, Ipswich, MA (US)

(73) Assignee: Stable Solutions, Inc., Goleta, CA (US)

( * ) Notice: Subject to any disclaimer, the term of this patent is extended or adjusted under 35 U.S.C. 154(b) by 0 days.

(21) Appl. No.: 10/606,959

(22) Filed: Jun. 27, 2003

(65) Prior Publication Data
US 2004/0265177 A1 Dec. 30, 2004

(30) Foreign Application Priority Data
Jun. 18, 2003 (WO) .................. PCT/US03/16220

(51) Int. Cl.
*G01N 33/00* (2006.01)
(52) U.S. Cl. .................. 436/69; 436/164; 436/176; 422/73; 422/68.1; 73/53.01; 73/61.43; 73/61.48; 73/61.71; 73/64.41; 73/64.43
(58) Field of Classification Search .................. 436/69, 436/164, 176, 183; 422/73, 68.1; 73/53.01, 73/61.43, 61.44, 61.48, 61.71, 64.41, 64.43
See application file for complete search history.

(56) References Cited

U.S. PATENT DOCUMENTS

| | | | |
|---|---|---|---|
| 3,950,547 A | | 4/1976 | Lamar et al. |
| 3,956,000 A | * | 5/1976 | Kuhls et al. ............... 106/270 |
| 5,257,528 A | | 11/1993 | Degouy et al. |
| 5,319,958 A | | 6/1994 | Date et al. |
| 5,378,609 A | | 1/1995 | Kwan et al. |
| 5,835,211 A | * | 11/1998 | Wells et al. ............... 356/336 |
| 5,987,969 A | | 11/1999 | Joseph et al. |
| 6,263,725 B1 | | 7/2001 | Garver et al. |
| 6,347,884 B1 | | 2/2002 | Faure et al. |
| 6,426,377 B1 | * | 7/2002 | Gerst et al. ............... 524/166 |
| 6,794,671 B1 | * | 9/2004 | Nicoli et al. ............... 250/574 |

OTHER PUBLICATIONS

Nicoli et al. American Laboratory, vol. 33(1), Jan. 2001, pp. 32-39.*
Driscoll et al. International Journal of Pharmaceutics, vol. 240, 2002, pp. 1-10.*
Driscoll et al. International Journal of Pharmaceutics, vol. 219, 2001, pp. 21-37.*

(Continued)

*Primary Examiner*—Maureen M. Wallenhorst
(74) *Attorney, Agent, or Firm*—Buchanan Ingersoll & Rooney

(57) ABSTRACT

A method and apparatus for determining the stability of dispersions and emulsions accelerates the onset of significant particle agglomeration in a sample by stressing the sample by reducing the height of the interparticle potential energy barrier between the particles. This is achieved by adding one or more of three stress factors: changing the pH of the sample to reduce the surface charge on the particles; adding an adsorbing electrolyte so that ions of the appropriate charge are adsorbed onto the surfaces of the particles to reduce the net charge on the particles; and applying a monovalent, divalent, or trivalent salt to partially screen electrostatic repulsions between the charged particles. In a preferred embodiment, the increase in agglomeration is detected with single particle detection, such as SPOS, to generate a PSD from which a figure of merit is derived. Another embodiment detects turbidity or light scattering to generate a value X indicative of the extent of agglomeration.

77 Claims, 16 Drawing Sheets

OTHER PUBLICATIONS

Friberg, et al, "Theroy of Emulsions" (in Pharmaceutical Dosage Forms: Disperse Systems , Lieberman, et al (eds.), vol. 1), 1988, pp. 49, 63, 66, 70-71.

Breuer, "Cosmetic Emulsions" (in Encyclopedia of Emulsion Technology, Becher (ed.) vol. 2), 1985, pp. 385, 420.

Walstra, "Emulsion Stability" (in Encyclopedia of Emulsion Technology, Becher (ed.) vol. 4), 1996, pp. 1, 56-57, 119.

Euston, et al, Journal of Food Science, vol. 25, 2000, pp. 934-940.

Weiner, "Introduction" (in Pharmaceutical Dosage Forms: Disperse Systems , Lieberman, et al (ed.), vol. 1), 1988, pp. 1, 9.

Newton, Pharmacopeial Forum, vol. 25, No. 1, Jan.-Feb. 1999, pp. 7655-7661.

Yoon et al, Pharmaceutical Development and Technology, 1996, pp. 333-341.

Vadas, Stability of Pharmaceutical Products (in Remington: The Science and Practice of Pharmacy, Gennaro (ed.) 19th Edition), 1995, pp. 639, 641.

Redhead, et al, Am. J. Health-Syst Pharm., vol. 57, 2002, pp. 1174, 1176.

Mirejovsky, et al, Am. J. Health-Syst. Pharm., vol. 57, 2002, pp. 1176-1177.

Hansrani, et al, J. of Parenteral Science and Technology, vol. 37, 1983, pp. 145-150.

Kanicky, et al, Handbook of Applied Surface and Colloid Chemistry, vol. 1, 2001, pp. 251, 257.

Parfitt, G.D., ed., "Dispersion of Powders in Liquids", Elsevier, 1969, pp. 88-110.

Schneider, et al., "Pharmaceutical Suspensions and the DLVO Theory," *American Journal of Pharmaceutical Education*, 42 (Aug. ), 1978, pp. 280-289.

* cited by examiner

STABILITY ASSESSMENT OF DISPERSIONS AND EMULSIONS

BACKGROUND OF THE INVENTION

1. Field of the Invention

The present invention relates to systematic methods and apparatus for stressing dispersions and emulsions in order to accelerate the onset of particle agglomeration or droplet coalescence and thereby assess their stability and evaluate their quality and performance.

2. Description of the Related Art

There are many products and intermediate process materials in widespread commercial use that depend on fine particles dispersed or suspended in a liquid, frequently water, thus classified as 2-phase systems. These particles may be solid, as in the case of aqueous polymer suspensions. Alternatively, the "particles" may consist of droplets of a liquid normally immiscible in the suspending fluid—e.g. oil droplets, in the case of oil-in-water emulsions, or water droplets (usually containing water-soluble species), in the case of water-in-oil emulsions. As well, more complex dispersions exist as multi-phase systems, forming, for example, water-in-oil-in-water and oil-in-water-in-oil emulsions.

The particles or droplets comprising the "dispersed phase" usually possess a variety of sizes, often ranging from 0.1 micrometer (micron, or μm), or smaller, to 1 μm, or larger. The distribution of particle or droplet sizes for a particular product depends on the chemical composition of the dispersion or emulsion in question (including the dispersant(s) used in conjunction with the particles or droplets) and the physical mechanism(s) used to achieve the final product. Examples of the latter include homogenization, in the case of an oil-in-water emulsion, and emulsion polymerization, in the case of a polymer suspension. Whether the dispersed phase consists of solid particles or liquid droplets, it is convenient to refer to the distribution of particle or droplet sizes as the "particle" size distribution, or PSD, by which usage no loss of generality is implied or intended. Use of the word "particles" herein is intended to include both solid particles and liquid droplets. Likewise, it is also convenient to refer to the products as "dispersions" by which no loss of generality is implied or intended. Therefore, the use of the word "dispersion" herein is intended to include both emulsions and suspensions.

There are numerous examples of widely used products based on dispersions, suspensions or emulsions. The following list is intended to be representative of the wide range of existing applications, but it is by no means complete:

a) inorganic (e.g. silica, alumina and cerium oxide) colloidal suspensions, used for chemical mechanical planarization (CMP) processing of silicon wafers during fabrication of semiconductor devices;
b) aqueous polymer suspensions, used for paints, coatings, adhesives and sealants;
c) edible oil-in-water emulsions (containing flavor and color), used for beverages and food products, such as sauces, dressings and dietary supplements;
d) silicone-based emulsions, used for hair cleaning (shampoos) and conditioning, hand lotions and surgical scrubs, as well as sealants, flexible potting compounds and medical implants;
e) wax- and/or clay-containing aqueous emulsions, used in cosmetic preparations;
f) soybean-, safflower-, olive-, medium-chain triglyceride- and/or fish-oil based oil-in-water emulsions, used for intravenous drug delivery (e.g., anesthesia) and parenteral nutrition;
g) pigment-based suspensions, used for both conventional and ink-jet printing;
h) silane-based oil-in-water emulsions, used for water repellence applications;
i) inorganic (e.g. titanium-oxide) colloidal suspensions, used for pigmentation and sunscreens;
j) homogenized whole-milk (or fat-reduced) dispersions;
k) water-in-oil emulsions and microemulsions, used for lubricants and fuels;
l) oil-in-water emulsions, used for ultrasound contrast imaging;
m) asphalt-based oil-in-water emulsions, used for road maintenance.

The effectiveness of these and other dispersion- or emulsion-based products depends critically on their stability, both on the shelf and during use. In the context of the present invention, the term "stability" refers to the tendency of the particles comprising the dispersed phase to remain separated, without significant agglomeration or coalescence, over an extended (ideally, indefinite) period of time. The stability of a given dispersion or emulsion is typically a function not only of its chemical composition, but also of the "details" of the manufacturing process involved. The "quality," or performance, of these dispersion- or emulsion-based final products and intermediate process materials is often related to their stability—i.e. to the underlying forces that can drive them toward destabilization. The performance of these products usually correlates strongly with the PSD of the dispersion or emulsion in question. Examples of important physical properties that are affected by the PSD include viscosity, hardness, strength, conductivity (thermal and electrical), appearance, color, hue, gloss, taste and texture.

Physicochemical stability is an important outcome for the use of any commercially available suspension or dispersion. An unstable dispersion is characterized by adverse changes in the spatial distribution of the dispersed phase, such that otherwise homogeneously distributed fine particles or droplets irreversibly agglomerate or coalesce, respectively. In the case of liquid dispersions (e.g. oil-in-water or water-in-oil emulsions), the liquid droplets coalesce, resulting in ever larger, over-size "globules," ultimately leading to phase separation on a macroscopic scale. This process of particle agglomeration or droplet coalescence results in an increase not only in the mean particle/droplet size, but also in the "polydispersity," or range of particle/droplet sizes, comprising the overall PSD. The most devastating effects of agglomeration or coalescence in a commercially prepared dispersion or emulsion often occur in a size range that is approximately ½ to 1 log larger than the mean particle or droplet size. This size range where significant changes occur is referred to as the large-diameter "tail" of the PSD and is usually of the greatest interest. The relatively remote population constituting the tail of the PSD for stable dispersions generally accounts for less (often, substantially less) than 1% of the overall dispersed phase, on either a number- or volume-weighted basis. Growth in the tail of the PSD, relative to "baseline" values obtained for "good" (stable, high-quality) products, can occur at any stage—i.e. during manufacturing, storage or distribution of products, or during subsequent improper, or sub-optimal, use by the industrial or private consumer.

Failures may occur in a variety of ways that make the final manufactured product unattractive, unusable or even dangerous in the hands of the consumer. There are numerous common examples of such failures, including: poor taste associated with an unstable beverage concentrate, dairy product, food dressing or sauce; poor appearance or orifice clogging by an ink, caused by large-particle agglomerates; creation of defects (e.g. scratches) on the surface of a silicon wafer during polishing by a CMP slurry, resulting in reduced yield of semiconductor devices; poor or incomplete coating of surfaces by multi-component paints or protective finishes, due to flocculation of latex particles or wax emulsion droplets, respectively; injury to humans or animals due to intravenous administration of nutrients or drugs containing excessive amounts of coalesced oil droplets or agglomerated/fused liposomes.

The economic costs of these and other failures of dispersions or emulsions at the industrial level can be considerable, especially those associated with internal loss of either intermediate materials or end products resulting from sub-optimal production techniques. These losses can occur during new product development or in the production of established products that have wide batch-to-batch variations due to variables that are poorly understood or difficult to monitor and control. Even higher losses are incurred when inferior products escape pre-market detection protocols and must subsequently be recalled in large quantities. In addition, the industrial consumer's large-scale use of dispersions or emulsions, as either raw materials or essential components of final commercial products, entails exposure to potentially large economic losses. Finally, if the product is intended for internal human use or contains extremely volatile or combustible components, the subsequent adverse, or even lethal, consequences amplifies the health and economic risks associated with product failures.

In many cases the products or materials of interest are colloidal in nature, in which the great majority of particles (or droplets) are smaller than 1 µm, with population mean diameters typically lying in the range of 0.05–0.10 µm ("micro-emulsions"), 0.10–1.0 µm ("mini-emulsions") or 1.0–10.0 µm ("macro-emulsions"). Determination of the PSD, assuming that the measurement technique possesses adequate sensitivity and resolution, provides a valuable, and often unique, "window" on both the stability and quality (both current and prospective) of these dispersions and emulsions. Such information is potentially extremely valuable, as it can provide a quantitative, objective yardstick for judging the efficacy of a given manufacturing process, and perturbations of the latter. Ultimately, this knowledge can inform the means for optimizing the manufacturing processes used to generate the product in question.

As is evident from the list of applications above, the most widely encountered class of dispersions and emulsions are aqueous systems, in which the "continuous" phase surrounding the dispersed phase of particles or droplets consists of water. (The aqueous phase is not purely water. It invariably contains one or more species of charged, mobile ions (electrolyte) plus possibly other dissolved molecules, both charged and uncharged, together with whatever concentrations of $H^+$ and $OH^-$ ions are required to establish the pH of the dispersion medium.) Consequently, the most widely employed physical mechanism for stabilizing aqueous dispersions and emulsions is that of charge stabilization. The first comprehensive description of this mechanism was provided by Verwey and Overbeek, in their classic monograph: *Theory of Stability of Lyophobic Colloids*, Elsevier Science, Amsterdam (1948). Additions to the theory were provided by Derayaguin and Landau, and the resulting "DLVO Theory" of colloid stability (due to Derayaguin, Landau, Verwey and Overbeek) has been reviewed by numerous authors, including Hiemenz, in: *Principles of Colloid and Surface Chemistry*, Marcel Dekker, New York (1977). This theory provides a quantitative description of the competition between the two fundamental, opposing forces that exist between neighboring particles suspended in an aqueous medium—Coulombic (electrostatic) repulsions and London-van der Waals attractions.

The electrostatic interparticle repulsive force arises from the net charge (either positive or negative) residing on the surfaces of the particles. This charge may result from moieties that are covalently bonded to the surfaces—i.e. which are an intrinsic part of the particle in question—and which lose their neutrality by virtue of the dissociation of ions into the surrounding aqueous phase. The extent to which these oppositely charged "counterions" are released into the continuous phase, thereby leaving a net charge on the surface, depends on the value(s) of the individual dissociation constant(s), or pKa(s), of the "titratable," surface-bound moieties, relative to the pH of the surrounding aqueous phase. One example would be carboxylated polystyrene latex particles—i.e. latex "beads" containing COOH groups, covalently bound to their surfaces. If the pH of the aqueous phase is significantly greater than the pKa of the COOH groups (i.e. $\geq 2$ pH units above the pKa value), most of the $H^+$ ions will become dissociated from the latter, leaving negatively charged $COO^-$ groups attached to the surfaces of the particles. Conversely, as the pH of the aqueous phase approaches the pKa value (i.e. pH=pKa), only 50% of the $H^+$ ions are dissociated. At its worst, if the pH falls below the pKa value, the surface charge greatly diminishes, even approaching zero, because more $H^+$ ions are now adsorbed onto the particles, and the dispersion becomes unstable.

Alternatively, the net charge that resides on the particles to ensure their stabilization may be provided by charged molecules adsorbed onto their surfaces. A familiar example is provided by the same polystyrene latex particles (without the COOH groups), but in this case coated by molecules of an ionic surfactant, such as sodium dodecyl sulfate (SDS). The hydrophobic hydrocarbon "tails" of the SDS monomers are attracted to the surface and/or interior of the similarly hydrophobic polymeric particles, while the hydrophilic head groups are favorably disposed to lie on the surface, allowing maximal exposure to the surrounding water molecules. The majority of the $Na^+$ ions are free to diffuse in the aqueous phase, leaving a net negative charge on the surfaces of the particles, by virtue of the $SO_3^-$ groups belonging to the adsorbed SDS monomers.

As a consequence of the net charge residing on the surface of a given particle, there exists an electrical potential, $\psi_0$, on its surface, with the zero value defined at an infinite distance from the particle. The value of the electrical potential, $\psi(x)$, at a distance x from the surface of the particle decreases monotonically with increasing x, as shown schematically in FIG. 1. The distance parameter x is the normalized interparticle separation, defined as $x=(r-2a)/2a$, where r is the distance between the centers of the two particles (assumed spherical), and a is the radius of each particle (assumed uniform in size). The region immediately surrounding the surface of each particle, commonly referred to as the "Stern Layer," contains a relatively high concentration of ions having a charge opposite in sign to that of the particle surface, attracted to the latter. The concentration of these oppositely-charged ions decreases progressively with increasing distance from the particle surface. Conversely, the concentration of charged ions having the same sign as that of the macro-particle increases with increasing distance from the latter. The diffuse region that extending beyond the Stern Layer, containing both positively and negatively charged mobile ions, free to diffuse between the macro-particles, is referred to as the Gouy-Chapman Layer. The behavior of $\psi$ (x) vs x shown in FIG. 1 is not surprising, given the familiar 1/x behavior for an isolated charge, described by Coulomb's law. However, the potential typically falls significantly faster than 1/x with increasing x, due to the presence of electrolyte (i.e., salt ions) in the aqueous phase. The mobile charged ions serve to partially "screen," or neutralize, the electrostatic field existing at a distance from the charged "macro" particle. The larger the concentration of added ions of opposite charge, the greater the screening of the electrical potential at any given distance from the particle.

Conversely, mobile ions having a charge of the same sign as that on the particle will be repelled by the surface, resulting in a relative deficiency of these ions close to the surface. The concentration of charged ions of opposite sign decreases, and the concentration of those of the same sign increases, with increasing distance from the particle, such that they approach the same average concentration far from the particle, where the value of $\psi$ effectively falls to zero. The higher the concentration of added electrolyte(s), the faster the decay in $\psi$ (x) with increasing distance, x. The distance at which the potential falls to 1/e times its value on the surface, $\psi_0$, is often expressed as $1/\kappa$, where $\kappa$ is the "inverse screening length," obtained from the well-known Debye-Hückel formula. The value of $\kappa$ increases with increasing electrolyte concentration, depending on the square root of the latter (assuming monovalent ions). An increase in electrolyte concentration results in shrinkage (i.e. reduced "thickness," $1/\kappa$) of the electrical double layer.

The electrical potential extending outward from a given charged particle interacts with the charge carried by a neighboring particle, resulting in a repulsive force between the two particles. Of course, there is a corresponding electrical potential that extends out from the second particle. Therefore, the repulsive electrostatic force that exists between the two particles is often described as arising from the "intersection" of the two electrical double layers. The extent to which the two particles (or, in effect, the two electrical double layers) repel each other is accounted for analytically by the interparticle repulsive potential energy, $V_R$, as described in DLVO Theory. The behavior of $V_R$ as a function of the separation, x, between the surfaces of two charged particles is shown schematically (curve "$V_R$") in FIG. 2.

The second fundamental influence on the stability of charged particles suspended in an aqueous medium is the London-van der Waals attractive force, originating from the interaction of electrical dipole moments in two neighboring particles. The dipole moment in one particle is induced by a dipole moment momentarily created in the other due to random fluctuations in local charge density. The strength of the interaction is characterized by the Hamaker coefficient, which depends on the composition of the particles. The London-van der Waals force is effective over only relatively short distances, falling off with particle separation, x, much faster than 1/x. That is, its decay with increasing distance is much faster than the corresponding decay exhibited by the interparticle electrostatic repulsive force in the absence of significant electrolyte concentration, owing to the longer-range nature of the latter force. The behavior of the resulting attractive interparticle potential energy, $V_A$, as a function of particle separation is also shown schematically (curve "$V_A$") in FIG. 2.

The net potential energy, $V_{TOT}$, that exists between two charged particles in aqueous suspension is therefore obtained by adding together the repulsive and attractive interparticle potential energies: $V_{TOT}=V_R+V_A$. This result is also shown schematically in FIG. 2. For very small values of x—i.e. when the two particles are effectively touching—the value of $V_{TOT}$ is hugely negative, owing to the complete domination of the negative (attractive) London-van der Waals potential energy over the positive (repulsive) electrostatic energy at small separations. As the separation increases, the net potential energy rises steeply due to the diminishing influence of the short-range attractive force. Over these very small separation distances, the particles are, in effect, irreversibly agglomerated—i.e. they are trapped in the deep energy "well," representing the lowest-energy state for the 2-particle system. As the separation distance increases further, the net potential energy eventually reaches a maximum value, $V_{MAX}$, which is significantly positive provided the particles are adequately charged and the concentration of screening electrolyte is sufficiently low. Finally, $V_{TOT}$ rolls over and decreases with further increases in particle separation, x (i.e. assuming that the influence of $V_R$ is great enough to avoid the occurrence of a secondary minimum in the plot of $V_{TOT}$ vs x), eventually falling effectively to zero at large separations. The detailed behavior, or shape, of $V_{TOT}$ vs x depends on the magnitudes and shapes of the two competing potential energy functions, $V_R$ and $V_A$, that combine to form $V_{TOT}$.

The shape and magnitude of the net interparticle potential energy curve, $V_{TOT}$ vs x, shown schematically in FIG. 2, determines whether a particular charge-stabilized dispersion or emulsion will, in fact, remain stable, resisting agglomeration or coalescence over a long period of time. The peak in the $V_{TOT}$ vs x plot, having magnitude $V_{MAX}$, constitutes an interparticle energy "barrier" that protects two charged particles from approaching each other too closely (by Brownian motion, or diffusion), lest they be so strongly attracted to each other that they fall irreversibly into the deep energy well created by the strong, short-range London-van der Waals attractive force. As the particles diffuse through the aqueous phase of the suspension, they possess an average kinetic energy on the order of kT, where k is Boltzmann's constant and T the absolute temperature. The greater the height of the interparticle potential energy barrier, $V_{MAX}$, the more likely they will be repelled, failing to approach each other closely enough to allow irreversible agglomeration to occur. The higher the value of $V_{MAX}$ compared to kT, the larger the repulsive zone of "exclusion" surrounding each particle and the more infinitesimal the probability of penetration through this zone with each random attempt to do so.

It is instructive to review estimates of the influence of the interparticle potential energy barrier height on the "half-life" of a simplified "emulsion," assuming droplets of a single size, 1 µm, with an oil/water ratio of unity. These estimates were calculated by Friberg et al ("Theory of Emulsions," p. 63) in: *Pharmaceutical Dosage Forms: Disperse Systems*, H. Lieberman et al (eds.), Vol. 1, Marcel Dekker, New York (1988). The resulting droplet concentration is approximately $10^{11}$ per ml for the simplified emulsion. The half-life, $t_{1/2}$, is defined as the time needed for half of the original number of droplets in the emulsion to agglomerate, or coalesce. The rate of agglomeration, or flocculation, is proportional to the square of the number of particles per unit volume, to the radius of the particles (assumed spherical) and to their diffusion coefficient. In the absence of charge stabilization, when the particles are free to collide with each other due to random diffusion, resulting in irreversible agglomeration, the half-life is less than one second. The presence of an interparticle potential energy barrier serves to slow down the rate of agglomeration, thereby increasing the half-life. In the case $V_{MAX}$=5 kT (T=25° C.), $t_{1/2}$ increases to only 38.2 sec. A doubling of the interparticle interparticle barrier height, to $V_{MAX}$=10 kT, causes $t_{1/2}$ to increase significantly, but only to 1.55 hr—clearly inadequate for a final product that typically must have a shelf life of many weeks or months, if not years. Another doubling of the interparticle barrier height, to $V_{MAX}$=20 kT, results in a half-life of 3.91 years, approximating what is needed for many products of commercial significance. (Interestingly, an interparticle barrier height of $V_{MAX}$=50 kT implies a half-life of $4.17 \times 10^{13}$ years, surely representing a "stable" emulsion, where, for example, two days are required for the first pair of droplets (out of $10^{11}$ per ml) to coalesce.)

In principle, from DLVO theory one can estimate the height of the interparticle potential energy barrier (in units of kT) for a given charge-stabilized dispersion or emulsion, based on an independent measurement of the amount of charge residing on the particles, together with their size and the electrolyte concentration. Hence, in principle one should be able to estimate reliably the half-life of the dispersion or emulsion and achieve the desired stability by "fine-tuning" the chemical composition of the product. However, the same authors who provide the estimates of $t_{1/2}$ vs barrier height summarized above are clearly pessimistic regarding the usefulness in practice of such theoretical approaches. Friberg et al (op cit, p. 66) write: "Calculations of the relative height of the barrier with electrolyte content are interesting from a scientific point of view, but of limited value in daily formulation efforts." They (op cit, p. 70) also draw attention to the central problem associated with assessing emulsion stability—the need for large elapsed times to establish reliable conclusions. "The dilemma for the formulator of an emulsion lies in the fact that the success of a preparation can be judged only after a long time. If a shelf-life of one year is needed, it is in principle necessary to wait one year to find out whether a large number of samples still are intact." This major shortcoming is also emphasized by Breuer ("Cosmetic Emulsions," p. 420), in: *Encyclopedia of Emulsion Technology*, P. Becher (ed.), Vol. 2, Marcel Dekker, New York (1985). "Predicting long-term stability from accelerated laboratory tests still remains an elusive goal. In spite of its great commercial importance, only a small amount of fundamental research is being carried out on the problem. One of the reasons for this relatively low interest is, no doubt, due to the very long time periods that are required (e.g., 2 years of storage) for validating the results of any new predictive technique."

The lack of fundamental understanding of the variables that influence the onset of coalescence (i.e. instability) in emulsions is underscored by Walstra ("Emulsion Stability," p. 56), in: *Encyclopedia of Emulsion Technology*, P. Becher (ed.), Vol. 4, Marcel Dekker, New York (1996). "It may be clear from the discussion in this chapter that even for a relatively simple colloid like a (macroscopic) emulsion, much about its stability is insufficiently known. There are uncertainties about the colloidal interaction energy and its effect on aggregation rate. Coalescence especially needs further research, where the different variables should be studied separately. Also, partial coalescence would need more study, although the main variables have been identified and their importance has been established. Prediction of combined instabilities, which will often be encountered in practice, is far more difficult, although it has been tried in some cases." Walstra (op cit. p. 119) goes on to speak to the uncertainty that exists regarding even the significance of coalescence in emulsions. "It may be concluded that the quantitative importance of coalescence is unknown. It is probably quite variable, and may be an important cause of the differences in droplet size found with different surfactants. Since coalescence probably takes place with freshly formed drops, this notion can be reconciled with the apparent existence of a critical drop size (larger ones are broken up) depending mainly on hydrodynamic conditions and much less on the dispersed phase."

The deficiency in knowledge concerning the basic interaction phenomena in "complex" (i.e. multi-component) emulsions, such as milk protein systems, is acknowledged by Euston et al (p. 940), in: *J. Food Sci*, Vol. 65, pp. 934–940 (2000). "This work highlights two important points. First, the use of very simple systems may not be entirely appropriate when trying to predict the emulsifying characteristics of milk proteins in food systems." "Second, although the interaction of milk proteins can have a large effect on the emulsifying properties of milk protein, there are gaps in our knowledge of which interactions are important, how they occur and how they can be exploited. There is a need for a systematic study of this area to allow us to use this information to better select ingredients for a particular application."

The importance of emulsion stability, along with the apparent futility of accelerated stability testing, are underscored by Weiner (Introduction," p. 9), in: *Pharmaceutical Dosage Forms: Disperse Systems*, H. Lieberman et al (eds.), Vol. 1, Marcel Dekker, New York (1988). "Coalescence is intolerable to all groups concerned and is a function of the strength of the emulsifier film at the droplet interface, that is, the interfacial free energy barrier. The factors affecting coalescence and the factors affecting creaming are very different, and accelerated stability testing for coalescence is, at best, difficult and tricky." He continues: "With respect to predictive testing for coalescence of an emulsion or nonreversible settling of a suspension, there is little evidence that pushing the system far beyond what it will encounter in the marketplace yields any reliable information useful for shelf-life predictions. Moreover, overstressing the system creates the risk of throwing away formulations that would be perfectly acceptable under realistic conditions."

Friberg et al (op cit, pp. 70–71) conclude their pessimistic assessment with the admission that faster, reliable testing methods do not exist. "This problem would be avoided if a reliable method for accelerated testing were found; that is, if a method were available that made it possible to judge the long-term behavior from short-term changes. Unfortunately, a general method of this kind is not available. There are methods in use that accelerate the destabilization process for emulsions of specific kinds, and these are useful within their realm of application. On the other hand, the important fact that these methods may give completely erroneous results when applied outside their established realm cannot be overemphasized."

From the references cited above, it is clear that the central, unresolved problem in this field has been the prohibitively long time needed to establish whether, and to what extent, a given emulsion or dispersion is stable. Therefore, efforts have been made to accelerate the process of stability testing. Past attempts have, for the most part, centered around three means of accelerating the onset of instability of potentially problematic dispersions: 1) increasing (often substantially) the temperature; 2) inducing strong shear forces by mechanical means; and 3) speeding up the rate of sedimentation or flotation of large particles/droplets, by centrifuging the sample. Notwithstanding the usefulness of these various methods, for the most part they fail to yield unambiguous and/or consistently reliable quantitative information regarding the extent to which a given emulsion or dispersion is stable, or how it compares in quality to benchmark products of known performance.

Regarding the rationale for "thermal stress," DLVO theory teaches that the stability of a dispersion or emulsion worsens with a decrease in the interparticle potential energy barrier height, $V_{MAX}$, relative to a fixed value of kT. Hence, an increase in temperature for a fixed value of $V_{MAX}$ (i.e. an otherwise constant dispersion) should produce the same result—diminished stability. The extent to which the dispersion reveals symptoms of instability (e.g. the onset of phase separation in an oil-in-water emulsion) is therefore correlated with increases in temperature. The effect of temperature on the rates of chemical reactions (i.e. the Arrhenius equation), and hence on the stability of dispersions, notably drug formulations, is reviewed by Newton ("The Role of Temperature in the Life of a Pharmaceutical Preparation") in: *Pharmacopeial Forum*, Vol. 25, #1, pp. 7655–7661 (January–February 1999), with corrections in Vol. 25, #4, p. 8627 (July–August 1999).

The use of elevated temperature to simulate the effects of aging on an emulsion-based reagent for performing assays of lipase is described by Kwan et al, in U.S. Pat. No. 5,378,609 (1995). The optical absorbance of a stable emulsion formulation indicated essentially unchanged composition and activity following thermal stressing at 57° C. for 12 days, equivalent to normal storage at 4° C. for four years. This behavior was in sharp contrast to what was observed for an unstable control sample, which began to degrade within seven days of storage at 4° C. and which showed immediate increased absorbance at 57° C., indicating the onset of precipitation.

Faure et al, in U.S. Pat. No. 6,347,884 B1 (2002), describe a method for determining the temperature stability of water-in-hydrocarbon emulsions with respect to phase separation, including crystallization of paraffins in gas oils at certain temperatures. The onset of phase separation is detected by monitoring the weight variations of a gravimetric sensor that is partially immersed in the water-oil mixture, used to enhance combustion efficiency.

Garver et al, in U.S. Pat. No. 6,263,725 B1 (2001), describe the use of an on-line sensor based on UV-visible light absorption and/or scattering to detect and identify colloidal substances, such as pitch or wood resin in pulp or paper process water. The difference or ratio of light attenuation or scattering measurements of a colloidal mixture performed at two or more temperatures provides a measure of the stability of the dispersion with respect to temperature. The observed differences in thermal stability for different samples provide a means for distinguishing different components of colloid-based fluids.

The method of raising the temperature to assess emulsion stability was also utilized by Yoon et al ("Interfacial properties as stability predictors of lecithin-stabilized perfluorocarbon emulsions"), in: *Pharm Dev Tech*, Vol 1, pp. 333–41 (1996). The oil-in-water emulsion used Pluronic F68 (a nonionic surfactant) to help stabilize the oil-droplet phase (by the mechanism of steric hindrance) and egg lecithin to provide additional charge-mediated stabilization. Thermal kinetic accelerated stability testing was conducted at 5, 20, 37 and 60° C., using multiple emulsion formulations and several means of particle size analysis to detect changes in the PSD of the droplets over a period of two months. In general, the number of days required to achieve the maximum measured mean diameter, "$D_{MAX}$," decreased with increasing temperature, as expected. However, there was a significant variation observed among the various emulsion formulations for some of the temperature values employed. The "Days to $D_{MAX}$" period varied from 3 to 14 days at 60° C.; the period was uniformly 14 days at 37° C.; the period varied from 14 to 21 days at 20° C.; and the period was mostly 21 days at 5° C. The addition of cholesterol (i.e. added charged coating of the oil droplets) was found to improve the stability of the emulsion to thermal stress—i.e. it lengthened the period of time before noticeable changes in the PSD were detected. The significant variability observed in "Days to $D_{MAX}$" for most of the temperatures employed only underscores the limitation associated with the use of temperature stress as a means of quantitatively evaluating the stability of typical multi-component emulsions.

Vadas ("Stability of Pharmaceutical Products," p. 641) highlights the pitfalls associated with the use of elevated temperatures to accelerate stability assessment, in: *Remington: The Science and Practice of Pharmacy*, Gennaro (ed.), Vol. 1, Mack Publishing, Easton, Pa. (1995). "Two simple tests are used to screen emulsion formulations. First, the stability of an emulsion can be determined by heating it to 50–70° C., and its gross physical stability observed visually or checked by turbidimetric measurements. Usually the emulsion that is most stable to heat is most stable at room temperature. However, this may not be true because an emulsion at 60° C. may not be the same at room temperature. Second, the stability of the emulsion can be estimated by the "coalescence time" test. Although this is a rough quantitative test, it is useful for detecting gross differences in emulsion stability at room temperature."

The first point made above by Vadas is that this seemingly straightforward approach of increasing substantially the temperature of an emulsion may, in practice, be seriously flawed. The typical increases in temperature that may be required to assess the stability of the emulsion using the principles of DLVO theory may be large enough to cause the emulsion itself to change. Depending on the complexity of its phase diagram, these increases in temperature may achieve the highly undesirable result of "converting" the emulsion or dispersion into a significantly "different" system, physically speaking, including having a significantly different PSD. This possible behavior is in sharp contrast to the desired goal of using the variable of temperature as a means only of perturbing the effectiveness of the net repulsive interaction between neighboring charged particles or droplets, while the character of the emulsion or dispersion is presumed to remain essentially unchanged.

The second approach that has been utilized for assessing emulsion stability is application of mechanical stress—e.g. "shaking" it in one form or another—in order to subject the dispersion or suspension to shear forces. The presumption is that application of moderate-to-strong shear forces will cause less stable emulsions to exhibit coalescence faster than more stable ones. For example, Degouy et al, in U.S. Pat. No. 5,257,528 (1993), describe a device for studying, on an accelerated basis the aging of a fluid circulating in a closed circuit—e.g., for testing the stability of muds used in oil drilling. The fluid is subjected to predetermined, elevated temperature and pressure and is circulated at a much faster rate than normally utilized, thus resulting in much higher shear forces. The fluid thereby undergoes accelerated aging, requiring only a relatively short time to reveal its rheological properties and, ultimately, its stability.

However, in practice, once again, this seemingly "straightforward" approach involving the application of mechanical stress for accelerated stability testing has proven to be fraught with uncertainties and difficulties. The limitations inherent in this approach can be appreciated by reviewing the communications between two pharmaceutical manufacturers of intravenous emulsions, in the form of Letters to the Editor ("Pharmaceutical and antimicrobial differences between propofol emulsion products") published recently in *Am J Health-Syst Pharm*, Vol. 57, pp. 1174–76, 1176–77 (2000).

In the first letter, Redhead et al summarize the results obtained from accelerated physical stability testing (vigorous shaking) of their brand-name product, a phospholipid-stabilized 10% soybean oil-in-water emulsion (pH 6–9) containing 1% propofol, used for intravenous anesthesia and sedation purposes. A "wrist-action" shaker operating at 270 shakes/min for up to 16 hours was used to provide prolonged mechanical stress to the emulsion. Several particle size analysis techniques were used to assess changes in the PSD as a function of the duration of shaking. Results were compared with those obtained for a generic "equivalent" product (pH 4.5–6.4). Within two hours of shaking, the generic product exhibited large changes in the volume percentage of large-diameter (>2 μm) oil droplets, compared to no measurable changes after 16 hours for the brand-name product. The relatively poor stability of the generic product was attributed to its low pH, expected to reduce the negative surface charge (and corresponding zeta potential) of the phospholipid-stabilized oil droplets.

In their response to the Letter by Redhead et al, Mirejovsky et al dispute the validity of shake tests for providing a reliable measure of emulsion stability. They cite inconsistencies in the methods of mechanical agitation (i.e. oscillatory movement utilized in earlier studies referenced by Redhead et al, versus up-and-down movement associated with the wrist-action shaker actually used). They further cite the earlier work of Hansrani et al, in *J. Parenter. Sci. Technol.*, Vol 37, pp. 145–150 (1983), acknowledging that oscillatory movement may cause emulsions to separate, but that if a formulation withstands sterilization, it will likely resist oscillation-induced disruption. Mirejovsky et al conclude: "These examples illustrate that a correlation between excessive shaking and the stability of an emulsion in real situations has never been established."

Notwithstanding the potential difficulties, cited above, associated with the application of mechanical stress for accelerating the assessment of dispersion and emulsion stability, methods and equipment have been developed for implementing such testing procedures. An apparatus and method for evaluating the phase change of an emulsion is described by Date et al, in U.S. Pat. No. 5,319,958 (1994). A portion of the emulsion is applied to a sliding surface, and another surface is pushed against the latter during testing. A sensor means measures the force imparted to the pushing surface in the sliding direction. Changes in the measured force permit evaluation of the phase change of the emulsion. A method and apparatus for characterizing the dynamic stability (i.e. during flow) of emulsions is described by Joseph et al, in U.S. Pat. No. 5,987,969 (1999). An emulsion is fed through a gap defined between a stationary surface and a moving surface within a test vessel. The dynamic stability of the emulsion can thereby be characterized, based upon cycles of flow through the test vessel.

Lamar, III et al, in U.S. Pat. No. 3,950,547 (1976), describes methods for determining the stability of dietary emulsions following their preparation. The easiest, least sophisticated of these methods consists simply of "watching and waiting." The percent volumes of separated fat, water-rich phase and oil-rich phase that have formed at various intervals of elapsed time, from one-half hour to 40 hours later are determined visually using a transparent, graduated vessel. Other methods involve the application of both thermal and mechanical stress to the emulsion. Thermal stability is determined by heating samples at 71° C. for two hours, followed by visual evaluation for signs of phase separation. Shear stability is determined by subjecting samples to high-speed (3200 r.p.m.) agitation in a Waring blender, again followed by visual inspection.

Centrifugation was listed earlier as a third means of testing emulsion stability on an accelerated basis. Vadas (op cit, p. 641) reviews the usefulness of centrifugation for assessing emulsion stability, where the droplets are assumed to have a lower density than that of the surrounding water phase. "The ultracentrifuge also is used to determine emulsion stability. When the amount of separated oil is plotted against the time of centrifugation, a plateau curve is obtained. A linear graph results when the oil flotation (creaming) rate is plotted vs the square of the number of centrifuge revolutions per minute. The flotation rate is represented by the slope of the line resulting when the log distance of emulsion-water boundary from the rotor center is plotted against time for each revolution per minute." The progression of the emulsion-water boundary with elapsed time is typically followed by measuring the radial distribution of turbidity as a function of time, for various rotational speeds. The use of a centrifuge serves to decrease greatly the time needed to achieve significant oil flotation (creaming), compared to the long times required using a simple (gravity) sedimentation/flotation device, also based on turbidity. However, the centrifugal approach has at least one serious potential shortcoming. The act of progressive sedimentation or flotation of the suspended droplets causes large changes in the local concentration of these droplets. That is, a large oil-concentration gradient develops over time in the emulsion. Depending on the detailed nature of the phase diagram, it is entirely possible, if not probable, that the emulsion will be significantly changed in character, as opposed to being gently perturbed. This potential problem mirrors that which can occur due to excessive elevation of temperature, alluded to above by Vadas (op cit, p. 641).

Finally, Kanicky et al. ("Surface Chemistry in the Petroleum Industry," p. 257) demonstrates the ongoing gaps in knowledge in emulsion technology, in: *Handbook of Applied Surface and Colloid Chemistry*, Holberg (ed.), Vol. 1, John Wiley and Sons, Ltd, West Sussex, UK (2002). Kanicky et al (op cit, p. 257) write: "It is clearly evident that emulsions are very complicated systems. Progress has been made on theoretical studies attempting to clarify the complexities of these systems. However, the majority of predictions of the type and stability of emulsions derives more from empirical observation than from theory. Emulsion formulation is still considered to be an art rather than a scientific method in many circles of industry." Recent assessments by investigators, working in different fields of emulsion technology, draw attention to the shortcomings that exist in dispersion science. For example, Euston et al (op cit, 2000), Mirejovsky et al (op cit, 2000) and Kanicky et al (op cit, 2002) confirm that relatively little progress has been made in applying theoretical models to observed emulsion stability.

These models include those discussed by Breuer (op cit, 1985), Friberg et al (op cit, 1988) and Walstra (op cit, 1996), applied to actual emulsions.

SUMMARY OF THE INVENTION

It is the object of the invention to provide more reliable and quantitative methods and apparatus for determining the stability of dispersions and emulsions.

It is a further object to provide such methods and apparatus which significantly accelerate the onset of instability in dispersions and emulsions when compared with the techniques taught and practiced in the prior art as discussed above.

To these ends, the present invention teaches applying physicochemical stress to the sample dispersion or emulsion in a way which accelerates the onset of significant particle agglomeration and which in particular, stresses the sample dispersion or emulsion by reducing the height of the interparticle energy barrier between particles of the dispersion or emulsion, which barrier inhibits neighboring particles from approaching each other closely enough to permit irreversible agglomeration due to strong, short-range attractive forces.

The stability of the dispersion or emulsion is then determined in a preferred embodiment of the invention by detecting increases in the particle agglomeration with a high sensitivity, quantitative detector, such as a single-particle optical sensor (SPOS). Such a sensitive, quantitative detector produces a particle size distribution (PSD) showing the concentration of particles as a function of size over a range of normal particle sizes and a tail of large-diameter outlier particles larger than the normal sizes, the outlier particles being indicative of the agglomeration of particles of the dispersion or emulsion.

One of three different types of stress factors for stressing the sample may be used. First, the stress factor reduces the charge on the surfaces of the particles by changing the pH of the sample. When the particles have a net negative charge, the stress factor is an acid or buffered acid added to the sample to reduce the pH of the sample. When the particles have a net positive charge, the stress factor is a base or buffered base added to the sample to raise the pH of the sample.

Second, the stress factor reduces the net charge on the surfaces of the particles by adding adsorbing electrolyte to the sample, permitting dissociated ions of the appropriate charge to adsorb onto the surfaces of the particles. When the particles have a net negative charge, positively charged ions dissociated from the added electrolyte bind to the surfaces of the particles and reduce the net charge on the particles and thereby reduce the height of the interparticle potential energy barrier. When the particles have a net negative charge, negatively charged ions dissociated from the added electrolyte bind to the surfaces of the particles, similarly reducing the net charge on the particles and reducing the height of the interparticle potential energy barrier.

Third, the stress factor partially screens electrostatic repulsions between the charged particles, thus promoting particle agglomeration. The stress factor is applied as a simple monovalent salt, such as sodium chloride, or as a divalent or trivalent salt.

In the preferred embodiment of detecting increases in particle agglomeration, after the measurement of the PSD of a sample, or of a batch derived from the sample, the percentage of the dispersed phase (PDP) is calculated from each measured PSD. The rate of change of the PDP with elapsed time for each of the stress factor levels is then computed. A figure of merit (FM) is then derived from the rate of change of the PDP with elapsed time for a given stress factor level. It is to be observed that stable dispersions or emulsions will have relatively small values of FM, while inferior, less stable dispersions and emulsions will have relatively large values of FM.

The value of FM of a sample may be obtained in other ways. The increase of the PDP per unit change in the stress factor level for a given value of elapsed time may be computed, and a value of FM is then derived from the increase in the PDP per unit change in the stress factor level for a given value of elapsed time, provided that the elapsed time is sufficiently long to permit accelerated instability and significant particle agglomeration to be established. The larger the value of FM for a given value of elapsed time and level of applied stress factor, the less stable the sample.

The value of FM of a sample may also be derived from the rate of change of PDP with elapsed time for a given stress factor level combined with the increase in PDP per unit change in the stress factor level for a given value of elapsed time.

In one aspect of the invention, the stress factor is applied in successive increments at spaced time intervals, resulting in successively increasing stress factor levels, and the step of detecting increases in particle agglomeration is repeated after each stress factor increment.

In another aspect of the invention, the sample is divided into several batches. A different level of the stress factor is applied to each corresponding batch. The increase in particle agglomeration is measured for each batch, and this measurement is preferably a measurement of the PSD of each batch after the passage of time $\Delta t$. The increase in particle agglomeration may also be detected in each of the batches immediately after the application of the stress factor to each of the batches. A control batch may be provided to which no stress factor is applied, and the increase, if any, in particle agglomeration in the control batch is detected after the passage of time $\Delta t$.

Alternatively, the high sensitivity detector comprises a detector, which does not respond to single particles of the sample. The detector senses a value X responsive to particles passing through a given region for a given time interval. The value X may be a measure of the attenuation of light in response to the turbidity of the sample dispersion or emulsion or a measure of the intensity of light scattered over a given range of angles from the particles of the sample dispersion or emulsion.

The apparatus of the invention is used to perform the steps of the method of the invention. The apparatus uses a dispensing pump to feed a sample of the dispersion or emulsion under test to a test container or, as separate batches, to several test containers. Another dispensing pump feeds a stress factor, as discussed above, to the sample in a test container. The sample from the test container is then fed through a detector, which detects the increase in particle agglomeration. In one embodiment the detector is a single-particle analyzer, such as a SPOS, which provides a PSD, which may include a tail of large-diameter outlier particles indicative of the extent of the agglomeration of the particles. The apparatus facilitates the calculation of the PDP, the rate of change of the PDP, and the increase in PDP per unit change in the stress factor level, and derives values of FMs from these data. In a second embodiment, the detector senses a value X responsive to particles of the sample dispersion or emulsion passing through a given region for a given time interval. The value X may be a measure of the attenuation of light in response to the turbidity of the sample dispersion or emulsion; or X may be a measure of the intensity of light scattered over a given range of angles from particles of the sample dispersion or emulsion.

The apparatus of the invention includes a computer controller/processor, suitably programmed to control the pumps, the flow of the sample and stress factors to the test container or containers, the operation and timing of the sensors, and the computations and manipulation of the data in accordance with the methods of the invention.

BRIEF DESCRIPTION OF THE DRAWINGS

These and other objects, features and advantages of the invention will be more fully appreciated with reference to the accompanying Figures, in which.

DETAILED DESCRIPTION OF THE INVENTION

The present invention is motivated by the universally recognized need for more reliable and quantitative methods for determining the stability of emulsions and dispersions. More specifically, this invention is directed to novel methods of stability testing which provide significantly accelerated results relative to techniques that are in current use, such as those alluded to in the references cited above. The new methods to be described address the long-standing need for significant improvements in stability testing of dispersions, not only with respect to faster determination, but also with respect to improved reproducibility and predictive capability.

Figure 2:
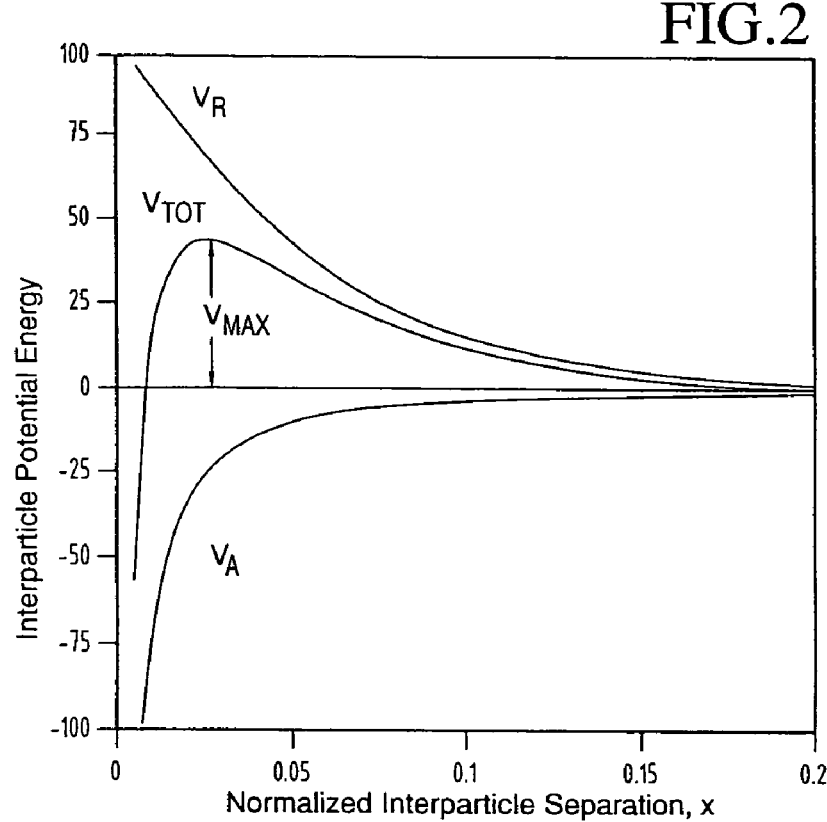
FIG. 2 shows schematically the net interparticle potential energy, $V_{TOT}$, having a barrier height $V_{MAX}$, resulting from the attractive potential energy, $V_A$, and repulsive potential energy, $V_R$.

From the preceding discussion, it is evident that the stability of a dispersion—i.e. resistance against significant agglomeration of particles or coalescence of droplets comprising the dispersed phase—is intimately connected to the height, $V_{MAX}$, of the interparticle potential energy barrier, shown schematically in FIG. 2. For a given temperature, T, and corresponding thermal energy kT, the higher the barrier, the greater the stability of charge-stabilized dispersions, and therefore the longer the time following manufacture before irreversible agglomeration of particles or coalescence of droplets (eventually leading to phase separation) becomes significant.

As reviewed earlier, there are two fundamental mechanisms which can be employed to increase the value of $V_{MAX}$, assuming substantially fixed particle composition and concentration, and therefore substantially fixed interparticle attractive potential energy, $V_A$, as a function of separation, x. First, the average amount of electric charge attached to the surfaces of the particles/droplets can be increased, thereby increasing the average electrical potential, $\psi_0$, on their surfaces. This action has the effect of "lifting," in effect, the entire curve of interparticle repulsive potential energy, $V_R$ vs x, shown schematically in FIG. 2 (i.e. increasing the value of $V_R$ for all values of x). As will be seen below, there are two basic ways of increasing the charge on the particles or droplets. Second, the concentration of mobile ions in the aqueous phase can be reduced, thereby reducing the screening of the electrical field extending out from each particle or droplet. This action has the effect of "stretching" out to longer distances the curve of $V_R$ vs x, thus permitting a greater intersection, or overlap, of the repulsive electrical double layers associated with the particles or droplets. Either of these two actions has the effect of increasing the height of the net interparticle potential energy barrier, thereby preventing to a greater degree neighboring particles from approaching each other closely enough to permit irreversible agglomeration due to strong, short-range attractive forces.

Therefore, in practice one can apply the principles of charge stabilization in "reverse," in order to implement methods for accelerated, quantitative stability testing of dispersions, which is the subject of this invention. Below are described means for systematically reducing the height of the interparticle potential energy barrier, $V_{MAX}$, in dispersions of interest, so as to accelerate the onset of significant particle/droplet agglomeration, and, in the process, obtain a quantitative assessment of the stability/quality of these dispersions. As indicated by the numerical examples calculated by Friberg et al (op cit, p. 63), discussed above, dramatic reductions in the half-life of an emulsion or dispersion can be achieved, depending on the extent to which the energy barrier height is reduced (i.e., in relation to the value of kT). This strong dependence of sample stability on barrier height provides the means whereby methods of accelerated stability testing can be designed which are effective in distinguishing a relatively stable "example" (i.e. sample) from another example which is substantially less stable.

Frequently, one is confronted with two examples of a dispersion that may differ substantially in stability. The conundrum that typically exists is that reliable, unambiguous determination of which example is the more stable of the two, and by how much, may require a long period of time (typically weeks, months or years, depending on the product). This limitation is emphasized by Friberg et al (op cit, p. 70) and Breuer (op cit, p. 420), cited earlier. The limiting factor is that the least stable of the samples must reach a level of instability—i.e. extent of agglomeration or coalescence—that can be reliably measured and quantified. Fortunately, the physical mechanism responsible for imparting stability to each sample, such as it is, can be exploited so as to reveal the differences between them, in a greatly accelerated fashion. The reason why one example is "better" than the other with respect to stability can ultimately be reduced to the simple fact that the energy barrier height for it is larger than the barrier height for the "inferior" sample.

The rationale behind the novel methods to be discussed is to lower the interparticle energy barrier height, $V_{MAX}$ (i.e., for a given temperature) by one or more predetermined increments, specific to the dispersion in question, using one or more "stress factors" (discussed below), again specific to the product being investigated. As a result, the "inferior" dispersion is quickly "pushed" to the onset of measurable instability, reaching this point much faster than would otherwise occur in more stable dispersions in the absence of the applied stress factor. Optionally, application of additional increments of stress to the dispersion permits the dynamics of its instability to be probed quantitatively and in detail.

Figure 3:
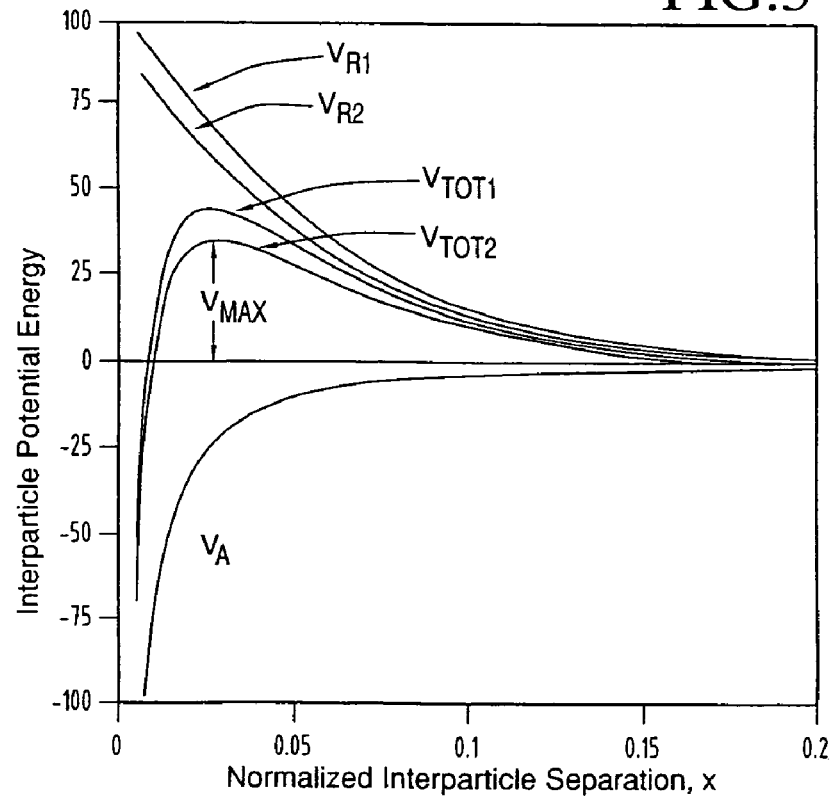
FIG. 3 shows schematically the progressive increase in the height, $V_{MAX}$, of the interparticle potential energy barrier (curves $V_{TOT1}$ and $V_{TOT2}$) as a result of the increase in strength of the repulsive potential energy, $V_R$ (curves $V_{R1}$ and $V_{R2}$), assuming a fixed attractive potential energy, $V_A$.

The effect of successive incremental reductions in the interparticle repulsive potential energy on the height of the resulting energy barrier is shown schematically in FIG. 3. The "starting" repulsive energy, $V_R$, for the dispersion, before the application of a stress factor, is indicated by curve $V_{R1}$ in FIG. 3. The resulting net (total) interparticle potential energy is also shown, by curve $V_{TOT1}$. (The attractive potential energy, $V_A$, also shown in FIG. 3, is assumed to be constant, unaffected by the stress factor.) The application of increasing amounts of the stress factor results in a progressive reduction in the interparticle repulsive energy, $V_R$—e.g., from curve $V_{R1}$ to curve $V_{R2}$. As a result, there is a corresponding reduction in the height, $V_{MAX}$, of the interparticle potential energy barrier—from curve $V_{TOT1}$ to curve $V_{TOT2}$. Consequently, the, dispersion becomes progressively less stable, resulting in accelerated particle agglomeration.

Figure 4A:
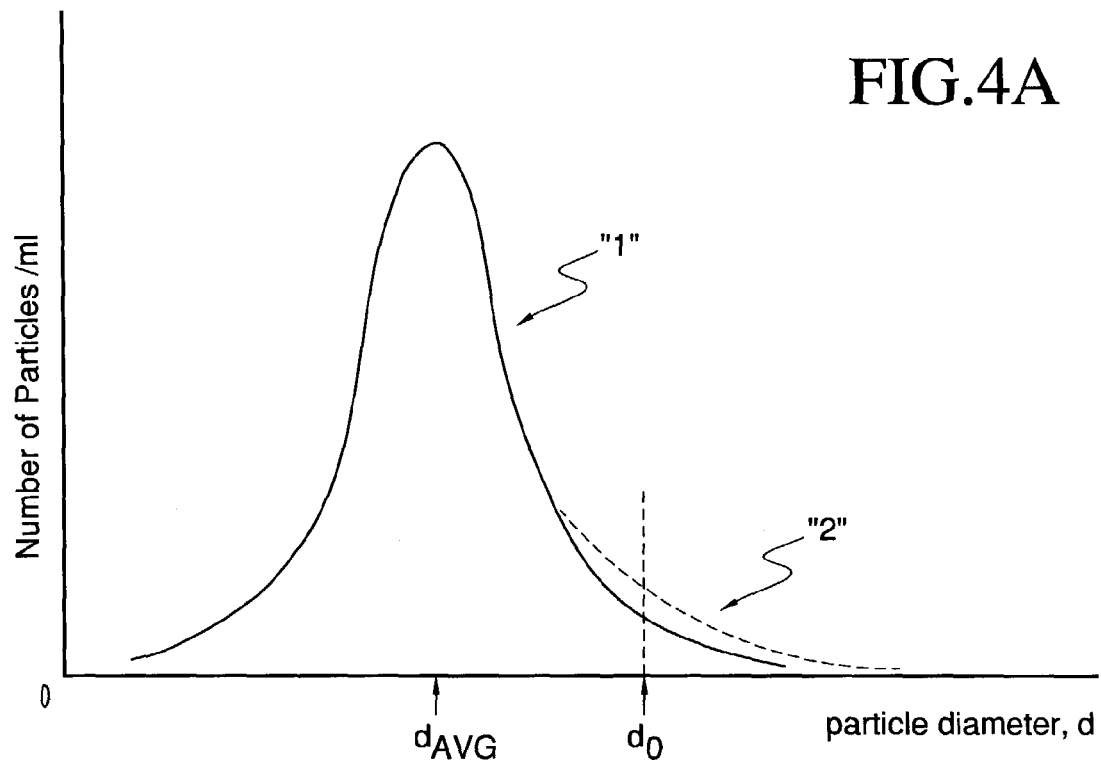
FIG. 4A shows schematically the particle size distribution (PSD—# particles vs diameter, d) for a stable dispersion or emulsion (solid curve—"1"), and after the onset of significant instability (dashed curve—"2"), leading to particle agglomeration or droplet coalescence.

There is a second ingredient that is required for implementation of the new methods for accelerated stability testing. This is a sensitive, quantitative means for determining the extent to which the dispersion has become less stable by virtue of application of one or more stress factors. The parameter of particle size distribution (PSD), applying both to solid particles and liquid droplets, in principle provides a reliable and straightforward indication of the extent of particle agglomeration or droplet coalescence, respectively, which has occurred in the dispersion. (The term agglomeration is sometimes used herein to indicate coalescence, as well, in the case of liquid-in-liquid emulsions.) As indicated previously, the presence of particle/droplet agglomeration is the physical manifestation of the extent of instability of the dispersion; the greater the progression toward instability, the larger the extent of agglomeration. Therefore, a measurement of the PSD (including the "globule size distribution, or GSD) constitutes the most direct way of probing the stability of an emulsion or dispersion. FIG. 4A (solid curve, 1) shows a simplified (stylized) representation of the PSD for a relatively stable dispersion or emulsion, before significant particle agglomeration has taken place. FIG. 4A (dashed curve, 2) also shows a simplified picture of the PSD for the same sample after an elapsed period of time, when a measurable amount of agglomeration has occurred—e.g. after application of one or more particular stress factors to the dispersion. If the increase in agglomeration is modest, indicative of only a small progression toward instability, the change in the PSD should, to first approximation, be relatively small growth in the "tail" of large-diameter "outlier" particles.

The technique that is employed to determine the PSD must, in practice, be sensitive enough to detect quantitatively relatively small changes in the state of agglomeration of the dispersion in question. If the technique utilized lacks sufficient sensitivity to changes in the PSD associated with relatively small increases in particle/droplet agglomeration, then the rationale underlying the new methods of this invention may be compromised. In that case, the stress applied to the dispersion would need to be larger than desired in order to produce enough agglomeration to permit detection of a meaningful change in the PSD after a relatively short time. That is, a relatively large reduction in $V_{MAX}$—no longer the assumed small perturbation of the dispersion—would be needed, resulting in two potential problems. First, such a presumably large stress may cause both the "good" and "interior" examples of a dispersion to become so unstable that they both exhibit substantially similar, large extents of agglomeration in a short period of time. It may then be difficult, if not impossible, to quantify the differences in quality, vis-à-vis stability, of the two samples. Second, and potentially more worrisome, application of a large stress to the dispersion runs the risk of altering the fundamental character of the emulsion or dispersion, so that the two examples to be compared no longer closely resemble the samples at the start, relative to physicochemical structure or properties.

The technique of single-particle optical sensing, or SPOS, is ideally suited to the task of detecting and quantifying growth in the "tail" of the PSD associated with small increases in the population of over-size particle agglomerates or coalesced globules that occurs in the early stages of accelerated dispersion destabilization. The SPOS technique (also referred to as optical particle counting, or OPC) is attractive largely because it is so sensitive: i.e., it responds to individual particles in the size range of interest. The physical principle of either light extinction (LE) or light scattering (LS) can be employed to detect and size particles suspended in fluid as they pass individually through a well-defined optical sensing zone (OSZ). In the LE method, the resulting signal consists of negative-going pulses, of height $\Delta V_{LE}$, superimposed on a relatively large background voltage level, $V_0$. In the LS method, the signal consists of positive-going pulses, of height $\Delta V_{LS}$, ideally superimposed on a zero background voltage level. In either case, assuming a properly designed sensor, the pulse height increases monotonically with the particle diameter, d. Particles or droplets can therefore be sized from their measured pulse heights using a predetermined "calibration curve," $\Delta V_{LE}$ vs d or $\Delta V_{LS}$ vs d, obtained using "standard" particles (typically polystyrene latex) of several known, uniform diameters.

The LE-type SPOS technique typically provides the largest particle size range, depending on the optical design of the sensor. A representative LE-type sensor, the Model LE400-1.3 (Particle Sizing Systems, Santa Barbara, Calif.), provides a nominal size range of 1.3 to 400 μm and is ideally suited for measuring the large-diameter tails of both mini- and macro-emulsions. (The results discussed below were obtained using this sensor.) The lower size detection threshold can be reduced significantly by utilizing the LS method, owing to the absence of the large background voltage, $V_0$, and the ability to increase the pulse height for a given particle size by increasing the intensity of the light source. However, in practice an LS-type sensor lacks the upper size limit that is readily available using the LE method. If desired, the LE and LS methods can be combined in a hybrid sensor design, thus producing a "summation" response, termed "LE+LS," as described by Wells et al, in U.S. Pat. No. 5,835,211 (1998). This approach yields both a lower size limit and a wide dynamic size range (e.g. 0.5 to 400 μm), features that, together, are unavailable using either the LE ort LS principle alone.

Differences in the optical properties—notably, the refractive index—of the particles or droplets being investigated, relative to the properties of the standard particles used to generate the calibration curve, necessarily result in discrepancies between the "apparent" PSD, obtained using the SPOS technique, and the actual, or true, PSD. In the case of the LS method, the discrepancies can be quite large, requiring theoretical correction, if the refractive index "contrast" of the particles with respect to the surrounding liquid is significantly different from the contrast of the standard particles. Fortunately, with the LE method the magnitude of the response is much less dependent on the contrast of the particles for most samples of interest. Hence, the measured PSD obtained by SPOS-LE usually serves as a reliable proxy for the true PSD of the sample. Growth in the measured "tail" of the latter therefore usually provides a good description, both qualitatively and quantitatively, of the actual increase in the population of over-size agglomerates or coalesced droplets/globules resulting from stress-induced instability of the dispersion.

There are several additional features or requirements associated with the SPOS technique that merit brief discussion. First, most dispersions or emulsions of interest are very concentrated, with the dispersed phase often accounting for at least 1%, and sometimes as much as 40% or 50%, of the entire sample on a volume-weighted (v/v) basis. Hence, substantial dilution of the starting sample is invariably required in order to avoid significant artifacts in the measured PSD arising from "coincidence" events—i.e. more than one detectable particle passing through the OSZ at the same time. The resulting merged/distorted signal pulses cause systematic inflation in the measured pulse heights and therefore a shift to larger sizes in the tail of the PSD. As a result, there can be moderate-to-severe distortion in the shape of the PSD for much, if not all, of the diameter range above the threshold, $d_0$, for the SPOS measurement. Hence, concentrated samples must be diluted to the extent required before analysis, to avoid serious distortion of the measured PSD and correspondingly significant errors in the calculated volume percentage of the dispersed phase ("PDP," discussed below). This dilution function can be accomplished by a variety of means, depending on whether a fixed, predetermined dilution factor is appropriate, or an automatically determined value is desired. Examples of useful methods and apparatus for automatic (or fixed) dilution of concentrated samples are described by Nicoli et al, in U.S. Pat. No. 4,794,806 (1989), and by Nicoli, in U.S. Pat. No. 6,211,956 B1 (2001).

A second consideration is whether a reliable, reasonably accurate measurement of the large-diameter tail of the PSD—i.e. for diameters, d, above a suitable threshold, $d_0$—can be made using the SPOS-LE technique, given the fact that the vast majority (typically >99%) of the particles comprising the dispersed phase lie below $d_0$. Large numbers of these smaller particles invariably pass simultaneously through the OSZ, even when the larger particles/droplets of interest are sufficiently dilute in concentration to guarantee that they pass through the sensing zone one at a time. Fortunately, for most dispersions of interest, the presence of this "sea" of smaller particles has relatively little effect on the PSD, as measured by SPOS-LE, provided the sample has been diluted adequately. With respect to the need to measure PSD tails, this attribute constitutes one of its outstanding, intrinsic attributes. For particles larger than about 5 μm (assumed to have sufficient contrast), but smaller than the thickness of the OSZ, the pulse height, $\Delta V_{LE}$, is roughly proportional to the square of the diameter. As the particles become smaller and approach the wavelength, $\lambda$, of the light source, the physical mechanism responsible for light extinction shifts from simple geometric refraction, to light scattering, described by Mie scattering theory. The pulse height falls faster with decreasing d, approximating a $4^{th}$ power dependence. Eventually, for still smaller particles in the "Rayleigh region"—i.e., d<<$\lambda$ (≈0.7 μm for typical sensors)—the pulse height decreases to the extent of the $6^{th}$ power of d. For all intents and purposes, even large numbers of these particles are effectively invisible to the SPOS-LE measurement.

Hence, in practice, the particles of diminishing size that pass through the OSZ, although typically of enormous number compared to the population of larger particles of interest (d>$d_0$), have a negligible effect on the tail of the PSD, as measured by SPOS-LE. This assertion assumes, of course, that the sample suspension has been diluted to an adequate and appropriate extent. The effective irrelevance of the smaller particles can be confirmed by measuring the PSD tail again at lower concentration(s). If the dilution chosen for the initial measurement was appropriate, the PSD tails, expressed as the number (#) of particles per ml of the original sample, will be substantially the same and overlay one another. This equivalence, of course, is apart from statistical fluctuations resulting from inadequate numbers of particles of a given size being counted—typically a concern at the largest sizes, where the fewest particles are measured.

Figure 4B:
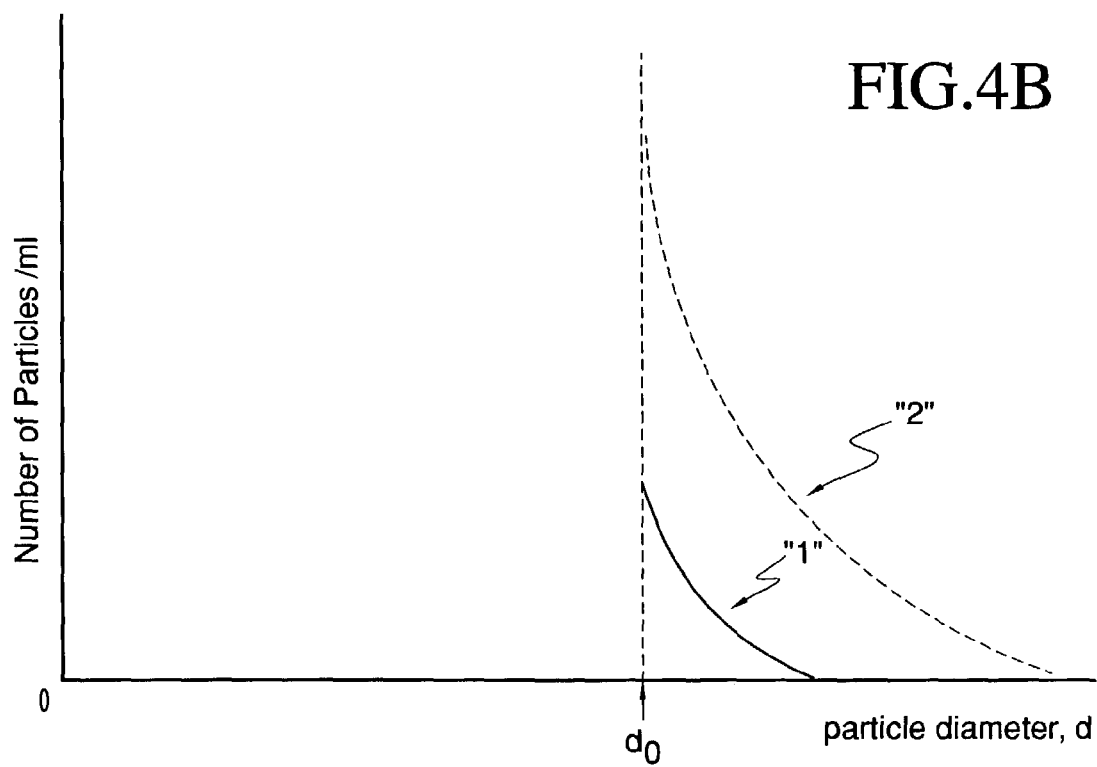
FIG. 4B shows a magnified representation of the large-particle "tails" of the PSDs obtained by SPOS seen in FIG. 4A (# particles vs diameter, d) for a stable (solid curve—"1") and unstable (dashed curve—"2") dispersion or emulsion, for particle or droplet diameters larger than the measurement threshold, $d_0$.

From the discussion above, it should be apparent that the SPOS-LE technique, by virtue of its single-particle resolution and high sensitivity (typically quadratic, or higher) to changes in particle size, is well suited to the determination of small increases in particle agglomeration associated with the acceleration of instability in dispersions. The apparent shortcoming of the technique i.e. its lack of sensitivity to particles substantially smaller than the measurement threshold, $d_0$—is, in the context of the present invention, transformed into a distinct advantage. Determination of a "partial PSD"—i.e., the tail, d>$d_0$, only—makes the resulting measurement more sensitive to a small change in a small fraction of the overall distribution, i.e., representing the larger particles/droplets. The fractional change in the population, or even better, in the volume fraction associated with the measured PSD tail is now larger. The "gain" of the SPOS-LE detection technique is therefore substantially increased, relative to that of other, "ensemble" techniques that effectively respond to all particles comprising the dispersed phase. The SPOS technique is therefore able to transform the small absolute change in the PSD seen in sample "2," relative to "1," in FIG. 4A, into a much larger relative change (d>$d_0$), seen in FIG. 4B.

Notwithstanding the evident advantage of the SPOS technique for implementing the methods of this invention, it is important to realize that other techniques for particle size analysis may be employed effectively to characterize the growing population of particle agglomerates associated with the onset of sample instability. One alternative to SPOS is a technique that also responds to individual particles—the "electrical resistive-pore," method, also known by its commercial names, "Coulter Counter™," or "Multisizer™" (Beckman-Coulter Corp., Hialeah, Fla.), and "Electrozone™" (Particle Data Inc., Elmhurst, Ill.). Particles suspended in a mildly conducting fluid (i.e. water plus electrolyte) pass one at a time through a very small orifice, causing the electrical resistance across the latter to increase momentarily. The heights of the resulting negative-going pulses in electrical current ideally increase monotonically with particle volume. Notwithstanding its principal advantage over SPOS—i.e., relative insensitivity to the optical properties of the particles—the resistive pore technique has a number of disadvantages relative to SPOS. These include: requirement of relatively concentrated electrolyte levels in the aqueous phase, susceptibility to clogging, relatively low particle counting rate and relatively small dynamic size range. The first of these disadvantages will be seen below to be particularly serious, given that the systematic addition of salt to the dispersion of interest constitutes one of the important embodiments of the present invention.

Other particle sizing methods can be considered for use in conjunction with the methods of systematic destabilization of samples described below. The most common examples of alternative techniques are those based on "ensemble" methods—i.e., which effectively respond simultaneously to particles of all sizes. One example is that of dynamic light scattering (DLS), also known as photon correlation spectroscopy (PCS). Temporal fluctuations in the scattered light intensity (at a given scattering angle) caused by random Brownian motion, or diffusion, of particles suspended in liquid can be analyzed using the intensity autocorrelation function. The latter is "inverted" mathematically, by means of one or more algorithms, to obtain an estimated PSD. Another potentially viable technique is that of "laser diffraction," usually consisting of two physical techniques, used in combination or separately—i.e., large-angle Mie scattering and forward-angle Fraunhofer diffraction. The angular-dependent diffracted intensity "pattern" is again "inverted," using appropriate algorithms, to obtain an estimated PSD. Yet another example of an ensemble technique for particle size analysis that can be considered to implement the methods taught in this invention is that of ultrasound attenuation. The variation in transmission of ultrasonic waves through a quantity of the sample as a function of wavelength, when combined with suitable inversion algorithms, can be used to obtain an estimate of the PSD.

It is important to appreciate the fact that there exist other analytical techniques, not normally associated with the measurement of particle size per se, which might be utilized with effectiveness to implement the methods of the present invention. All that is required is for these alternative techniques to be responsive with sufficient sensitivity and reproducibility to the growth in particle agglomeration (or droplet coalescence) brought about by application of one or more stress factors to the dispersion being investigated, as described below. One example is the well-known technique of classical light scattering. A light beam, typically produced by a laser source, is passed through a sample of appropriate concentration (i.e., to avoid artifacts due to multiple scattering). Light scattered simultaneously by a relatively large number of particles within a defined sensing volume is collected and detected over an appropriate range of angles, ideally chosen to produce a signal response that increases monotonically with the growth in the "tail" of large-particle agglomerates, associated with the onset of instability. The scattered intensity thus provides a "proxy" for the actual PSD that would otherwise be obtained directly, using SPOS or some other technique (including ensemble methods) for particle size analysis.

A second example of a technique that can be used as a proxy for a particle size analyzer is the simple method of turbidometry, or spectrophotometry. A light beam of an appropriate wavelength, or range of wavelengths, is passed through a fluid sample of given thickness (i.e., optical path length) and appropriate concentration. The extent to which the intensity of the light beam is attenuated is related to the underlying PSD. Assuming that the optical design has been optimized, the turbidity, or optical density, of the sample ideally increases monotonically with the growth in the "tail" of large-particle agglomerates associated with the onset of instability. The techniques of turbidometry and light scattering can be considered to be roughly complementary to each other; that is, the transmitted light intensity for the former decreases, while the intensity associated with the latter increases, with increasing particle agglomeration.

Although these, and other, ensemble techniques have been usefully applied to numerous particle-based samples, they may prove to be less useful for implementing the methods taught in the present invention. Compared to SPOS, these ensemble techniques are necessarily much less sensitive to small changes in the population of particle agglomerates, given the fact that, by nature, they respond to particles of all sizes (in the relevant size range) comprising the dispersed phase. Nevertheless, these alternative techniques may prove to have adequate sensitivity to changes in the PSD, depending on the particular dispersion being investigated and the stress factors employed. In any event, the examples chosen to illustrate the methods of this invention, discussed below, involve the use of the SPOS-LE technique to measure the PSD tails for two different miniemulsions. No loss of generality is thereby intended or implied.

To illustrate the predictive power of the methods that are the subject of this invention, it is useful to discuss the responses of specific dispersions and emulsions to various stress factors. In these examples we have chosen specific cases that represent different mechanisms for perturbing the height of the interparticle potential energy barrier in order to accelerate in a systematic way the onset of instability of these dispersions and thereby identify inferior products. One such mechanism consists of reducing the surface charge on the particles or droplets by a change of pH—e.g., "acid stress." The decision of whether to apply acid or base stress to a given dispersion is determined by the type of emulsifier or surfactant that has been used to stabilize the system. For stable dispersions containing particles that are negatively charged—e.g., coated by an anionic surfactant in a typical pH range of 6.5 to 9—the addition of acid (causing a reduction in both the pH and the surface charge) is an appropriate stress factor. Conversely, for stable dispersions containing particles that are positively-charged—e.g., coated by a cationic surfactant in a typical pH range of 4 to 6.5—the addition of base (causing an increase in the pH and decrease in the surface charge) is an appropriate stress factor. A second mechanism for inducing accelerated instability in a system consists of reducing the surface charge on the particles or droplets by selective adsorption of charged ions of opposite sign—e.g. "calcium chloride stress." Finally, a third mechanism for reducing the interparticle repulsive potential energy consists of adding mobile charged ions to the system—e.g., "sodium chloride stress:" These non-adsorbing, freely-diffusing ions in the aqueous phase serve to screen the electrostatic fields, giving rise to interparticle repulsive forces, that exist between the charged particles.

The first example of a product that can be systematically stressed to permit successful accelerated testing of stability is a dairy fat emulsion—i.e., commercially available whole (homogenized) milk. Whole milk is an oil-in-water emulsion that contains dairy fat droplets dispersed in water. The fat droplets are charge-stabilized by a coating of bovine casein, a protein of moderately large molecular weight (~23,600 Daltons) that exhibits its primary emulsifying action via ionization of its anionic amino acid head groups. In addition to imparting a net negative charge to the fat droplets, thereby providing inter-droplet electrostatic repulsions, the molecules of casein may provide additional stabilization against coalescence through the mechanism of steric hindrance. Commercially available milk generally has a shelf life of about two weeks. The quality of the homogenized dispersion can be evaluated qualitatively by simple sensory assessments. These include whether it is visually obvious that dairy fat from the dispersed phase has separated from the continuous bulk aqueous phase, and/or whether there is a foul smell and/or taste—i.e. a "souring" of the final product. The souring of milk indicates failure of the dispersion, and its occurrence ideally coincides with, or immediately follows, the expiration date (ED) printed on the container, although in practice this is rarely the case.

Three different batches of whole milk from a single producer were investigated and identified by their EDs—specifically, June 8 ("0608"), June 12 ("0612") and June 15

("0615"). As a reference point, the first study commenced 1 day, 5 days and 8 days before the producer-assigned shelf lives of batch #1, batch #2 and batch #3, respectively. For each experiment, the product was examined visually for evidence of phase separation and by smell for the presence of a foul odor; by pH; and by measurement of the large-diameter (>1.8 µm) tail of the PSD. Particle size analysis was accomplished using the technique of single-particle optical sensing (SPOS) based on light-extinction, or "SPOS-LE" (AccuSizer™ 780/APS, Particle Sizing Systems Inc., Santa Barbara, Calif.). In all cases the results are expressed as the volume-weighted percentage of the dispersed phase ("PDP") for fat droplets larger than 1.8 microns (range: 1.8–50 µm). two different studies were carried out on each of the three batches of whole milk, and the effects of various stress factors were investigated.

The purpose of the first study was to evaluate the effects of "pH stress" on the stability of whole milk. This negatively-charged dispersion, stabilized by bovine casein typically at pH=6.5, was stressed by addition of acid, resulting in a reduction of surface charge on the finely dispersed milk-fat droplets, thus inducing agglomeration. The milk batches were acidified using a standard buffer solution, constructed from stock solutions of 0.1 M (21.01 g/L) citric acid monohydrate ($C_6H_8O_7.H_2O$) and 0.2 M (28.44 g/L) dibasic anhydrous sodium phosphate ($Na_2HPO_4$). Specified volumes of each stock solution were added together to make a final buffered solution, having the desired pH values of 6.1 and 5.7, from a range of values extending from pH=2.2–7.8, that are possible with mixtures of these two solutions, as described by McIlvaine in J Biol Chem, Vol. 49, p. 183 (1921). The buffered milk samples were mixed with the appropriate "McIlvaine buffer mixture" in a 1:1 volume ratio. The final lipid concentration of these samples was therefore equal to one-half of the unbuffered controls. As a result, the volume-weighted PDP computations for each buffered sample were appropriately adjusted to the new final lipid concentration at baseline. Two different buffer combinations were added to separate aliquots of the three whole milk samples, in order to reduce in two stages the pH of the aqueous phase in those samples. The function of the acid stress was to reduce systematically the average charge on the surfaces of the fat droplets, by virtue of progressive neutralization of some of the negatively-charged amino acid groups in the molecules of bovine casein adsorbed to the droplets. As a consequence of this action, there was a systematic reduction (in two stages) in the interparticle repulsive force, thereby allowing the process of fat droplet coalescence to accelerate in time.

Aliquots of whole milk from each of the three batches (three different ED values) were subjected to controlled acid-induced stress and the PSD measured at four different time points: t=0, 80, 160 and 240 minutes (approximately) after addition of acid. (The actual elapsed times for each sample deviated somewhat from these values, owing to the accumulated delays caused by the few minutes needed to perform each PSD measurement.) Before the time sequence commenced, each batch was measured without added acid (pH≈6.5), to establish the "control" PSD for itself Each was then analyzed again at the time points indicated, after being subjected to acid stress (nominally at t=0) using standard buffer solutions at two lower, fixed pH levels: $pH_1$=6.1 and $pH_2$=5.7. These values were chosen to approach progressively the isoelectric point (charge≈0) for bovine casein, pH≈4.7. The milk samples were refrigerated at 4–8° C. throughout the study prior to PSD determination, conducted at room temperature (23–26° C.).

Figure 5:
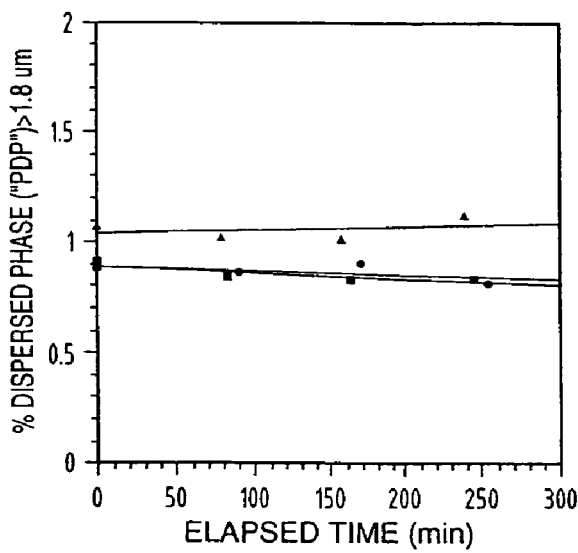
FIG. 5 shows the percentage (v/v) of the dispersed phase (d>1.8 μm), or "PDP," vs elapsed time obtained for three "control" batches of whole milk (no change in pH): "0608," or batch#1 (solid circles); "0612," or batch#2 (solid squares); and "0615," or batch#3 (solid triangles)

FIG. 5 depicts the PDP values (i.e., the volume of fat droplets larger than 1.8 µm, expressed as a percentage of the total fat volume) vs elapsed time, t, obtained from the three control samples of whole milk, in the absence of exogenous buffers. The plots of PDP vs t are nearly the same (apart from experimental scatter) for batches #1 ("0608," solid circles) and #2 ("0612," solid squares). However, the plot obtained for batch #3 ("0615," solid triangles), the "youngest" sample according to its ED value, exhibits a slightly higher percentage of large-diameter fat droplets compared to the other, "older" batches. This latter behavior is interesting, but of no particular significance, as will be appreciated shortly.

Figure 6:
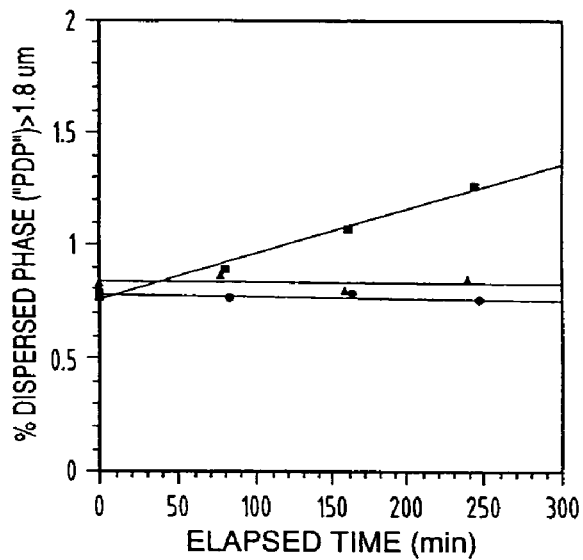
FIG. 6 shows the PDP (d>1.8 μm) vs elapsed time obtained for three batches of whole milk after the application (t=0) of acid stress (pH=6.1): "0608" (solid circles), "0612" (solid squares) and "0615" (solid triangles)

The effect of acid stress on the three whole milk samples produces a surprising result, as seen first in FIG. 6. At the lowest level of stress—pH lowered from 6.5 to 6.1—the PDP for batch #2 (solid squares, FIG. 6) shows a steady increase in the volume of large (i.e., coalesced) fat droplets with elapsed time, from approximately 0.8% at t=0 to 1.25% at t≈240 min. These changes reflect significant and progressive growth (i.e. coalescence) of fat droplets in the large-diameter tail of the PSD. In sharp contrast to this result, the PDPs for batches #1 (solid circles) and #3 (solid triangles) remain essentially constant over time (again, apart from experimental "noise"), showing no measurable changes in stability even in the "buffered samples" that were diluted in a 1:1 volume ratio. The surprise, of course, is that, based on the ED values indicated for each batch, one would expect the oldest product, batch #1 ("0608"), to be the sample that exhibits the greatest instability due to lowered pH. If the effect of the acid stress is large enough (i.e. the lowering of the interparticle energy barrier is great enough) to cause batch #2 to exhibit accelerated instability (droplet coalescence) with time, then batch #1, having a 4-day earlier ED, should exhibit the same, or even worse, behavior. This is clearly not the case. The date of testing was only one day before the assigned ED of batch #1, but fully 5 days before the ED of batch #2. However, based on the PDP values obtained after acid-stressing these two samples, it is clear that there was significant deterioration in the quality of the milk in batch #2, compared to the milk in batch #1, prior to testing. This finding represents a complete reversal of the behavior that would be expected based on the assigned ED values for the two products.

Figure 7:
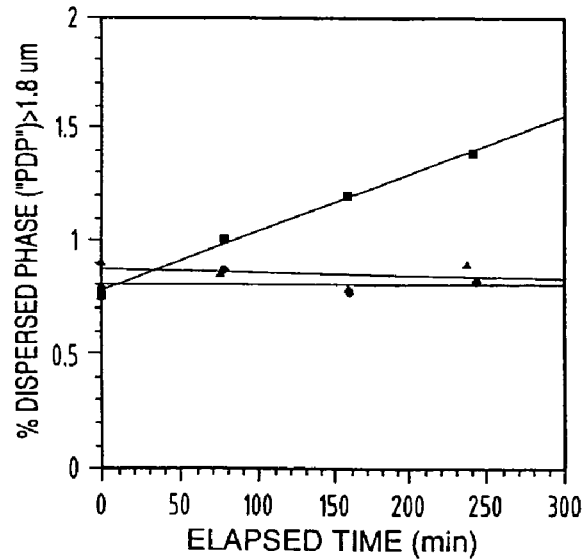
FIG. 7 shows the PDP (d>1.8 μm) vs elapsed time obtained for three batches of whole milk after the application (t=0) of acid stress (pH=5.7): "0608" (solid circles), "0612" (solid squares) and "0615" (solid triangles)

The same behavior for the three batches of milk is mirrored in FIG. 7, which shows PDP vs t obtained following a more powerful stress of the samples—i.e. a larger reduction in pH, from 6.5 to 5.7. In this case, the PDP value for batch #2 (solid squares) increased approximately to 1.4% after 240 min, compared to 1.25% for the somewhat milder pH reduction (from 6.5 to 6.1). This behavior is not surprising. Once the sample exhibits instability due to application of a particular stress factor (e.g., reduction of pH) at a given level (i.e., ΔpH), the higher the stress level (i.e., the larger ΔpH), the greater the response (i.e., the larger the PDP). What is surprisingly, however, is the fact that there was still no observable change in the behavior of batch #1 (solid circles) due to this larger level of acid stress. Finally, and not surprisingly, there was essentially no measurable effect of the higher level of acid stress on the PDP values obtained for batch #3 (solid triangles), the "youngest" of the three batches of milk, with fully 8 days remaining before is ED.

The observed dependence of the computed PDP on elapsed time and acid-stress level (pH) for each batch of milk, shown in FIGS. 5–7, is summarized in Table I. The results of linear regression analyses performed on the PDP vs t data for each value of pH and each batch of milk are also summarized in Table I. Very high values of the correlation coefficient, r—i.e., very close to the ideal value (r=1), consistent with nearly perfect correlation between the PDP and elapsed time, t—are exhibited by batch #2 (0612) for each of the acid-stress (pH) levels. Specifically, r=0.995 and 0.997 for pH=6.1 and 5.7, respectively (bold type in Table I). The indicated slope values associated with each value of reduced pH, obtained by least-squares linear fits to the observed PDP vs t data, provide a useful quantitative measure of the inferiority of batch #2—i.e. how quickly it destabilizes after application of the acid stress factor. It would be useful to divide the increase in slope (i.e., relative to the control sample) by the change in pH, $\Delta$pH, in order to arrive at a quantitative measure of the instability induced in the sample by application of that particular level of stress. The fact that the r-values are so close to unity for batch #2 reinforces the predictive value of the accelerated stress-testing method outlined in the present invention and ratifies the conclusion of instability, or inferiority, previously drawn for this sample. No such strong correlation between the calculated PDP values and the elapsed time is found for either batch #1 or #3 for either stress level (i.e., either reduced pH value), as discussed qualitatively earlier. The value of the regression analysis is obvious—it permits quantitative significance to be associated with the observed experimental results.

Figure 8:
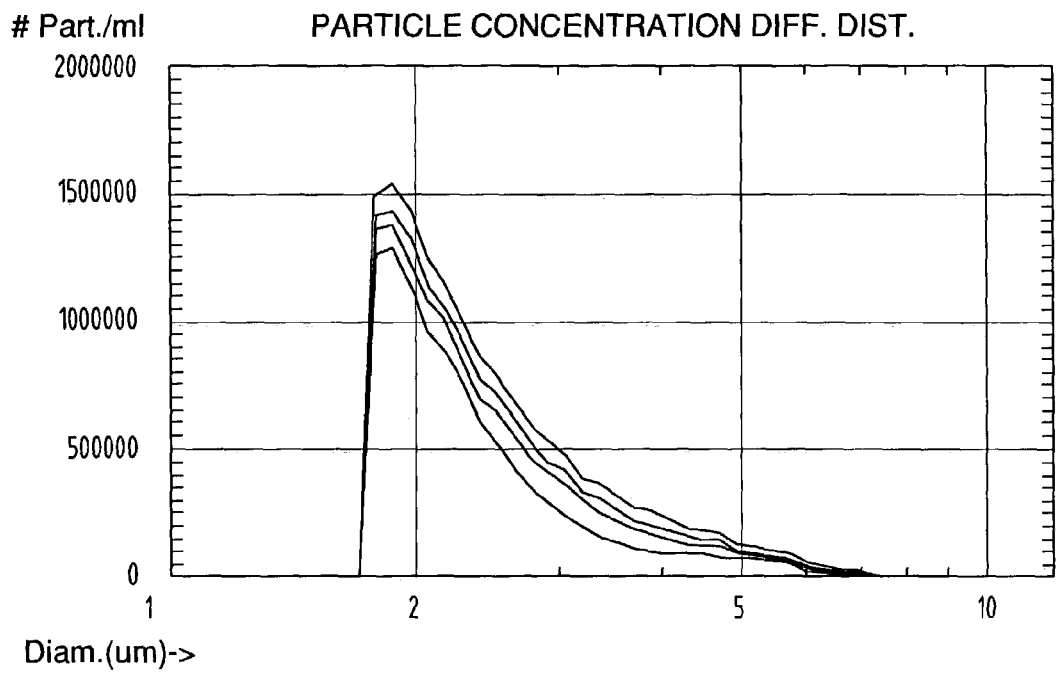
FIG. 8 shows the growth of the large-particle "tail" of the PSD (# particles/ml>1.8 μm) obtained by SPOS for batch #2, or "0612," of whole milk after the application of acid stress (pH=5.7), corresponding to the four PDP values shown in FIG. 7 (solid squares)
Figure 9:
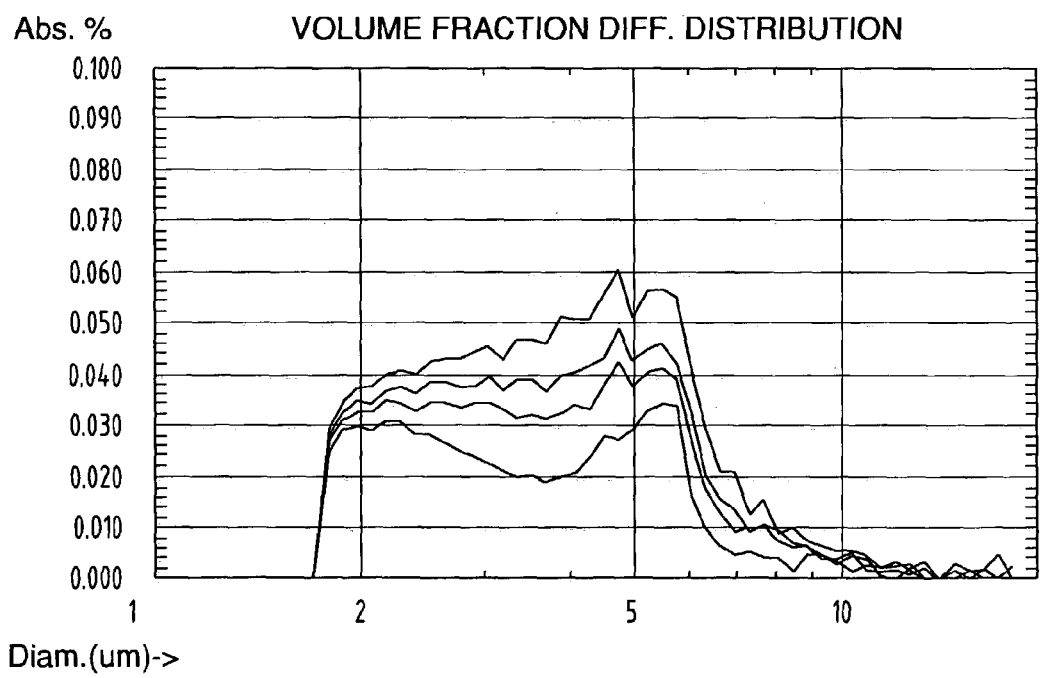
FIG. 9 shows the progressive increase in the absolute volume fraction (i.e. PDP vs d) for batch #2, or "0612," of whole milk after the application of acid stress (pH=5.7), corresponding to the four PSD "tails" (d>1.8 μm) shown in FIG. 8.

Representative PSD results obtained by SPOS-LE for the acid-stressed (pH 5.7) batch #2 milk samples, from which the PDP values in FIG. 7 were computed, are shown in FIG. 8. The four "tails" of large-diameter (>1.8 µm) fat droplets (or, more correctly, "globules") were obtained at approximate elapsed times of 0, 80, 160 and 240 minutes for batch #2, acid-stressed at pH 5.7. These tails are plotted in the form of population concentration—i.e. # particles (droplets) per ml of milk versus particle diameter (µm). They show unambiguously an increase in the concentration of large fat globules with elapsed time, due to progressive coalescence of droplets caused by acid, or low-pH, stressing of the sample. These "tail" results are similar to those depicted schematically in FIG. 4B, discussed previously. FIG. 9 shows the differential distributions of the absolute volume fractions of the fat globules corresponding to the particle concentration tails of FIG. 8. The increase in volume fraction of the dispersed phase at each droplet diameter with increasing elapsed time is evident. The cumulative sum (over all particle diameters) of all the volume fractions for each sample yields each of the PDP values for batch #2 (pH=5.7) that are plotted in FIG. 7. In summary: lowering the surface charge of the fat droplets by acid stressing resulted in the clear identification of a relatively inferior milk product, relative to an older batch that tested superior and that would have been assumed to fail first, based on its earlier assigned expiration date (ED). Stressing of these batches was required in order to discover this unexpected result, because the PDP values in the absence of acid stressing were essentially the same for all three batches tested (FIG. 5). Hence, the usefulness of this new method of systematic, incremental stressing of an emulsion/dispersion, coupled with a sensitive measurement of the resulting small changes in the volume fraction of large particles, or droplets, in the dispersed phase, should be apparent.

The second study consisted of exposing the same three batches of whole milk to a second kind of stress factor—addition of adsorbing electrolyte, permitting dissociated ions of the appropriate charge, that are able to adsorb to the surfaces of the fat droplets. Specifically, calcium chloride ($CaCl_2$), an inorganic divalent salt, was added to the milk samples, causing some of the dissociated $Ca^{++}$ ions to become bound to the surfaces of the droplets. The stressed samples were prepared using a standard stock solution consisting of 0.2 M (29.4 g/L) calcium chloride dihydrate ($CaCl_2 \cdot 2H_2O$). In order to produce the desired final added calcium concentration of 0.005M (0.735 g/L), 1 mL of the calcium chloride stock solution was added to 39 mL of milk. In the case of the final desired calcium concentration of 0.010M (1.47 g/L), the ratio of calcium stock solution to milk sample was doubled (i.e., 1 mL added to 19 mL). As a result, the volume-weighted PDP computations for each calcium-stressed sample were appropriately adjusted to the new final lipid concentration at baseline. Thus, two different calcium stress concentrations were added to separate aliquots of the three whole milk samples, in order to increase in two stages the calcium concentration in the aqueous phase in those samples. Like the acid-stress factor utilized in the first study, this second stress factor was designed to reduce the net charge on the droplets, thus reducing the height of the inter-droplet energy barrier and promoting droplet coalescence. However, in this case the means for reducing the surface charge is different. First, positively-charged $Ca^{++}$ ions adsorb onto the surfaces of the oppositely charged droplets (made negatively-charged at pH 6.5 by virtue of the already-adsorbed molecules of bovine casein) that causes a net reduction of the charge on each particle. The greater the concentration of $CaCl_2$ added to the sample, the greater the number of $Ca^{++}$ ions that become bound to each casein-coated fat droplet, and the lower the resulting average charge on the latter. (This conclusion assumes that the added concentration of $Ca^{++}$ is not so high as to cause charge "reversal," resulting in a net positive charge on the particles.)

Therefore, to first approximation, stressing the milk samples by addition of $CaCl_2$ should have much the same effect as stressing it with added acid in the first study—i.e. reducing the net charge on the fat droplets, thereby reducing the height of the inter-droplet energy barrier. However, there is an additional factor that comes into play—i.e., potentially significant reduction in the thickness (and hence overlap) of the electrical double layers associated with the charged particles, due to the dissociated, mobile $Ca^{++}$ and $Cl^-$ ions that diffuse in the continuous aqueous phase of the milk. This screening mechanism has the effect of further reducing the barrier height, which provides additional destabilizing stress to the dispersed fat droplets. In principle, the addition of this mechanism should cause faster and more extensive droplet coalescence than would otherwise occur simply by reducing (by a given amount) the average charge on the droplets, in the absence of a significant increase in screening of the electrostatic repulsion between droplets.

Figure 10:
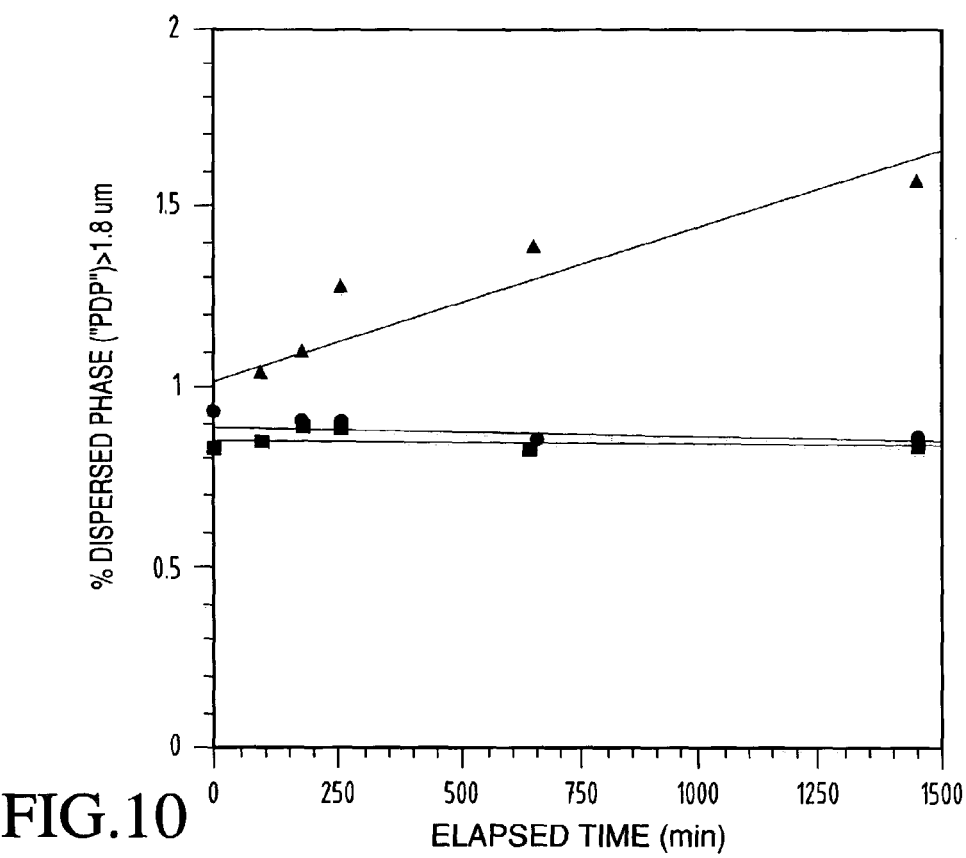
FIG. 10 shows the PDP (d>1.8 μm) vs elapsed time obtained for batch "0608" of whole milk after the application (t=0) of calcium chloride stress: 0M $CaCl_2$, "control" (solid circles), 0.005M $CaCl_2$ (solid squares) and 0.01M $CaCl_2$ (solid triangles)
Figure 11:
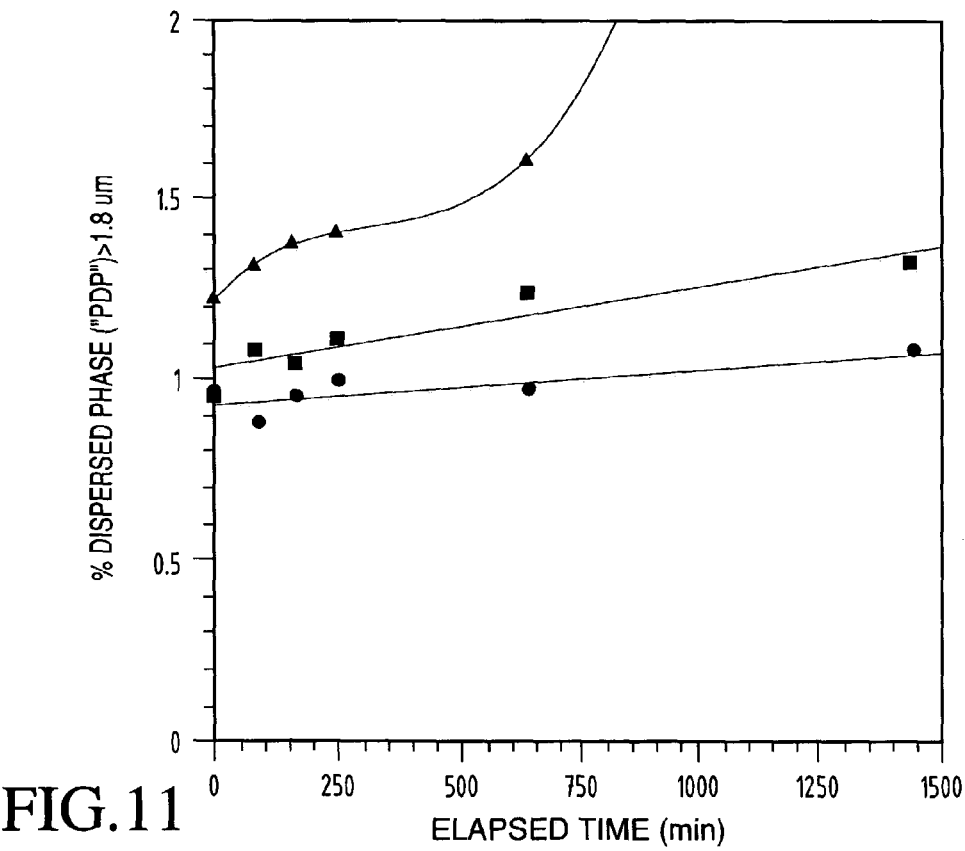
FIG. 11 shows the PDP (d>1.8 μm) vs elapsed time obtained for batch "0612" of whole milk after the application (t=0) of calcium chloride stress: 0M $CaCl_2$, "control" (solid circles), 0.005M $CaCl_2$ (solid squares) and 0.01M $CaCl_2$ (solid triangles)

The second study was conducted two days after the acid-stress study was carried out. Hence, the ED for batch #1 was exceeded by one day, with 3 days remaining before the ED of batch #2 and 6 days before the ED of batch #3. Each batch was subjected to "calcium-stress" at two different concentrations of added Ca++, equal to 0.005M and 0.01M. Each batch provided its own "control"—i.e. in the absence of added $CaCl_2$. The milk samples were studied at six different time intervals over a 24-hour period, and all samples were refrigerated (4–8° C.) between analyses, conducted at room temperature, as before. The effects of the ionic challenges on the stability of the dispersions vis-à-vis fat droplet coalescence are summarized in FIGS. 10–13. FIG. 10 summarizes the calculated values of PDP vs t over a period of 24 hours for batch # 1 ("0608") for the "control" sample (no added $CaCl_2$, solid circles) and the two concentrations of added $CaCl_2$, 0.005M (solid squares) and 0.01M (solid triangles). FIG. 11 summarizes the results for batch #2 ("0612"), and FIG. 12, the results for batch #3 ("0615"), using the same symbols as in FIG. 10. FIG. 13 is a compressed version of FIG. 11, allowing the entire set of data points for batch #2, 0.01M $CaCl_2$ (solid triangles) to be plotted.

Figure 12:
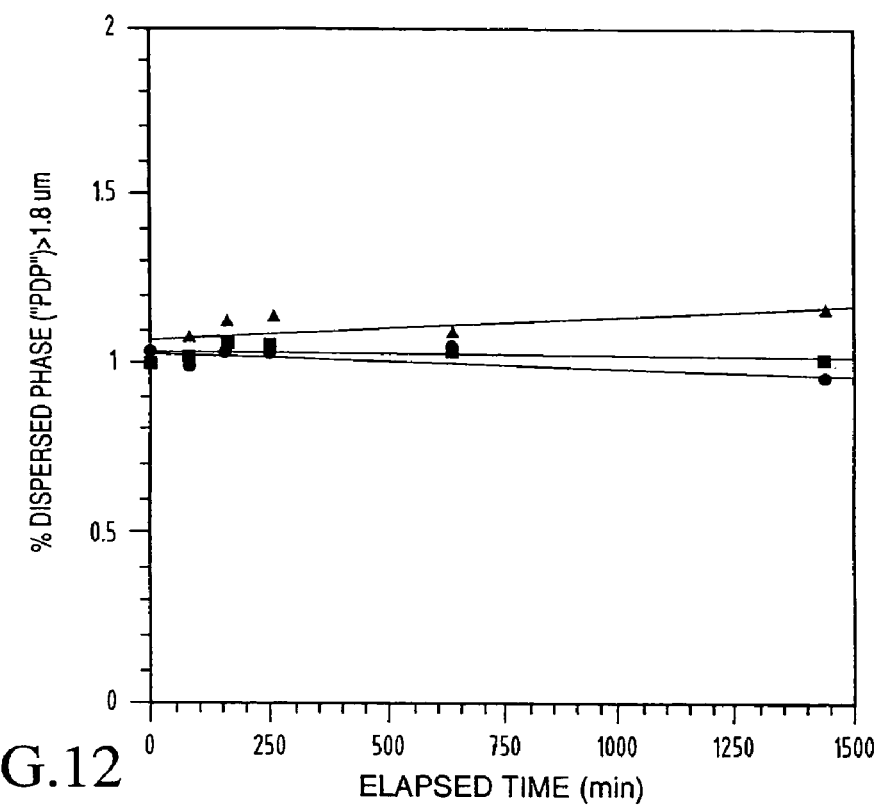
FIG. 12 shows the PDP (d>1.8 μm) vs elapsed time obtained for batch "0615" of whole milk after the application (t=0) of calcium chloride stress: 0M $CaCl_2$, "control" (solid circles), 0.005M $CaCl_2$ (solid squares) and 0.01M $CaCl_2$ (solid triangles)
Figure 13:
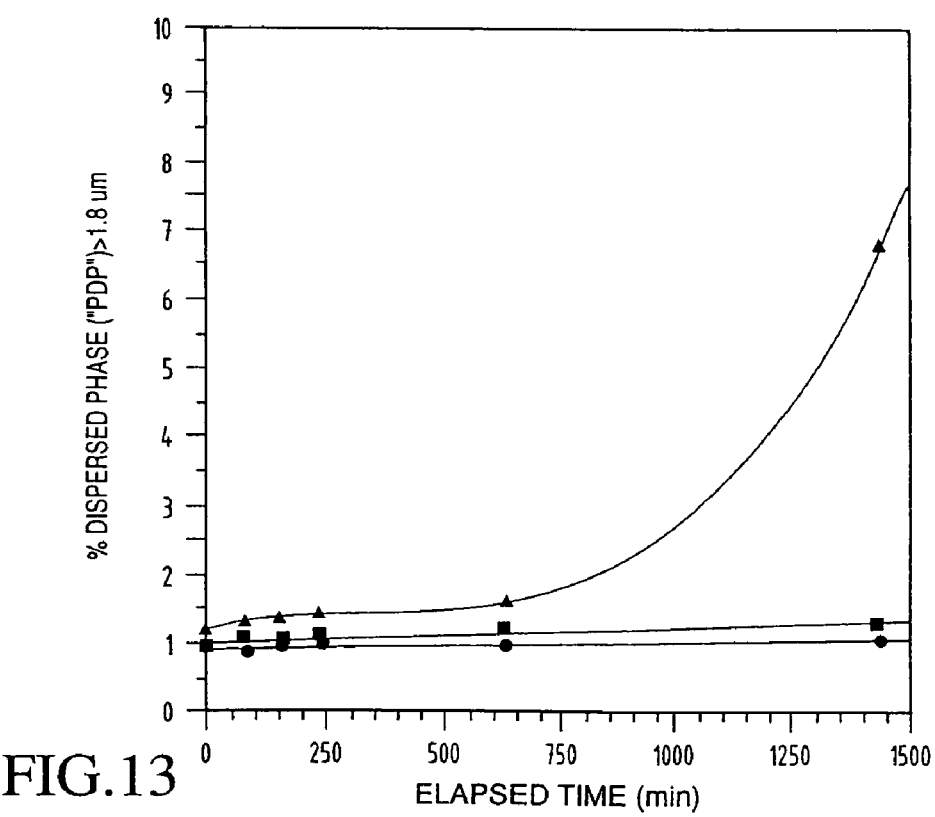
FIG. 13 is a compressed-scale version of FIG. 11—PDP (d>1.8 μm) vs elapsed time for batch "0612" of whole milk after the application (t=0) of calcium chloride stress: 0M $CaCl_2$ (solid circles), 0.005M $CaCl_2$ (solid squares) and 0.01M $CaCl_2$ (solid triangles)

As can be seen from FIGS. 10 and 12, the addition of 0.005M: $CaCl_2$ to the milk had no appreciable effect on the measured PDP values for batches #1 and #3. There were no measurable changes in stability, even in the "calcium-stressed samples," with diluted ratios of 1:39 and 1:19 volume ratios for the 0.005M and 0.010M aliquots, respectively. That is, there was no significant growth in the concentration of the large-diameter fat globules comprising the tails of the measured PSDs. Clearly, this level of added $CaCl_2$ was insufficient to destabilize batches #1 and #3 significantly over the time frame investigated. However, this lowest level of calcium stress produced a measurable increase in the PDP values (except at t=0) for batch #2, as seen in FIG. 11. Once again, batch #2 revealed its inferior nature under stress, notwithstanding the fact that there were 3 days remaining before its indicated ED, compared to one day past the indicated ED for batch #1.

It is instructive to compare these results with the corresponding findings obtained when the concentration of added $CaCl_2$ was doubled, to 0.01M. In the case of batch #1 (FIG. 10, solid triangles), this elevated level of stress yielded significant time-dependent growth in the PDP, from just under 1% at t=0, to roughly 1.5% at t=24 hrs. Even though this sample previously resisted the levels of acid stress applied to it over the period of time of analysis, batch #1 clearly was affected by this higher level of calcium stress—possibly associated with its advanced age (i.e., beyond its ED). Importantly, it should be pointed out that the highest concentration of the $CaCl_2$ stress factor was still required to destabilize batch #1, despite the advanced age of the product. In the case of batch #2 (FIG. 11, solid triangles), the higher stress level also yielded significant t-dependent growth in the PDP, reminiscent of that observed for batch #1 for elapsed times up to and including ≈12 hours. However, beyond that time the measured PDP accelerated greatly with increasing time, as seen in FIG. 13 (solid triangles, with the PDP scale compressed 5-fold), reaching almost 7% after 24 hours. (There was also strong evidence of souring at this point.) This result is entirely consistent with the findings obtained previously for batch #2, again firmly establishing its inferiority with respect to the other two samples, most notably batch #1. Clearly, this level of calcium chloride stress can no longer be considered to be a "small" perturbation of the dispersion in the case of batch #2, given the eventual much larger, nonlinear response of the measured PDP to the added $CaCl_2$ after more than 12 hours have elapsed. (Even the previously stable batch #1 "collapsed" under the concentrated conditions in this case.) In the case of batch #3 (FIG. 12, solid triangles), the higher stress level yielded only slight growth in the PDP over the full elapsed time period, consistent with the fact that this was the "youngest" milk product and therefore, not surprisingly, the most stable.

The observed dependence of the computed PDP on the elapsed time and calcium-stress level, [$CaCl_2$] for each batch of milk, shown in FIGS. 10–13, is summarized in Table II. The results of a linear regression analyses performed on the PDP vs t data for each value of [$CaCl_2$] and each batch of milk are also summarized in Table II. Nearly ideal values of the correlation coefficient, r, are exhibited by batch #2 (0612) for each of the calcium stress levels, [$CaCl_2$]. Specifically, r=0.927 and 0.934 for [$CaCl_2$]=0.005M and 0.1M, respectively (bold type in Table II). The indicated slope values associated with each value of [$CaCl_2$] again provide a useful quantitative measure of the inferiority of batch #2. As with acid stressing, it would be useful to divide the increase in slope (i.e., relative to the control sample) by the value of added [$CaCl_2$], in order to obtain a quantitative measure of the instability induced in the sample by application of a given stress level. The fact that the r-values are relatively close to unity for batch #2 again reinforces the predictive value of the accelerated stress-testing method outlined in the present invention and again ratifies the conclusion of instability, or inferiority, previously drawn for this sample. As discussed qualitatively above, a similar, but not quite as strong, correlation (r=0.897) between the calculated PDP values and the elapsed time, t, was found for batch #1 at the highest stress level employed, [$CaCl_2$]=0.01M. By contrast, only a moderately-strong correlation (r=0.639) was found for the PDP vs t response of batch #3 at the same, highest stress level, owing to the fact that it was the youngest, and presumably most stable, of all three samples. The fact that the r-value is significant not just for batch #2, but also for batches #1 and #3 at the highest [$CaCl_2$] employed, suggests the likely existence of a "threshold" limit for this calcium-stress factor. At this level, instability is induced in all of the batches of milk, irrespective of their intrinsic quality.

Figure 14:
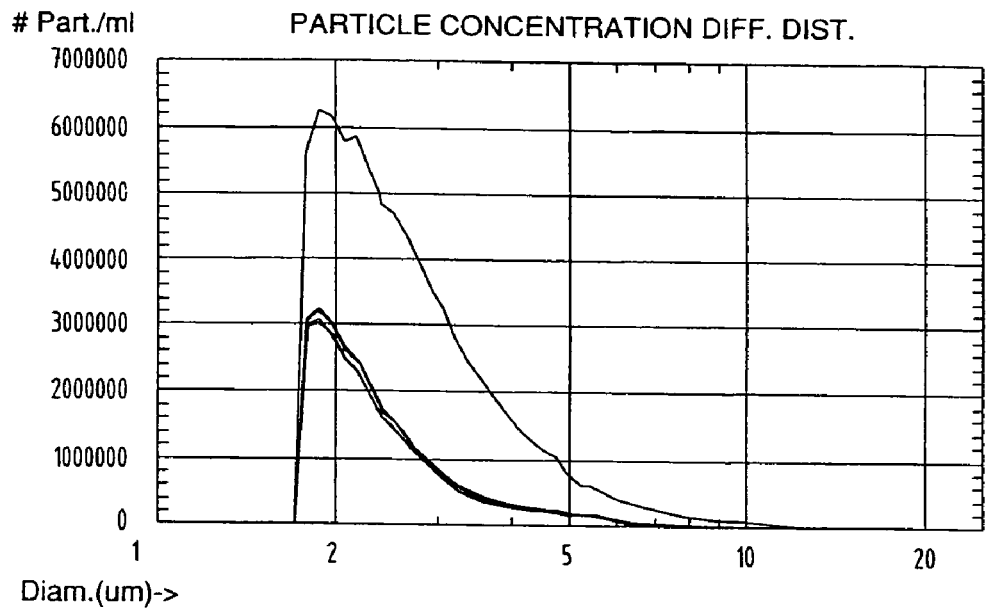
FIG. 14 shows the growth of the large-particle "tail" of the PSD (# particles/ml>1.8 μm) obtained by SPOS for the milk sample "0612" after the application of calcium chloride stress (0.01M $CaCl_2$), corresponding to the six PDP values shown in FIG. 13 (solid triangles)
Figure 15:
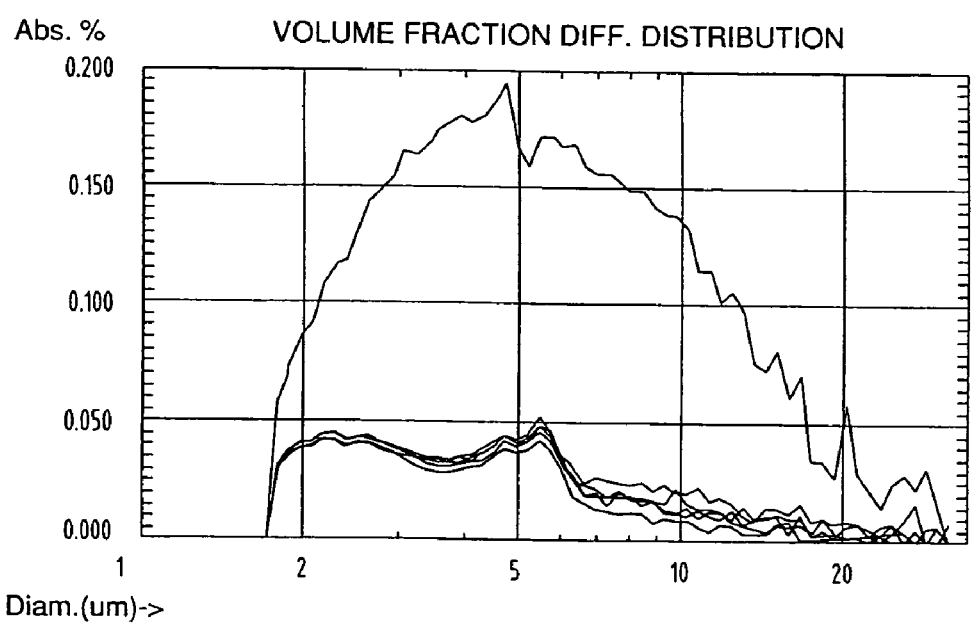
FIG. 15 shows the progressive increase in the absolute volume fraction (i.e. PDP vs d) for batch "0612" of whole milk after the application of acid stress (pH=5.7), corresponding to the four PSD "tails" (d>1.8 μm) shown in FIG. 14.

In closing the discussion related to the second study, involving calcium stress, it is also instructive to examine briefly the PSDs obtained for the inferior milk sample, batch #2, with the higher level of added $CaCl_2$, 0.01M, that produced the elevated PDP values shown in FIGS. 11 and 13. The differential concentration PSD tails—# particles/ml vs particle diameter (>1.8 μm)—obtained at the six measured elapsed times are shown in FIG. 14. The progressive increase in the value of PDP with increasing time up to ≈12 hrs, obvious in FIG. 11, is seen as a relatively small "detail" in FIG. 14, with the PSD tails closely resembling each other. These changes are dwarfed by the enormous growth in the tail observed after 24 hours, corresponding to the very large growth in the PDP at this time seen in FIG. 13. The corresponding plots of the absolute volume fractions for these six PSD tails are shown in FIG. 15. Again, there was clearly an enormous increase in the concentration of large ("outlier") fat globules that developed between 12 and 24 hours for batch #2, consistent with its having been identified as an inferior sample, using the other stress factors applied earlier. The results of these calcium-stress experiments suggest an age-dependent, as well as a concentration-dependent, effect of added calcium ions on the stability of whole milk, again demonstrating the lack of agreement between the assigned shelf-life (ED) and the observed stability under stress for batch #2. In this case, it appears that the elevated level (i.e. 0.01M) of calcium stress applied to the milk samples was higher than necessary, as all formulations were adversely affected to one degree or another. Nevertheless, the response of batch #2 (previously identified as flawed) to the elevated stress level was, again, significantly greater than the others. As discussed earlier, the additional screening mechanism coupled with the adsorption of calcium ions to the droplet surfaces caused faster and more extensive droplet coalescence compared to the case of acid stress.

The results of the stress studies reviewed above clearly demonstrate the ability of this new accelerated stress testing method to detect significant differences between three separate batches of milk produced by the same processing plant.

Application of the novel methods of this invention exploited the differences in the quality of different milk samples by means of two different types of stress factors. Each stress factor had the effect of lowering the relative height, $V_{MAX}/kT$, of the inter-droplet potential energy barrier that is responsible for minimizing the rate of droplet coalescence, thus ensuring stability of the product for an acceptable period of time. Although the mechanism for reduction of the relative barrier height is different for each stress factor, in each case batch #2 of milk was unambiguously identified as inferior from the point of view of stability, relative to the other batches. Hence, it is clear that the new methods taught herein are capable of discerning, on both a qualitative and quantitative basis, differences in stability, or quality, between dispersions and emulsions that may not be reliably identified using traditional, existing methods. It is also clear that conventional expiration date assignments for commercial products, even those that are well established, are not necessarily valid.

In order to illustrate further the universal applicability and effectiveness of the new methods for accelerated stress testing of dispersions, it is useful to summarize the results obtained from similar studies, applied to another type of oil-in-water emulsion. The dispersed phase consists of droplets of vegetable oil, stabilized by an anionic surfactant, utilized to impart a negative charge to the surfaces of the oil droplets. As described below, one of the stress factors that was applied to the vegetable fat emulsion derives its effectiveness from a mechanism that is different from that represented by the stress factors applied in the milk studies described above. The stressed samples were analyzed as before, using particle size analysis (SPOS) based on light extinction (i.e., SPOS-LE), and the results again expressed as the volume percentage of large-diameter (range: 1.8–50 µm) oil droplets ("globules"), or PDP, at various elapsed time intervals.

In these studies (three distinct experiments), a low concentration (0.05M) mixture of monovalent cations ($Na^+$, $K^+$) and a low concentration (0.003M) mixture of divalent cations ($Ca^{++}$, $Mg^{++}$) were added to a 5% w/v oil-in-water vegetable fat emulsion, in order to evaluate the effects of the mixture of added ions (both adsorbing and screening) on emulsion stability over time. This baseline mixture of destabilizing cations used throughout these experiments is referred to hereafter as "mixed ionic species." The final dispersion of vegetable fat emulsion and mixed ionic species was evaluated, as before, by means of measurement of the PSD at time t=0 (i.e., immediately after the addition of the mixed ionic species). The dispersion was measured again after 8, 16, 20, 24 and 28 hours at room temperature (23–26° C.). The resulting behavior of PDP vs t is summarized in FIG. 16. There was measurable growth in the large-diameter tail of the PSD, indicating the onset of significant oil droplet coalescence, which appeared after approximately 20 hours (1200 minutes). The resulting PDP values grew significantly shortly thereafter. This "control" experiment established that the addition of low concentrations of the mixed ionic species to the vegetable oil emulsion caused it to become unstable, but with clear manifestation occurring only after an elapsed time of approximately 24 hours.

In order to evaluate further the effectiveness of the new methods taught herein, different stress factors were systematically applied to this charge-stabilized vegetable oil emulsion, in order to determine whether its unstable character could be reliably ascertained much sooner than 20 hours—i.e. on a greatly accelerated basis. One of these factors was the controlled addition of a simple monovalent salt, NaCl.

Unlike the addition of $CaCl_2$ to the milk dispersions, causing the charge on the fat droplets to be reduced due to binding of some of the added $Ca^{++}$ ions, the addition of NaCl to the dispersion should not have resulted in appreciable binding of $Na^+$ ions to the negatively charged oil droplets. Rather, in this case the main effect of the added salt ions was to partially screen the electrostatic repulsions between the charged droplets (i.e., shrinking the electrical double layers associated with the droplets), thus promoting their coalescence. While the use of a simple monovalent salt, NaCl, has been described for partially screening electrostatic interparticle repulsion, it is to be understood that a simple divalent or trivalent salt could also be used for partially screening the electrostatic repulsions.

In the second series of experiments, the baseline amounts of the "mixed ionic species" (same concentrations used previously) were added to four separate aliquots, or batches, of the same vegetable oil emulsion (5% w/v) used in the experiment just discussed (i.e., the "baseline" dispersion). At the same time (t≈0) the batches were systematically stressed, using the screening-only mechanism just discussed. Progressively higher concentrations of NaCl were established in each sample: batch #1=0M ("control," baseline mixed ionic species); batch #2=0.05M (2.93 g/L); batch #3=0.1M (5.86 g/L); batch #4=0.15M (8.79 g/L). (Batches 2–4 were equal to batch #1 plus increasing levels of salt stress.) As a result, the volume-weighted PDP computations for each salt-stressed sample were appropriately adjusted to the new final lipid concentration at baseline. Each batch was then assessed for stability at room temperature (23–26° C.) from measurements of the PSD, as before, but at five different time points: t=0, 60, 120, 180 and 240 minutes (approximate times). This study was designed to accelerate systematically the onset of significant, measurable oil droplet coalescence by approximately an order to magnitude in time—i.e., from 20 hours to only 1–4 hours.

Figure 16:
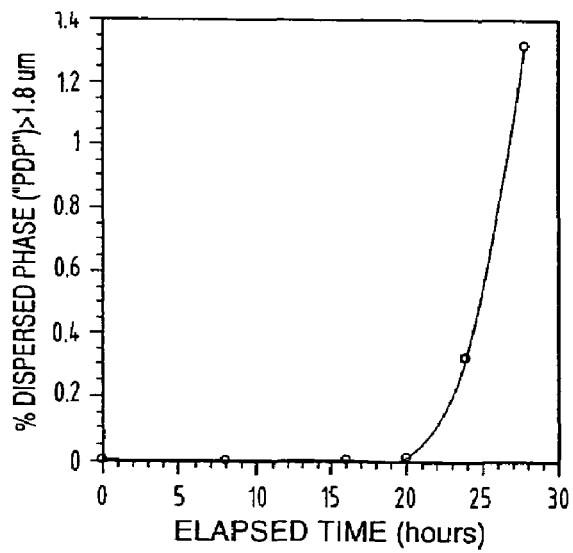
FIG. 16 shows the PDP (d>1.8 μm) vs elapsed time (expressed in hours, with a maximum equal to 1800 min) for a lecithin-stabilized vegetable oil emulsion after the addition (t=0) of a destabilizing mixture of ionic species over 28 hours.
Figure 17:
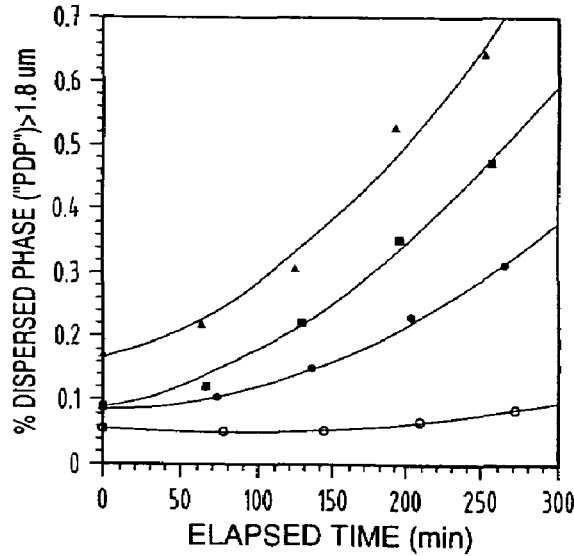
FIG. 17 shows the PDP (d>1.8 μm) vs elapsed time obtained for the vegetable oil emulsion of FIG. 16 after the addition (t=0) of mixed ionic species and application of sodium chloride stress: 0M NaCl (open circles), 0.05M NaCl (solid circles), 0.10M NaCl (solid squares) and 0.15 NaCl (solid triangles)

The results of these measurements are summarized in FIG. 17, showing the PDP values obtained for each time point and added NaCl concentration: 0M ("control," open circles); 0.05M (solid circles); 0.1M (solid squares); 0.15M (solid triangles). Clearly, there is a graded, accelerated increase in the PDP values resulting from increasing concentrations of added NaCl. The higher the level of applied stress, the faster the onset of significant oil droplet coalescence. At the highest level of stress—i.e., 0.15M added NaCl—there was virtually a doubling of the PDP at the earliest time point, t≈0, meaning that there was already significant destabilization of the sample over the short time—just 5 min, or so—needed to complete the PSD measurement. It is clear that by a judicious choice of stress level—i.e., the concentration of added NaCl—this sample can be made to reveal its degree of underlying instability in a much shorter period of time than is required in the absence of quantifiable stress (i.e., >20 hrs, FIG. 16).

The observed dependence of the computed PDP on elapsed time and salt-stress level, [NaCl], for the vegetable fat emulsion with added destabilizing mixed ionic species (shown in FIG. 17) is summarized in Table II. The results of linear regression analyses performed on the PDP vs t data for each value of [NaCl] are also summarized in Table III. Nearly ideal values of the correlation coefficient, r, are obtained for all of the stress levels, [NaC]. Specifically, r=0.958, 0.980 and 0.973 for [NaCl]=0.05M, 0.10M and 0.15M, respectively (bold type in Table III). The indicated slope values associated with each value of [NaCl] again provide a useful quantitative measure of the extent of instability, or inferiority, of the vegetable fat emulsion in the presence of the mixed ionic species. As before, it would be useful to divide the increase in slope (i.e., relative to the control sample) by the concentration of added [NaCl], in order to arrive at a quantitative measure of the instability induced in the sample by application of a given stress level. The fact that all of the r-values are so close to unity for all three values of [NaCl] again reinforces the predictive value of the accelerated stress-testing method outlined in the present invention and ratifies conclusions of instability drawn for this sample. This vegetable fat emulsion was already observed to become unstable after ≈20 hours due to the addition of mixed ionic species, as seen in FIG. 16 and discussed earlier. The systematic addition of significant, different amounts of NaCl served its intended function—i.e., acceleration of the onset of reproducible instability of the dispersion.

In the third experiment, the mixed ionic species (same concentration) were again added to four separate aliquots, or batches, of the same vegetable oil emulsion (5% w/v), to form the same "baseline" dispersion utilized in the previous experiment. At the same time (t≈0) the batches were systematically stressed by the addition of acid (i.e. pH reduction), similar to the technique that was utilized in one of the milk stability studies, discussed earlier. This time, however, hydrochloric acid (HCl) was added to the batches in increasing proportions, in order to reduce the pH of the final dispersions in successive stages. The vegetable oil droplets comprising the starting emulsion were stabilized by a lecithin surfactant, having an isoelectric point (pH) of ≈3.2. This dispersion, stabilized by an anionic surfactant that induces a net negative charge under low acid conditions, was stressed by addition of acid, causing a reduction in the electrostatic charge residing on the finely dispersed milk droplets, thus inducing agglomeration. The pH of the unstressed starting sample was 6.56. The addition of increasing amounts of acid stress to the batches of emulsion (containing the usual destabilizing mixture of ionic species), equivalent to HCl concentrations of approximately 0.006M (0.228 g/L), 0.012M (0.456 g/L) and 0.025M (0.912 g/L), produced final pH values of 5.65, 5.13 and 4.46, respectively in these samples The charge on the oil droplets thus dropped successively. The final pH values of the resulting acid-stressed samples were: batch #1("control"), pH=6.56; batch #2, pH=5.65; batch #3, pH=5.13; batch #4, pH=4.46. As in the previous experiment, each batch was assessed by measuring the PSD at five different time points: t=0, 60, 120, 180 and 240 minutes (approximate times). As before, this study was designed to accelerate the onset of significant, measurable oil droplet coalescence. The volume-weighted PDP computations for each calcium-stressed sample were appropriately adjusted to the new final lipid concentration at baseline.

Figure 18:
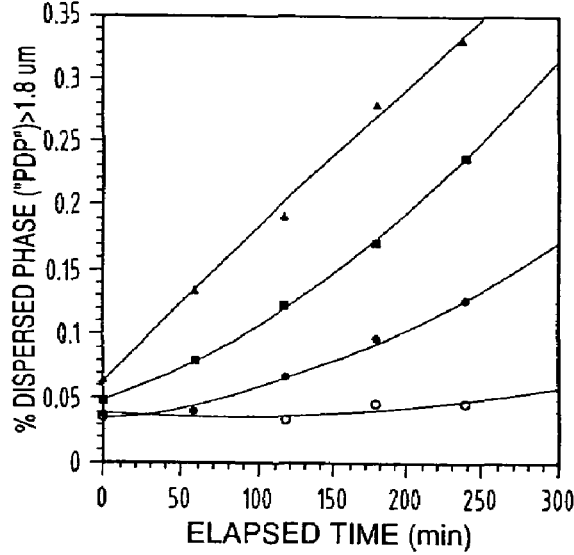
FIG. 18 shows the PDP (d>1.8 μm) vs elapsed time obtained for the vegetable oil emulsion of FIG. 16 after the addition (t=0) of mixed ionic species and application of acid stress: pH 6.56, control (open circles), pH 5.65 (solid circles), pH 5.13 (solid squares) and pH 4.46 (solid triangles)

The results of these measurements are summarized in FIG. 18, showing the PDP values for each time point and reduced pH value: pH=6.56 ("control," open circles); pH=5.65 (solid circles); pH=5.13 (solid squares); pH=4.46 (solid triangles). The PDP plots shown in FIG. 18 resemble those seen in FIG. 17, obtained from NaCl stressing of the dispersion containing vegetable oil emulsion plus mixed ionic species. There is a graded, accelerated increase in the measured PDP values with decreasing pH. The acceleration in the time frame needed to establish the extent of instability of the dispersion is similar to that which was obtained from NaCl stressing of the dispersion. The greater the level of applied stress, the faster the onset of significant oil droplet coalescence. At the highest level of stress, pH=4.46, there was more than a 50% increase in the PDP value at the earliest time point, t≈0. Once again, the sample had become significantly destabilized over the short time—5 min, or so—needed to complete the PSD measurement. As before, by a judicious choice of stress level—in this case, a reduction in pH due to added HCl—this dispersion could be forced to reveal its degree of underlying stability in a much shorter period of time than was required in the absence of quantifiable stress.

The observed dependence of the computed PDP on elapsed time and acid-stress level (pH) for the vegetable fat emulsion with added destabilizing mixed ionic species (shown in FIG. 18) is summarized in Table IV. The results of linear regression analyses performed on the PDP vs t data for each value of pH are also summarized in Table IV. Again, nearly ideal values of the correlation coefficient, r, are exhibited for all of the acid-stress (pH) levels. Specifically, r=0.972, 0.987 and 0.996 for pH=5.65, 5.13 and 4.46, respectively (bold type in Table IV). The indicated slope values associated with each value of pH again provide a useful quantitative measure of the extent of instability, or inferiority, of the vegetable fat emulsion in the presence of the mixed ionic species. As before, it would be useful to divide the increase in slope (i.e., relative to the control sample) by the change in pH (ΔpH), in order to arrive at a quantitative measure of the instability induced in the sample by application of a given stress (pH) level. The fact that all of the r-values are so close to unity for all three values of reduced pH again reinforces the predictive value of the accelerated stress-testing method outlined in the present invention and ratifies the conclusion of instability drawn for this sample. The systematic addition of significant, increasing amounts of acid served its intended function—i.e., acceleration of the onset of reproducible instability of the dispersion.

The experiments reviewed above, in which specific, well-defined stress factors were applied systematically to two different charge-stabilized emulsions and the "percent dispersed phase," or PDP, determined by a sensitive and quantitative means, as a function of elapsed time, form the basis for three preferred embodiments of the method of the present invention. Each embodiment described below centers on the systematic application of a different, specific stress factor to the dispersion sample of interest, for the purpose of evaluating its stability on an accelerated basis.

Figure 19:
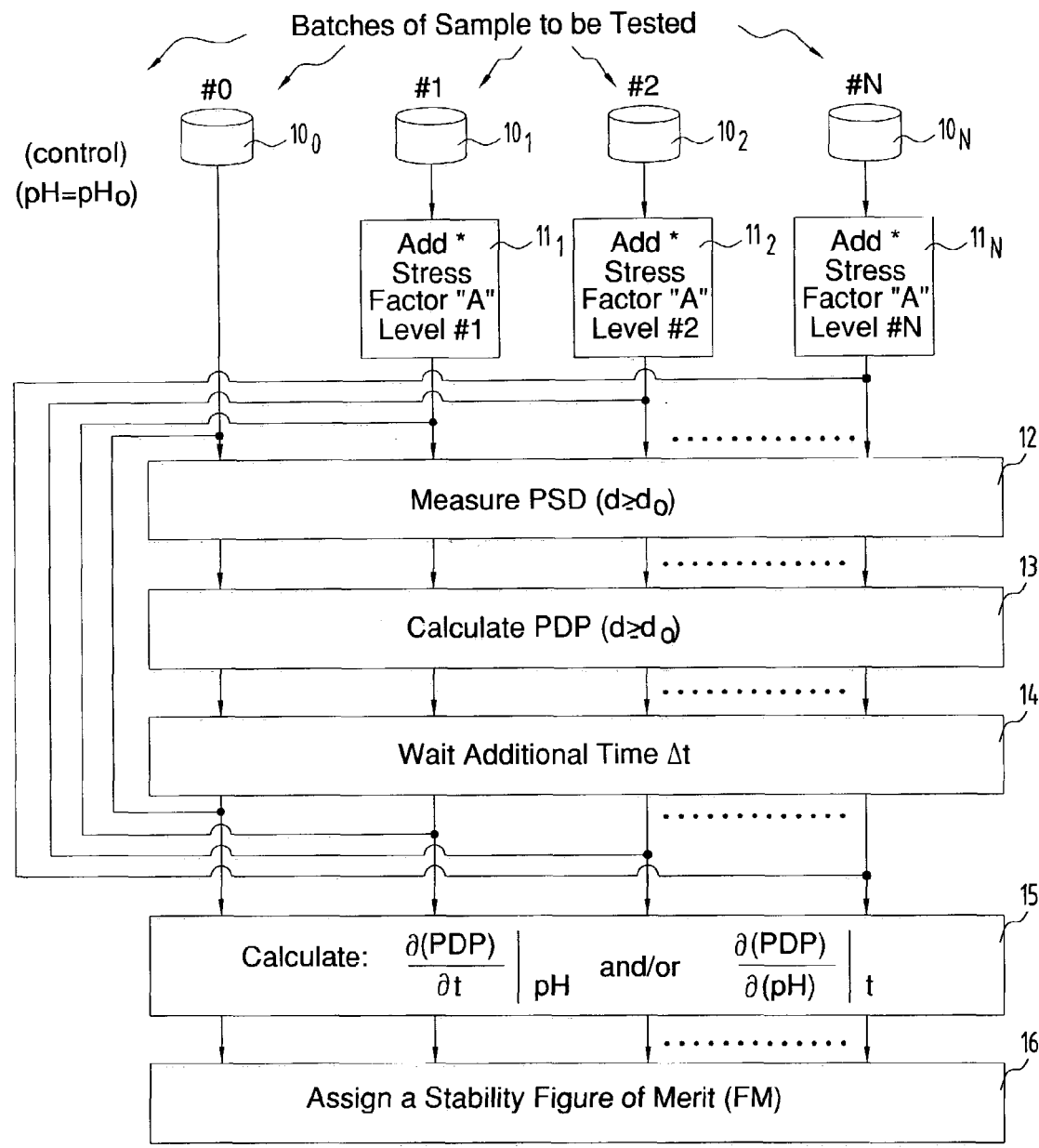
FIG. 19 shows schematically the first embodiment of the method of this invention of accelerated determination of the stability of a dispersion or emulsion, through systematic application of stress factor "A," consisting of adding acid or base to the sample (whichever is appropriate), causing the net charge on the particles to decrease.

The first embodiment of the method of this invention, shown schematically in FIG. 19, utilizes stress factor "A," consisting of controlled alteration of the pH—i.e., involving either an increase or a decrease in the pH of the continuous phase of the dispersion or emulsion in question. In this embodiment, stressing of the starting sample by means of changing its pH causes the average amount of charge on the surfaces of the particles (or droplets) to decrease, resulting in a reduction in the interparticle potential energy barrier height, $V_{MAX}$, and a consequent acceleration in the rate of irreversible agglomeration of neighboring particles (or coalescence of neighboring droplets). The choice of whether to increase or decrease the pH of the sample depends on whether the particles (or droplets) carry a net negative or positive charge in their normal, unperturbed state. If the pH of the unperturbed dispersion is greater than the "isoelectric point," or IEP (i.e., the pH value at which the charge on the particles is approximately zero), the particles carry a net negative charge. In this case, the stress factor consists of lowering the pH of the sample by one or more predetermined increments. This systematic titration is accomplished by adding one or more measured amounts of concentrated acid (either in "pure" or buffered form) to the starting sample.

Each resulting reduction in the pH value brings the dispersion closer to its IEP, with a corresponding reduction in the average charge on the particles or droplets, thus resulting in a correspondingly greater propensity for particle agglomeration or coalescence.

Conversely, if the pH of the starting dispersion is lower than the IEP, the particles carry a net positive charge. In this case, the stress factor consists of raising the pH of the dispersion by one or more predetermined increments, through the systematic addition of concentrated base (again, either in pure or buffered form). Each increase in the pH value brings the dispersion closer to its IEP, ultimately achieving the same result obtained by adding acid to a dispersion containing negatively charged particles—i.e., the dispersion is progressively "pushed," on an accelerated basis, toward instability, manifested by more rapid particle agglomeration or coalescence.

As shown schematically in FIG. 19, the starting dispersion or emulsion to be tested is divided into N+1 separate aliquots, or batches, $10_0$, $10_1$, $10_2$ ... $10_N$, with $N \geq 1$. Each aliquot contains either the same sample volume or, possibly, a different volume, depending on the specific design of the stability test. The sample aliquot referred to as $10_0$ constitutes the "control" for the stability test, as it is not subjected to any (acid or base) stress. Inclusion of this control sample in the test protocol is not strictly required. However, given the variability in sample composition that often occurs from one manufacturing period to another, it is usually desirable to include in the testing procedure a sample that has not been stressed. In this way, the ability of the new accelerated stress testing method to detect reliably small changes in particle agglomeration is potentially enhanced and speaks to the quality of the individual batch.

At the start of the accelerated stress test, referred to hereinafter as t=0, a specific amount of acid or base is added to the N=1 sample aliquot at $11_1$. In cases in which acid stress is appropriate, the pH of the dispersion is therefore reduced from its starting value (i.e., that of the control sample), $pH_0$, by a given (usually, but not necessarily, predetermined) increment, $\Delta pH_1$, resulting in a new value, $pH_1 = pH_0 - \Delta pH_1$. This new, lower value is ideally measured, but can be calculated (based on the volume of the sample aliquot and the volume and pH of the concentrated acid or buffer that is used to effect the reduction in pH) after addition of the stress factor. Alternatively, in the case in which an increase in the pH of the starting dispersion by an increment $\Delta pH_1$ is appropriate, affected by the addition of base, the resulting pH of the dispersion can be expressed as, $pH_1 = pH_0 + \Delta pH_1$.

As indicated schematically in FIG. 19, stress factor "A," consisting of the addition of acid or base (whichever is appropriate), is applied to N distinct (ideally identical) aliquots at $11_1$, $11_2$, ... $11_N$ of the dispersion to be tested. In some cases, the dispersion in question may be so relatively well characterized and/or predictable (e.g., during routine monitoring of a well-behaved manufacturing process) that only a single level of stress—i.e. $\pm \Delta pH_1$—need be applied in order to determine its stability, or lack thereof. In such cases, N=1 will suffice. However, when new or modified products are evaluated, at least two (i.e., $N \geq 2$) levels of increasing stress should be applied to the starting dispersion, as shown by the various examples described herein, in order to obtain a set of self-consistent PDP results, potentially yielding greater accuracy and reliability. At the very least, the application of additional increments of stress—i.e., $\pm \Delta pH_I$, where I=1, 2, ..., N—may result in greater reliability in the resulting PDP measurements, and hence greater confidence in the conclusions regarding sample stability. In general, if N different levels of stress factor "A" are applied to the dispersion, the resulting values of pH for the N stressed sample aliquots can be described by: $pH_I = pH_0 - \Delta pH_I$, in the case of acid stress, or $pH_I = pH_0 + \Delta pH_I$, in the case of base stress, where I=1, 2, ..., N and $\Delta pH_1 < \Delta pH_2 < ... < \Delta pH_N$ Following application of the N different acid or base stresses to the starting sample aliquots, the particle size distributions (PSDs) for each, as well as for the unstressed control (#0) sample, are measured at 12, using a technique for particle size analysis that possesses adequate sensitivity and resolution. For the reasons already discussed above, the technique of SPOS, typically based on the principle of light extinction (LE), but optionally based or light scattering (LS), or a combination of the two ("LE+LS"), depending on the type of emulsion or dispersion to be evaluated, is preferred. In this case, the measured PSD typically relates to a range of particle diameters, $d \geq d_0$, which defines the "tail" of largest particles comprising the PSD. The threshold value, $d_0$, is chosen to maximize the statistical significance (i.e., signal/noise ratio) of the resulting PSD, based on the desired maximum analysis time and extent of sample dilution. Typically, the measurement of the PSD for each sample aliquot is carried out immediately (i.e. as quickly as possible) following the application of the acid or base stress factor. However, in some instances it may be desirable to wait a particular length of time after applying the stress factor to a particular sample before commencing measurement of the PSD. Depending on the complexity of the apparatus used to perform the stress testing, the PSDs may be measured serially, one sample aliquot after another, or in parallel, using several independent sensors and associated instrumentation to perform each SPOS measurement at substantially the same time.

Immediately following a measurement of the PSD ($d \geq d_0$) for each sample aliquot, the "percent dispersed phase," or PDP (typically also for $d \geq d_0$), for each sample, corresponding stress level ($\Delta pH_I$) and elapsed time is calculated at 13 from each measured PSD. Following this step, a time delay, $\Delta t$, at 14 is allowed to occur for each sample, following which the PSD is again measured, and the corresponding PDP value calculated, for each sample. The time delay, $\Delta t$, is typically chosen to be substantially the same for all samples, but this is not a requirement. Optionally, it may be chosen to be different for one or more samples, depending on the levels of acid or base stress chosen. Alternatively, depending on the time needed to perform the PSD measurements for the entire set of sample aliquots and the characteristic time of accelerated particle agglomeration resulting from the various applied stress levels, the nominal time delay between successive sets of PSD measurements may be chosen to be zero. In the latter case, measurement of the PSDs and calculation of the PDP values for the set of sample aliquots effectively becomes a continuous process, without significant idle periods between successive sets of measurements.

The repetitive cycles of PSD measurements and corresponding PDP calculations for the set of acid- or base-stressed sample aliquots (including the unstressed, control sample) are carried out for a long enough time to permit reliable determination of the PDP as a function of elapsed time for each applied stress level. The presumption is that the levels of applied stress have been chosen judiciously, so that significant increases in the PDP values are observed after the desired, relatively short period of time, for at least the highest level of stress (i.e., the largest $\Delta pH_I$). The number of measurement and calculation cycles is typically predetermined, especially in the case of a dispersion that has been well characterized in the past with respect to stability and performance. Alternatively, for dispersions that are relatively new and "unknown" with respect to stability and quality, the number of measurement cycles, and therefore the overall duration of accelerated stress testing, may be "open-ended." In this case, the procedure is terminated only after sufficient time has elapsed to permit reliable determination of changes in the PDP values for one or more levels of applied (acid or base) stress. If meaningful changes in the PDP values are not observed at even the highest-level(s) of applied stress following a reasonable length of time, the procedure would typically be repeated using a new set of higher stress levels, $\Delta pH_I$.

From the procedure described above, a set of PDP values ($d \geq d_0$) as a function of pH and time, t, are obtained. From these PDP values, at least two potentially useful quantities, or sets of quantities, can be derived at 15. The first of these is the rate of change of the PDP with elapsed time, t, for each given pH value, $\partial(PDP)/\partial t|_{pH}$. The value of this partial derivative is computed separately for each level of applied (acid or base) stress, $pH_1$, i.e., for $pH_1$, $pH_2$, ... $pH_N$. Values for this "slope," obtained by linear regression analysis of the PDP vs t data for each value of pH, are shown in Table I for the three samples of whole milk and Table IV for the vegetable fat emulsion discussed above. In the case of the acid-stressed milk samples, the PDP was either substantially constant with increasing time, in the case of samples "0608" and "0615," or increased linearly with time, in the case of sample "0612," for both $pH_1$=6.1 (FIG. 6) and $pH_2$=5.7 (FIG. 7). The "slope," $\Delta(PDP)/\Delta t$, obtained by linear regression analysis was 0.00204 for $pH_1$=6.1 and 0.000260 for $pH_2$=5.7.

In the case of the vegetable fat emulsion (plus mixed ionic species), also discussed above, there was a modest amount of curvature observed in the plots of PDP vs t for certain values of reduced pH associated with applied acid stress (FIG. 18). In that case, the value of $\partial(PDP)/\partial t$ depended not only on the value of pH (i.e., increasing as the latter decreased), but also to a modest extent on the value of t. In any event, for all pH values employed, the degree of curvature in PDP vs t was small enough to permit a linear approximation, allowing the slope, $\Delta(PDP)/\Delta t$, to be characterized by a single value for each value of $pH_1$. As shown in Table IV, the value of the slope increased progressively, from 0.00037 to 0.00072 to 0.00099, when the pH was reduced from 5.65 to 5.13 to 4.46, respectively. (The slope was negligible, 0.00003, for the control sample, pH=6.56.)

There is another quantity that can be derived from the set of PDP values—the increase in the PDP per unit change of pH, for a given value of elapsed time, t, written as $\partial(PDP)/\partial(pH)|_t$. The value of this partial derivative can be computed for various increasing values of elapsed time (interpolating between the actual experimental times, if necessary, to obtain PDP values for each desired t value). The value of $\partial(PDP)/\partial(pH)$ for a given value of t will generally depend on pH—i.e., the PDP will not necessarily increase linearly with increasing (or decreasing) pH. However, it is convenient to use a linear approximation to describe the change in the PDP with the change in stress level (i.e., $\Delta pH$), in which case the "slope" can be approximated by $\Delta(PDP)/\Delta(pH)$ for each value of t. Of course, this slope will in general increase with increasing time, t, given a positive slope for $\partial(PDP)/\partial t|_{pH}$. For example, in the case of the data generated from the acid-stressed milk batch 0612 (Table I), the slope $\Delta(PDP)/\Delta(pH)$ associated with a decrease in pH from 6.6 to 6.1 (i.e., $\Delta pH$=−0.5) increases with time as follows: 0.07 (80 min), 0.48 (160 min) and 0.85 (240 min). The corresponding computed values of the slope based on a decrease in pH from 6.6 to 5.7 (i.e., $\Delta pH$=−0.9) are 0.17 (80 min), 0.41 (160 min) and 0.62 (240 min). In the case of the acid-stressed vegetable fat emulsion (Table IV), the slope $\Delta(PDP)/\Delta(pH)$ associated with a decrease in pH from 6.56 to 5.65 ($\Delta pH$=−0.91) increases with time as follows: −0.001 (60 min), 0.040 (120 min), 0.058 (180 min) and 0.087 (240 min). The corresponding values of the slope based on a decrease in pH from 6.56 to 5.13 ($\Delta pH$=−1.43) are 0.028 (60 min), 0.064 (120 min), 0.089 (180 min) and 0.134 (240 min). Finally, the values of the slope based on a decrease in pH from 6.56 to 4.46 ($\Delta pH$=−2.1) are 0.046 (60 min), 0.076 (120 min), 0.112 (180 min) and 0.135 (240 min). Hence, for this dispersion, the slope $\Delta(PDP)/\Delta(pH)$ increases with increasing $\Delta pH$ for all values of elapsed time.

In concluding the discussion of the first embodiment, what remains is the assignment of a "figure of merit" at 16 for the dispersion being investigated, so that its stability can be characterized quantitatively and compared to other examples of the same dispersion, or to other products altogether. Perhaps the simplest and most straightforward way of defining a figure of merit, or FM, for the sample is to use the computed value of $\partial(PDP)/\partial t|_{pH}$. Stable dispersions will yield relatively small values of $\partial(PDP)/\partial t|_{pH}$, while inferior dispersions will yield relatively large values of this parameter, for a given stress level, $\Delta pH$. The value of $\partial(PDP)/\partial t|_{pH}$, obtained after the pH of the dispersion has been changed by a given amount, $\Delta pH_1$, describes how quickly the dispersion undergoes irreversible agglomeration, owing to the change in pH. The stability of the starting sample, before acid or base stressing, can therefore be "graded," based on this value. The larger the value of $\partial(PDP)/\partial t|_{pH}$, for a given increment in $pH_1$ (i.e., $\Delta pH_1$), the less stable is the starting sample.

Alternatively, the sensitivity of the PDP values to changes in pH after a given elapsed time can be used to assess the stability of the starting sample. That is, the FM can be defined using the computed value of $\partial(PDP)/\partial t|_{pH}$, for a given value of elapsed time, t (assuming that the latter is sufficiently long to permit the accelerated instability to assert itself). The larger the value of $\partial(PDP)/\partial(pH)|_t$ for a given value of elapsed time, t, and relatively small value of applied stress, $\Delta pH_I$, the less stable is the starting sample. The sensitivity of the dispersion to a given change in pH can be used to determine the optimal stress level, or range of stress levels, for performing accelerated stress testing.

In summary, there are at least two simple ways to define a figure of merit a dispersion of interest. These are: 1) measuring the change in the PDP with respect to elapsed time, for a given stress level, $\Delta pH_I$; and 2) measuring the change in the PDP with respect to pH, for a given elapsed time, t. While the resulting values can be considered separately, they might also be combined (linearly or nonlinearly), to form yet a third value, derived from the first two. One or another of these computed or derived values can be compared usefully with "benchmark" values, obtained previously for successful examples of the same manufactured product, or for other, comparable products. Such comparisons provide the means for determining whether the product in question is sufficiently stable to permit its, continued manufacture, distribution and use, or whether key aspects of the manufacturing process (including the quality of raw input materials) require improvement or modification whether used individually or as an entire set of values (i.e., incorporated into an appropriate algorithm), provide the means for assigning one or more measures of the FM for the dispersion, and hence assessing its stability.

Figure 20:
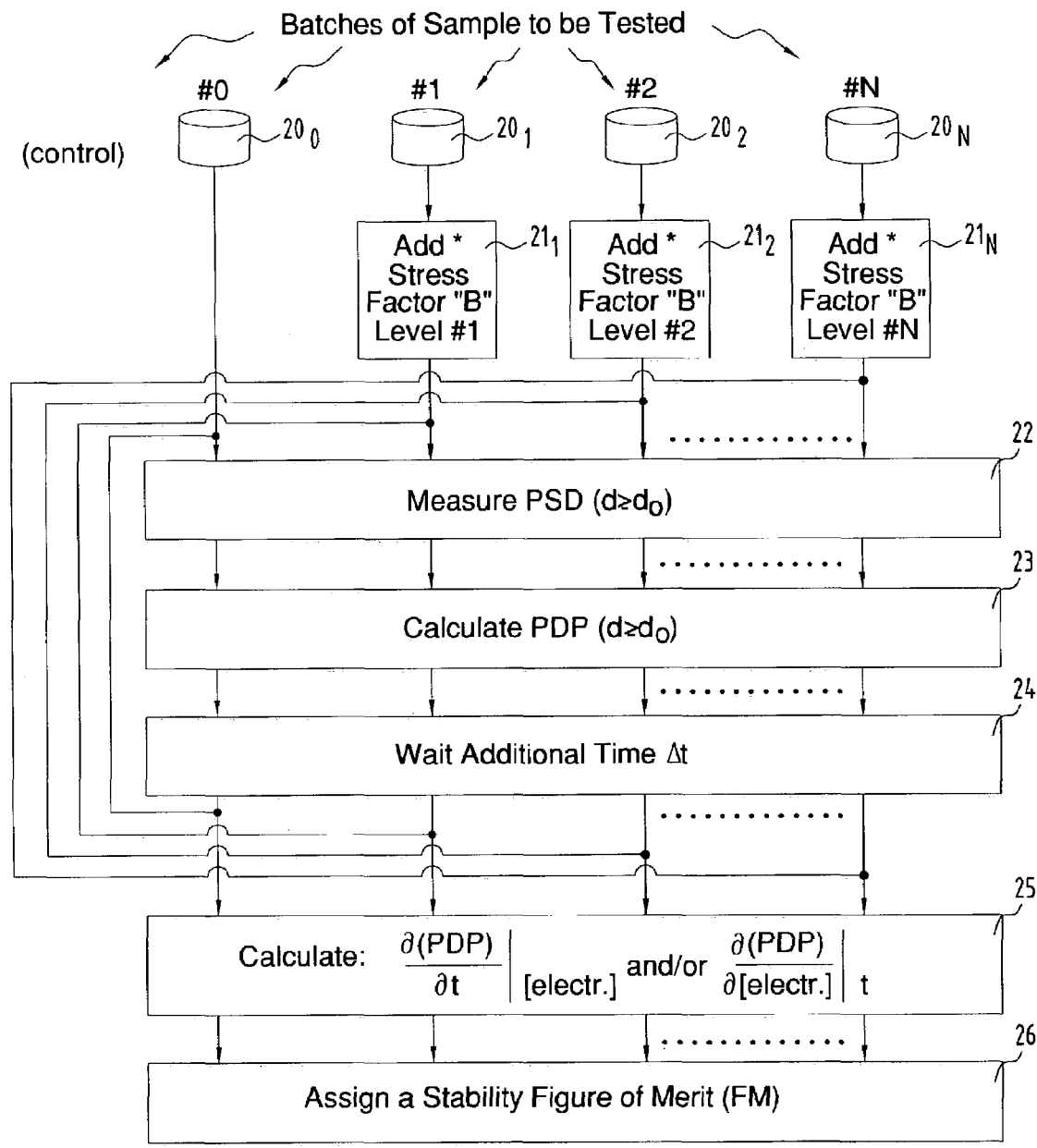
FIG. 20 shows schematically the second embodiment of the method of this invention of accelerated determination of the stability of a dispersion or emulsion, through systematic application of stress factor "B," consisting of adding specific electrolyte, containing adsorbing ions, to the sample, causing the net charge on the particles to decrease.

The second embodiment of this invention, summarized schematically in FIG. 20, is the same as the first embodiment in all respects but one. The only difference is that it utilizes a different stress factor, labeled "B," consisting of the controlled, systematic addition of a particular electrolyte which, after dissociation, supplies ions that are (partially) adsorbed by the charged particles in the dispersion or emulsion of interest. Adsorption of the charged ions by the oppositely charged particles or droplets causes the average charge on their surfaces to be decreased. The greater the concentration of added electrolyte, the greater the average number of charged ions that are adsorbed onto the charged surfaces of the particles or droplets, and the lower the resulting net charge on the latter. The net effect of stressing the dispersion in this way is similar to the effect achieved by stressing it through a decrease or increase of pH, as provided by the first embodiment. The mechanism for achieving this charge reduction is quite different in each of the two embodiments, but the net effect, qualitatively speaking, is the same. As in the first embodiment, this reduction in charge causes a reduction in the interparticle potential energy barrier height, $V_{MAX}$, and, therefore, an acceleration in the rate of irreversible agglomeration of neighboring particles/droplets in the dispersion or emulsion. It should be noted that the addition of adsorbing electrolyte to the charge-stabilized dispersion of interest has a second destabilizing influence on it. The resulting introduction of mobile ions (both positive and negative) into the continuous phase of the dispersion results in a partial screening of the electrostatic repulsive force between neighboring particles. This action causes a reduction in the interparticle potential energy barrier height, independent of the reduction caused by the reduced charge on the particles caused by adsorbing ions. This screening effect is the subject of the third embodiment, discussed below.

There are two choices that must be made in implementing the second embodiment for accelerated stress testing of the dispersion or emulsion of interest. First, a suitable electrolyte must be selected—i.e., one that, after dissociation, provides ions that are adsorbed to a significant extent by the surfaces of the oppositely charged particles/droplets. In the case of the stress tests performed on the milk samples, discussed above, calcium chloride proved to be a good choice for the electrolyte, as the dissociated $Ca^{++}$ ions obviously have an affinity for the (bovine) casein-coated fat droplets comprising the dispersed phase of whole milk. Typically, a variety of electrolytes are suitable candidates for stressing dispersions of interest, providing ions that adsorb to some extent onto the charged particles/droplets. A second choice that must be made, of course, is the appropriate range of concentration for the added electrolyte, once the latter has been selected. Estimates can be made based on theoretical considerations (i.e., using models for selective ion adsorption, together with numerical predictions of DLVO theory). Alternatively, and more typically, the range of suitable concentrations can be determined by trial and error, through stress testing of the dispersion of interest.

As seen in FIG. 20, the same procedures used in the first embodiment are also utilized in the second embodiment batches, or aliquots, of the sample are provided at $20_0$, $20_1$, $20_2 \ldots 20_N$. The only difference is in the nature of the stress factor that is applied to the N separate aliquots of the starting sample at $21_1$, $21_2 \ldots 21_N$. Different amounts of a stock solution (i.e. of given concentration) of the chosen electrolyte are added to each aliquot of starting sample at t=0 (nominal "start"), thereby establishing different, desired concentrations of the adsorbing ions (together with their counter-ions) in each of the sample aliquots, $[electr]_1$, $[electr]_2, \ldots, [electr]_N$. Following application of the stress factors to the N sample aliquots (with a control sample #0 also established, without added electrolyte), the set of procedures comprising each cycle of stress testing is the same as that described above for the first embodiment. These are (for each sample aliquot, including the control): 1) measurement of the PSD ($d \geq d_0$) at 22, using a suitable technique for particle size analysis, preferably SPOS-LE; 2) calculation of the PDP at 23 (typically also $d \geq d_0$); 3) optionally allowing at 24 a time, $\Delta t$ (typically, but not necessarily, substantially the same for each aliquot), to elapse before the next cycle of PSD measurement and PDP calculation commences.

As in the first embodiment, the set of PDP values obtained for the N different levels of applied stress—i.e. the various concentrations of added electrolyte, $[electr]_1$,—and the various elapsed times give rise to quantities that describe the sensitivity of the dispersion to the applied stress factor. These quantities can be used to assess the stability of the dispersion or emulsion of interest. The first of these at 25 is the rate of change of the PDP with elapsed time, t, for a given concentration of added electrolyte, [electr], written as $\partial(PDP)/\partial t|_{[electr]}$. The value of this partial derivative is computed separately for each level of applied absorbing-electrolyte stress, $[electr]_i$, i.e., for $[electr]_1$, $[electr]_2$, ..., $[electr]_N$. Values for this "slope," obtained by linear regression analysis of the PDP vs t data for each value of $[CaCl_2]$, are shown in Table II for the three samples of whole milk discussed above. The PDP was substantially constant with increasing time for samples "0608" and "0615" at the lowest stress level, $[CaCl_2]=0.005M$. The PDP increased linearly with time for sample "0612," for both $[CaCl]=0.005M$ and $0.01M$ (FIG. 11). The slope, $\Delta(PDP)/\Delta t$, obtained by linear regression analysis was 0.00023 for $[CaCl_2]=0.005M$ and 0.00038 for $[CaCl_2]=0.01M$. The PDP also increased substantially linearly with time for sample "0608" at the highest stress level, $[CaCl_2]=0.01M$, with a slope of 0.00043.

There is another quantity that can be derived from the set of PDP values—the increase in the PDP per unit increase in electrolyte concentration, [electr], for a given value of elapsed time, t, written as $\partial(PDP)/\partial[electr]|_t$. Its value is computed for each value of elapsed time (interpolating between the experimental times, if appropriate and necessary) and will generally depend on [electr]—i.e., the PDP will not necessarily increase linearly with increasing [electr]. However, it is convenient to use a linear approximation to describe the change in the PDP with the change in stress level (i.e., [electr]), in which case the "slope" can be approximately by $\Delta(PDP)/\Delta[electr]$ for each value of t. Of course, this slope will in general increase with increasing time, t, given a positive slope for $\partial(PDP)/\partial t|_{[electr]}$. For example, in the case of the calcium chloride-stressed milk batch 0612 (Table II), the slope $\Delta(PDP)/\Delta[electr]$ associated with $[CaCl_2]$ 0.005 can be calculated from the available data and increases with time as follows: 40 (80 min), 19 (160 min), 23 (240 min) and 55 (660 min). The corresponding computed values of the slope associated with $[CaCl_2]=0.01M$ are 44 (80 min), 43 (160 min), 42 (240 min) and 64 (660 min).

As in the first embodiment, the computed values of the partial derivatives relevant to the adsorbing-electrolyte stress utilized in the second embodiment—i.e., $\partial(PDP)/\partial t|_{[electr]}$ and $\partial(PDP)/\partial[electr]|_t$—can be used at 26 to establish a figure of merit for the dispersion of interest. If the quantity $\partial(PDP)/\partial t|_{[electr]}$ is used to define the FM, it should be clear that stable dispersions will yield relatively small values of this parameter, while inferior dispersions will yield relatively large values, for a given stress level, [electr]. Alternatively, the FM can be defined using the computed value of $\partial(PDP)/\partial[electr]_1$, for a given value of elapsed time, t. Which of these derivative quantities are used, whether singly or in combination with each other (by means of a suitable algorithm), depends on the dispersion being investigated and the type (and concentration range) of the electrolyte stress factor employed. In the case of the calcium chloride stressed milk samples discussed above, the PDP for sample "0608" (FIG. 10) was substantially constant with time for $[CaCl_2]$=0.005M, but showed a modest linear increase for $[CaCl_2]$=0.01M. The PDP for the sample identified as inferior, "0612" (FIGS. 11 and 13), already showed a small increase with time for $[CaCl_2]$=0.005M, and a large, nonlinear and accelerating increase with time for $[CaCl_2]$=0.0M. Finally, the PDP for the youngest, most stable sample, "0615" (FIG. 12), showed, like sample "0608," essentially no change with elapsed time for $[CaCl_2]$=0.005M. However, even for $[CaCl_2]$=0.01M, the PDP showed only a slight increase with time (i.e., much less than found for sample "0608"). Clearly, use of absorbing Ca++ as a stress factor for the three batches of milk allowed them to be "graded" effectively and unambiguously. The youngest sample, "0615," was the most stable—not surprising, considering its ED; however, the oldest sample, "0608," was the second most stable, while the middle-aged sample, "0612," was revealed to be much less stable than sample "0608"—surprising, given their EDs.

As an aside, it is presumed that the electrolyte chosen for implementation of the second embodiment does not produce ions that adsorb too strongly to the surfaces of the charged particles/droplets. Otherwise, there may be too small a range of concentration of added electrolyte over which the resulting net charge on the particles can be modified, from very little (at lowest [electr]) to maximal (at greatest [electr]). Such compression in the response (i.e. net charge on the particles/droplets) of the dispersion to the application of the stress factor might make it difficult to achieve a linear response in the PDP to changes in electrolyte concentration, elapsed time, or both.

Figure 1:
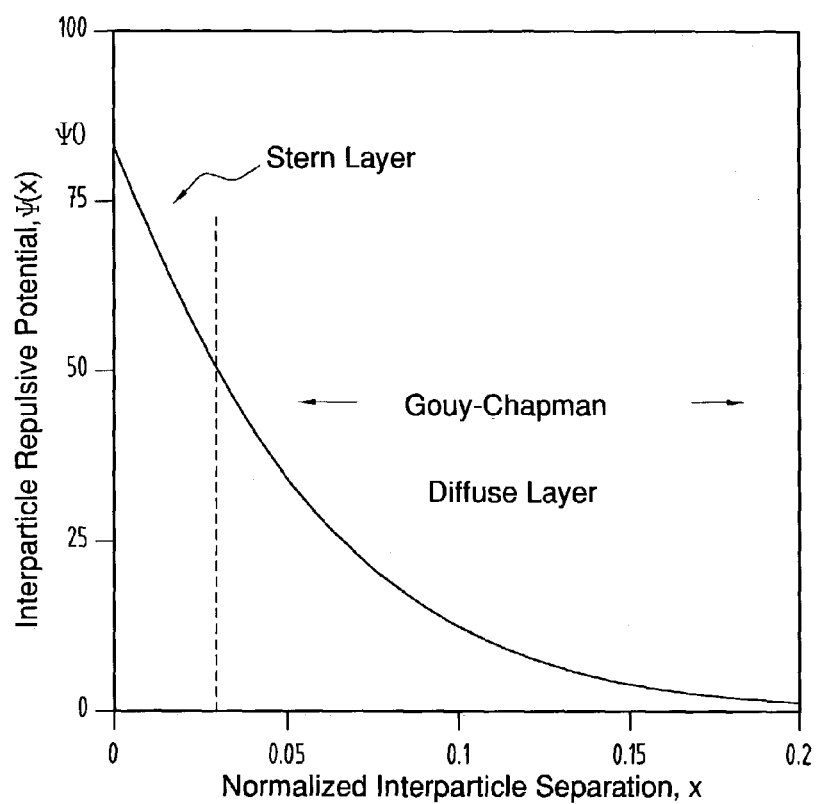
FIG. 1 shows schematically the "electrical double layer," or electrostatic potential energy, as a function of the distance, x, from the surface of a particle, resulting from the charge on the particle (potential $\psi_0$) and mobile charged ions in the aqueous phase.
Figure 21:
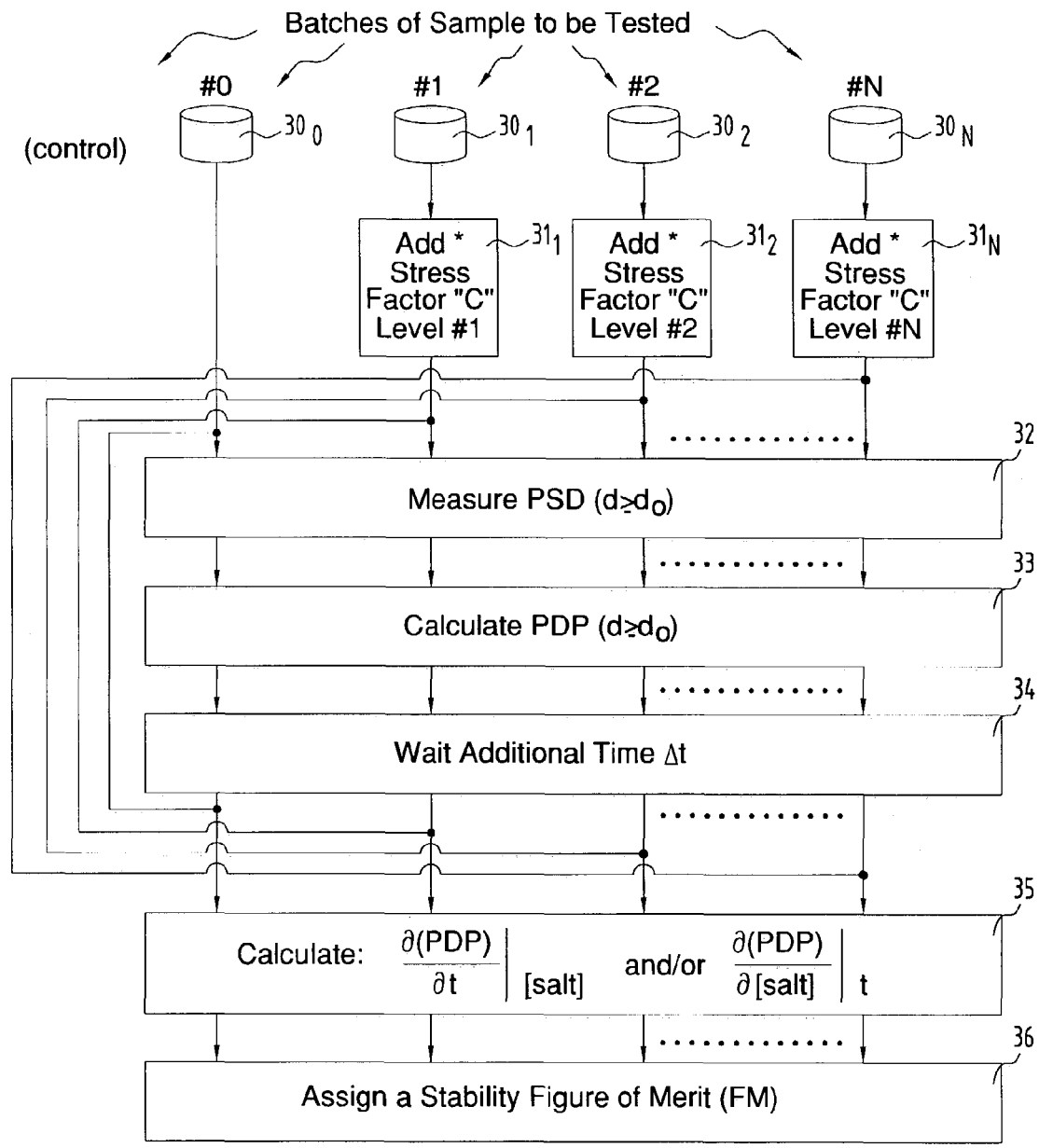
FIG. 21 shows schematically the third embodiment of the method of this invention of accelerated determination of the stability of a dispersion or emulsion, through systematic application of stress factor "C," consisting of adding non-adsorbing salt to the sample, causing the interparticle electrostatic repulsive forces to be reduced.

The third, and final, embodiment of the invention is similar to the second embodiment and is summarized schematically in FIG. 21. Like the second embodiment, it also utilizes added electrolyte—now, however, referred to simply as "salt"—to stress the starting sample. The only difference is that in this case the salt, labeled as stress factor "C," is assumed to be of a type that, upon dissociation, yields charged ions that are not appreciably adsorbed by the charged particles or droplets that comprise the dispersed phase of the dispersion. Rather, the dissociated salt ions remain in the continuous phase of the dispersion, free to diffuse therein. Hence, in this embodiment, the average amount of electrical charge residing on the particles or droplets is substantially unchanged by the addition of different amounts of this salt to aliquots of the starting sample. Therefore, the way in which the added salt reduces the stability of the dispersion (i.e., promoting agglomeration) differs from that achieved in the first and second embodiments, in which interparticle repulsive forces are reduced by decreasing the net charge residing on the surfaces of the particles. Rather, in the present case the interparticle repulsive forces are reduced through the addition of mobile ions in the continuous phase. These ions distribute themselves in thermodynamic equilibrium, in such a way that they serve to "screen," or partially neutralize, the electrostatic fields that emanate from each charged particle. As a result of these added screening ions, the interparticle repulsive potential energy, $V_R(x)$, decays faster with increasing separation, x, between adjacent particles. (See FIGS. 1–3.) That is, the Debye-Hückel inverse screening length, $\kappa^{-1}$, which characterizes the electrical double-layer thickness, decreases. The net result of this increased screening of the repulsive electrostatic fields is a reduction in the interparticle potential energy barrier height, $V_{MAX}$, which serves to destabilize the dispersion.

There are, again, two choices that must be made in implementing the third embodiment. First, a suitable salt must be selected—i.e., one that, after dissociation, provides ions that remain in the aqueous phase of the dispersion under study, largely not adsorbed onto the surfaces of the oppositely charged particles/droplets. (The effectiveness of the dissociated salt ions to shrink the thickness of the electrical double layers associated with each charged particle is also highly dependent on the valence of the ions, as taught by the Debye-Hückel theory.) In the case of the stress tests performed on the vegetable oil emulsion (plus mixed ionic species) discussed above, sodium chloride proved to be a good choice for the added salt. The second choice involves the appropriate range of concentration for the added salt. Again, estimates can be made using DLVO theory. However, typically the range of suitable concentrations is established by trial and error, through stress testing of the dispersion of interest.

As seen in FIG. 21, the same procedures used in the first and second embodiments are also utilized in the third embodiment. A control batch $30_0$ and N additional batches $30_1, 30_2 \ldots 30_N$ are provided. The only difference is in the nature of the stress factor that is applied to the N separate aliquots of the starting sample at $31_1, 32_2 \ldots 31_N$. Different amounts of a stock solution (i.e. of given concentration) of the chosen salt are added to each aliquot of starting sample at t=0 (nominal "start"), thereby establishing different, desired concentrations of the screening ions in each of the sample aliquots. These final concentrations of added salt are referred to as $[salt]_1, [salt]_2, \ldots, [salt]_N$. Following application of the stress factors to the N sample aliquots (with no salt added to the control sample), the set of procedures comprising each cycle of stress testing is the same as that described above for the previous two embodiments. These are (for each sample aliquot, including the control): 1) measurement at 32 of the PSD ($d \geq d_0$), using a suitable technique for particle size analysis, preferably SPOS-LE; 2) calculation at 33 of the PDP (typically also $d \geq d_0$); 3) optionally allowing at 34 a time, $\Delta t$ (typically, but not necessarily, substantially the same for each aliquot), to elapse before the next cycle of PSD measurement and PDP calculation commences.

As in the first two embodiments, the set of PDP values obtained for the N different levels of applied stress—i.e. the various concentrations of added salt, $[salt]_1$,—and the various elapsed times give rise at 35 to calculated quantities that describe the sensitivity of the dispersion to the applied stress factor. That is, these quantities can be used to assess the stability of the dispersion or emulsion of interest. The first of these is the rate of change of the PDP with elapsed time, t, for a given concentration of added salt, [salt], written as $\partial(PDP)/\partial t|_{[salt]}$. The value of this partial derivative is computed separately for each level of applied salt stress, $[salt]_i$, i.e., for $[salt]_1, [salt]_2, \ldots, [salt]_N$. Values for this "slope," obtained by linear regression analysis of the PDP vs t data for each value of [NaCl], are shown in Table III for the vegetable fat emulsion discussed above. There was a modest amount of curvature observed in the plots of PDP vs t for certain values of [NaCl] (FIG. 17). In that case, the value of $\partial(PDP)/\partial t$ depended not only on the value of [NaCl] (i.e., increasing as the latter increased), but also to a modest extent on the value of t. In any event, for all values of [NaCl] employed, the degree of curvature in PDP vs t was small enough to permit a linear approximation, allowing the slope, $\Delta(PDP)/\Delta t$, to be characterized by a single value for each value of [NaCl]. As shown in Table III, the value of the slope increased progressively, from 0.00085 to 0.00152 to 0.00195, when [NaCl] was increased from 0.1M to 0.15M to 0.2M, respectively. (The slope was negligible, 0.000098, for the control sample.)

There is another quantity that can be derived from the set of PDP values—the increase in the PDP per unit increase in [salt], for a given value of elapsed time, $\partial(PDP)/\partial[salt]|_t$. The value of this quantity is computed for each value of elapsed time (interpolating between the experimental times, if necessary). The value of $\partial(PDP)/\partial[salt]$ for a given value of t will generally depend on [salt]—i.e., the PDP will not necessarily increase linearly with increasing [salt]. However, it is convenient to use a linear approximation to describe the change in the PDP with the change in stress level (i.e., [salt]), in which case the "slope" can be approximated by $\Delta(PDP)/\Delta[salt]$ for each value of t. Of course, this slope will in general increase with increasing time, t, given a positive slope for $\partial(PDP)/\partial t|_{[salt]}$. For example, in the case of the sodium chloride-stressed vegetable fat emulsion (plus mixed ionic species) discussed above, the slope $\Delta(PDP)/\Delta[salt]$ associated with [NaCl]=0.1M can be calculated from the data provided in Table III and increases with time as follows: 0.55 (60 min), 0.97 (120 min), 1.63 (180 min) and 2.30 (240 min). The corresponding computed values of the slope associated with [NaCl]=0.15M are 0.49 (60 min), 1.16 (120 min); 1.92 (180 min) and 2.59 (240 min). Finally, the values of the slope associated with [NaCl]=0.2M are 0.85 (60 min), 1.30 (120 min), 2.33 (180 min) and 2.8 (240 min). Hence, for this emulsion the slope $\Delta(PDP)/\Delta[NaCl]$ increases with increasing [NaCl] for all values of elapsed time.

As in the previous embodiments, the computed values of the partial derivatives relevant to the salt-screening stress utilized in the third embodiment—i.e., $\partial(PDP)/\partial t|_{[salt]}$ and $\partial(PDP)/\partial[salt]|_t$—can be used at 36 to establish a figure of merit for the dispersion of interest. If the quantity $\partial(PDP)/\partial t|_{[salt]}$ is used to define the FM, it should be clear that stable dispersions will yield relatively small values of this parameter, while inferior dispersions will yield relatively large values, for a given stress level, [salt]. Alternatively, the FM can be defined using the computed value of $\partial(PDP)/\partial[salt]|_t$, for a given value of elapsed time, t. Which of these derivative quantities are used, whether singly or in combination with each other (by means of a suitable algorithm), depends on the dispersion being investigated and the type (and concentration range) of the salt stress factor employed. In the case of the vegetable oil emulsion (plus destabilizing mixture of ionic species) stressed by sodium chloride, discussed earlier, the PDP (FIG. 17) was found to increase somewhat nonlinearly with time for all three levels of applied stress factor, [NaCl]=0.05M, 0.10M and 0.15M. In all three cases, the evolution of the emulsion toward significant instability (i.e. significant droplet coalescence) was accelerated substantially by the addition of sodium chloride. The larger the level of stress, [NaCl], the greater the absolute extent of droplet coalescence, or PDP value, and the higher the rate of change of the PDP with time, or $\partial(PDP)/\partial t$.

Figure 22:
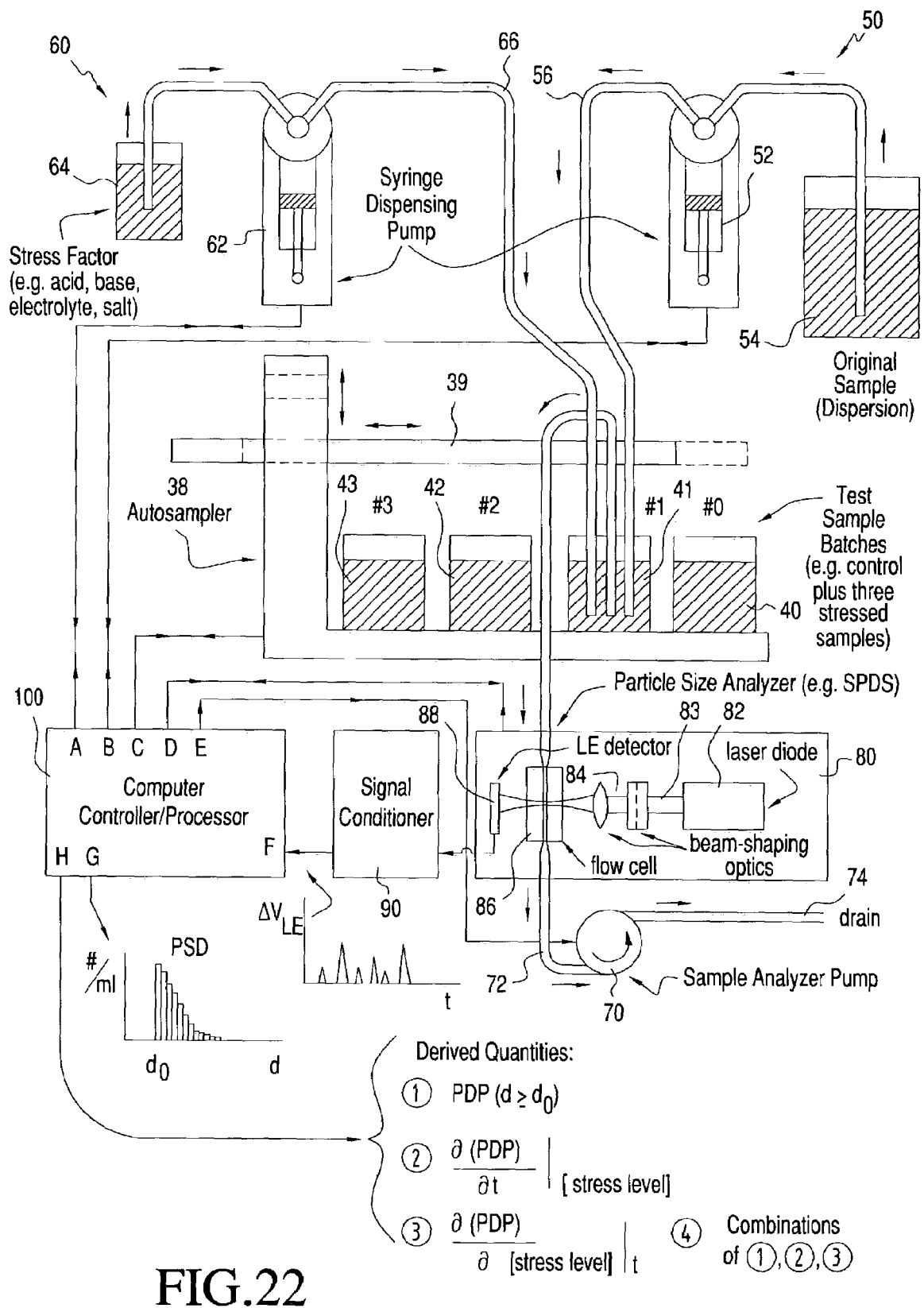
FIG. 22 shows a simplified schematic diagram of a typical apparatus, including a particle size analyzer based on SPOS, that can be used to implement any of the new methods of accelerated determination of the stability of a dispersion or emulsion as described herein.

Implementation of one or more of the methods for accelerated stress testing of sample dispersions, using for example one or more of the embodiments described above, in general requires the use of specialized instrumentation. A simplified block diagram of a typical apparatus that is suitable for implementing any of the three embodiments shown in FIGS. 19–21 is shown in FIG. 22. A computer controlled autosampler means 38 conveniently allows multiple batches of the sample dispersion of interest (having an appropriate, predetermined concentration) to be stress tested. Autosampler means 38 is shown schematically as including a controlled support member 39, which as indicated, can be moved up and down and laterally so that it may move pipes 56 and 66, which, as will be explained below, selectively feed the sample dispersion or emulsion and stress factor to test containers 40, 41, 42, and 43, and move pipe 72 which selectively withdraws the mixture of sample and stress factor from the test containers. In the example shown in FIG. 22, there are four separate batches of sample dispersion, contained in vessels 40, 41, 42, and 43 of appropriate volume. Three of the batches (designated as #1, #2 and #3) are intended to be exposed to a particular chosen stress factor (i.e., acid or base, adsorbing electrolyte or screening salt), and each batch is designed to receive a different stress level (i.e., ΔpH or concentration of [electrolyte] or [salt], respectively). The additional sample batch (designated as #0), to which the stress factor is not applied, serves as the control sample, as described previously.

Two separate fluidics subsystems are shown in FIG. 22. The first fluidics subsystem 50 (upper right-hand corner) employs a fluid dispensing means 52 (e.g., a syringe pump) to deliver a predetermined volume of original sample dispersion of appropriate concentration from a holding vessel 54 through a pipe 56 to the appropriate sample batch vessel 40, 41, 42, or 43 located in the autosampler means. This fluid dispensing means is typically controlled by the same computer controller/processor subsystem 100 that controls the autosampler means and the other subsystems comprising the testing apparatus shown schematically in FIG. 22. The second fluidics subsystem 60 (upper left-hand corner) employs a separate fluid dispensing means 62 (e.g., another syringe pump) to deliver a predetermined volume of fluid comprising the chosen stress factor from a vessel 64 through a pipe 66. As discussed previously, the latter might be relatively concentrated acid or base of a particular molarity and pH (or a particular buffer having a particular composition and pH), or a relatively concentrated electrolyte or salt, or a combination thereof. Each of the fluid dispensing means shown in FIG. 22 is controlled by the same computer controller/processor subsystem 100 that is also used to control and communicate with the other subsystems that comprise the stress testing apparatus. Typically, the desired volume of original sample dispersion fluid is first dispensed into each of the sample batch vessels contained in the autosampler means. The desired (typically much smaller volume) volume of "stress factor" fluid is then dispensed into each of the sample batch vessels (i.e., #1, #2 and #3 in FIG. 22). The volume of stress factor fluid added to each vessel is different, determined by the final pH or electrolyte/salt concentration—i.e., stress level—desired for that particular sample batch. A stirring means (not shown), such as a mechanical propeller, or preferably a magnetic actuated stirring bar, is used to achieve efficient mixing of the original sample dispersion fluid and added stress factor fluid in each vessel during dispensing, thus ensuring homogeneous suspensions in each vessel. The nominal starting time (i.e., t=0) for the accelerated stress testing of each sample batch is established when the stress factor fluid is dispensed into that batch, and this time is recorded by system computer controller/processor 100.

After an appropriate, predetermined time, Δt (FIGS. 19–21), has elapsed, a predetermined quantity of stressed sample dispersion fluid is removed from the desired sample batch vessel and drawn through particle size analyzer subsystem 80 that is utilized to obtain the PSD (d>$d_0$), as described previously. Particle size analyzer 80 is a single particle optical sensor (SPOS) and includes a laser diode 82 which projects a light beam 83 through beam shaping optics 84 and an optical flow cell 86 to a photo detector 88. Particle size analyzer 80 preferably operates on the light extinction (LE) principle, although, as explained above, for certain applications may be of the light scattering (LS) type, or use a combined sensor design LE+LS. In any case, the analyzer provides a particle size distribution (PSD). A suitable pump means 70 (e.g., a third syringe pump), typically located on the "downstream" side of particle size analyzer 80, is used to remove the desired quantity of stressed sample dispersion fluid through pipe 72 from the sample batch vessel to a drain 74. The stressed dispersion to be analyzed is drawn through the optical flow cell 86 at a prescribed flow rate. The total volume of fluid that flows through the cell is determined by the volume originally available in the sample batch vessel (and the anticipated total number of discrete analyses, separated over the total elapsed time of testing) and the desired statistical accuracy of the resulting PSD. The signal produced by particles of appropriate size (i.e., d>$d_0$) that pass through SPOS-type particle size analyzer 80 is, after appropriate conditioning in signal conditioner 90, analyzed using appropriate electronic circuits in computer controller/processor 100 (typically, but not necessarily, the same as the computer that is used to control the other subsystems). As a result, a PSD is obtained, which reveals information about the state of agglomeration of the particles (e.g., those comprising the large-particle "tail" of the PSD).

Predetermined quantities of each of the stressed sample batches, plus (optionally) the unstressed control sample batch, are likewise caused to pass one at a time through the particle size analyzer subsystem 80 at predetermined time intervals following the initial dispensing of the stress factor into each sample batch vessel. By employing separate particle size analyzer subsystems 80 for each batch, the predetermined quantities of each of the sample batches can be fed in parallel at the same time through corresponding particle size analyzer subsystems. As a result, the PSD is obtained for each stressed sample batch at each value of elapsed time, t, for that batch. From each PSD, the value of the PDP (i.e., for d>$d_0$) is further calculated by the system computer, with appropriate corrections made in the final computed PDP values to reflect the addition of different volumes of stress factor fluid(s). The set of results, PDP vs t, thus obtained for each stressed sample batch constitutes the "raw data" for the accelerated stress testing of the sample dispersion of interest, as described earlier. From the set of PDP values, the computer is used to obtain other derived quantities of interest, used to characterize the stability and/or quality of the dispersion, as described above. These include the PDP itself, for any given value of elapsed time, t, and quantities related to the PDP, including, but not limited to, the partial derivatives, $\partial(PDP)/\partial t|_{stress\ level}$ and $\partial(PDP)/\partial[stress\ level]|_t$, as discussed earlier in connection with the three embodiments of the method.

Although autosampler 38 schematically indicates that pipes 56 from pump 52 and pipes 66 from pump 62 may be moved for dispensing original sample or stress factor into a selected vessel 40, 41, 42, or 43, and that a pipe 72 is moved to drain liquid from a selected vessel 40, 41, 42, or 43 through pump 70, it is to be understood that other means, such as a computer controlled valve system, may be used for managing the fluid movement as required.

As discussed earlier, it is possible to conduct accelerated stress testing of dispersions of interest using the methods of this invention without resorting to the use of the SPOS technique. Instead, other techniques of particle size analysis may be used to obtain, or characterize, the PSD of the stressed sample batches. Therefore, in place of SPOS-type particle size analyzer subsystem 80 shown in FIG. 22, one could substitute other types of particle size detectors. Some examples of potentially useful technology that can be employed include those mentioned above: electrical resistive pore, dynamic light scattering, laser diffraction (i.e., Mie scattering and/or Fraunhofer diffraction), ultrasound attenuation, among others. However, it should also be appreciated that it is possible to implement the methods of accelerated stress testing taught in this invention without employing a particle size analyzer per se in the associated apparatus. Examples mentioned earlier include the techniques of turbidity (i.e., attenuation of light through a given path length of a portion of the sample dispersion) and light scattering. In each case, a single numerical quantity or value—referred to herein as "X"—would be produced for a given stressed sample dispersion at a given elapsed time interval, t. There would be no PSD resulting from either of these alternative measurement techniques. Hence, there would also be no PDP value obtained for each sample and elapsed time interval. Instead, there would be available only the primary measured quantity, "X," equal, for example, to the turbidity or light scattering intensity obtained from the stressed sample dispersion.

For either of these two examples of alternative techniques for characterizing sample stability, the value of X will increase monotonically with the extent of particle agglomeration due to stressing of the dispersion, assuming that the instrumentation has been properly designed. The longer the elapsed time for a given level of applied stress, the greater in general will be the measured value of X. Similarly, the greater the level of applied stress for a given length of elapsed time, the greater in general will be the value of X. Hence, as in the case of apparatus based on the use of particle size analysis, there are also quantities derived from the measured quantity, X, that can be used to characterize the stability or quality of the dispersion being tested. These include, but are not limited to, $\partial X/\partial t|_{stress\ level}$ and $\partial X/\partial[stress\ level]|_t$. The apparatus that could be used to implement the methods of this invention using one of these alternative techniques to particle size analysis, resulting in no PSD or PDP values, is shown schematically in FIG. 23.

The particle size analyzer 80 of FIG. 22 is replaced by a sensor 180, which includes a light source 182 projecting a light beam 184 through a flow cell 186. The light beam then strikes a photo sensor 188, which serves as a turbidity detector. An increase in particle agglomeration in the sample dispersion results in a decrease in the intensity of the light beam as it passes through flow cell 186. A decrease of the signal $V_x$ as detected by turbidity detector 188 thus indicates an increase in the agglomeration of particle signifying a lower quality dispersion sample. Signal $V_x$ is fed from turbidity detector 188 through a schematic switch 189 to a signal conditioner 190 to computer controller/processor 100 to generate quality X derived from signal $V_x$.

Figure 23:
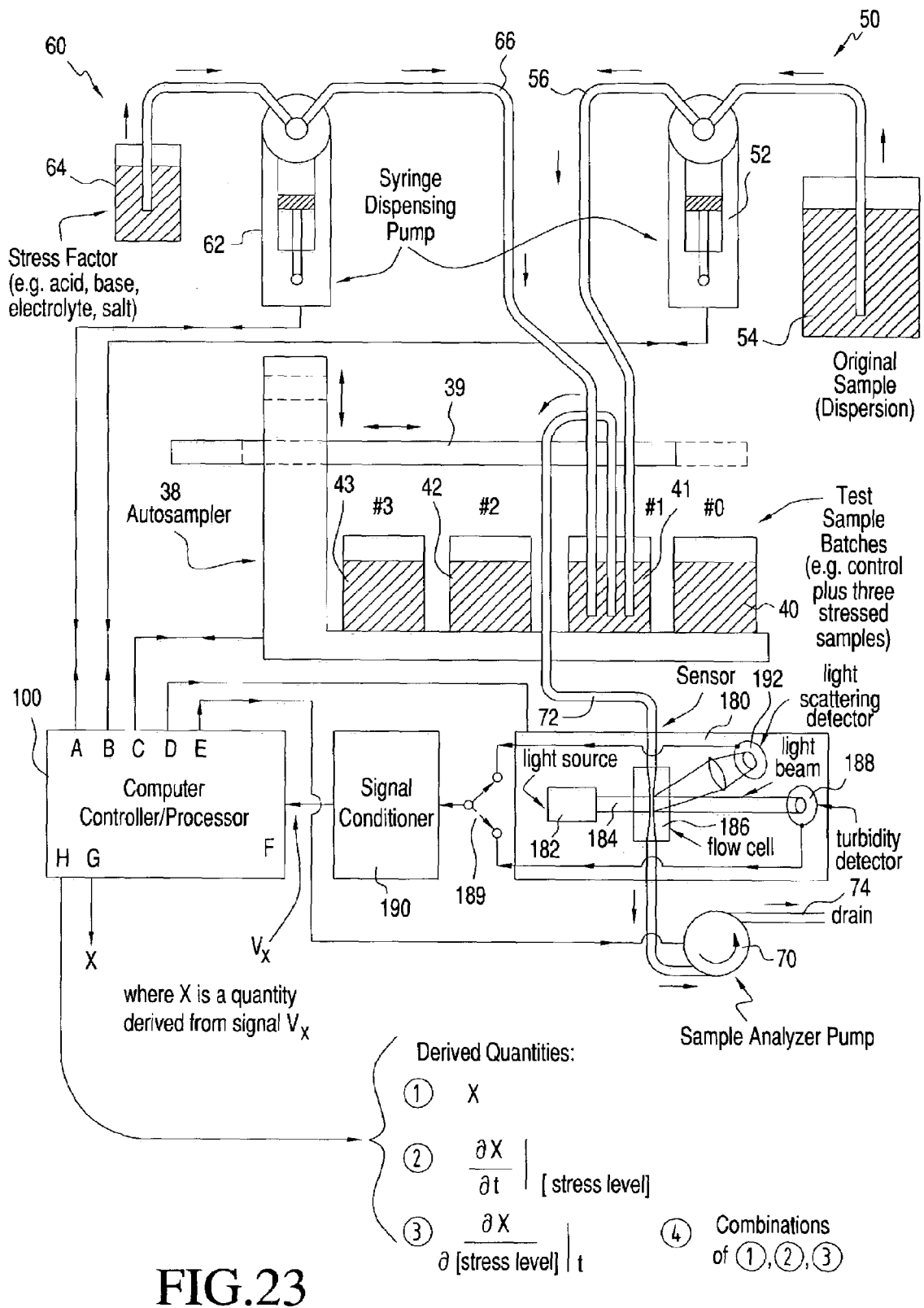
FIG. 23 shows a simplified schematic diagram of a typical apparatus, including a technique other than particle size analysis, such as turbidity or light scattering, that can be used to implement any of the new methods of accelerated determination of the stability of a dispersion or emulsion as described herein.

Alternatively, a light scattering detector 192 receives light scattered from particles in flow cell 186. An increase in the agglomeration of particles results in an increase in scattered light striking photo detector 192 resulting in an increase in a signal $V_x$ generated in detector 192 signifies an increase in agglomeration and a lowering of the quality of the sample dispersion. The signal $V_x$ is fed through switch 189 to signal conditioner 190 and computer controller/processor 100 to provide the quantity X derived from signal $V_x$. The sequence of operations for this alternative apparatus of FIG. 23 is essentially the same as that described for the preferred apparatus (based on SPOS) of FIG. 22, summarized above. Like reference numerals indicated identical parts.

From the descriptions of these embodiments it should be clear that the stability of certain dispersions under investigation may be "multi-dimensional"—i.e., it may be conferred by more than one physical mechanism. In such cases, the most effective stress testing of such a dispersion might call for the simultaneous application of more than one type of stress factor—i.e., through the use of a multi-dimensional stress factor. In effect, one would simultaneously combine two, or even all three, of the embodiments described above. For example, a given dispersion may be stable by virtue of the particles being relatively highly charged and also there being relatively few mobile ions between the particles. In this case, the most effective way to systematically stress it might be to add a particular electrolyte (at one or more concentrations) that decreases both the charge on the particles and the repulsive electrostatic energy, $V_R$, both of which actions result in a reduction of the energy barrier height, $V_{MAX}$. In general, a multi-dimensional stress factor may be specifically engineered by combining two or more of the stress factors utilized singly in the embodiments described herein, applied in various combinations and concentrations/intensities. Again, these include: addition of acid (or base); addition of adsorbing electrolyte; and addition of non-adsorbing salt.

In closing this discussion, it is useful to review the key ideas and salient features of this invention. The application of specific stress factors to a given suspension or emulsion is designed to accelerate the destabilization processes that are inherent in the product, in order to reveal defects that would eventually appear in the final formulation. This invention proposes the use of surrogate measures—i.e., one or more stress factors—in order to predict the stability, and ultimately the performance, of a dispersion throughout its assigned shelf- or use-life. The stress factors are the proximate indicators of the interparticle potential energy barrier height, $V_{MAX}$, of the dispersion, thus providing prognostic information about the stability and quality of the final product. The main purpose of the stress factors is to quantitatively identify the net effect of perturbations of existing interparticle stability, which in charge-stabilized dispersions is governed by the magnitude of $V_{MAX}$. In essence, through the use of a highly sensitive particle sizing technique, coupled with systematic application of one or more stress factors, the methods outlined in this invention permit calibration of the degradation of the underlying stability of the dispersion by systematic titration of $V_{MAX}$. The coupling of an exquisitely sensitive particle sizing capability (LE-SPOS) with the methodical application of one or more stress factors on two different oil-in-water emulsions/dispersions was explained in detail above. These new methods utilize a dependent outcome variable, "PDP," that provides a surrogate measure of $V_{MAX}$. The interpretation of the quantitative effects (both cumulative and differential) of the stress factor on the PDP over time, PDP vs t, is unique and central to the novelty underlying this invention.

This approach is particularly important from three fundamental perspectives with respect to the ability of the methods taught in this invention to detect quantitatively the consequences of changes (i.e., reductions) in $V_{MAX}$. First, it minimizes, or avoids altogether, potentially significant alterations in the physical-chemical structure of the original formulation (i.e., changes in the phase diagram), that would otherwise result from application of excessive levels of various stress factors. Otherwise, a significantly different dispersion or emulsion might be produced, having different physical properties, and therefore its behavior after application of such an excessive stress challenge would be expected to differ from that of the original dispersion. Second, the stability of certain extremely labile dispersions, that would otherwise be intolerant of conventional or even modest amounts of stress, can now be assessed. For example, in some cases, depending on the nature of the components that comprise the dispersion, stability differences between two formulations determined by very small stress-induced perturbations would require precise measurements in order to discriminate between the two levels of stability, based on marginal inherent differences in $V_{MAX}$. Third, such "fine-tuning" of the stress factor response will greatly enhance the overall prognostic capabilities of the method for assessing the overall performance of a dispersion of interest.

The description above teaches methods for assessing the stability of a given dispersion by applying one or more stress factors to multiple batches of the same starting dispersion, where each batch is subjected to a different stress level, or intensity, at the outset (i.e., nominally, t=0). This approach constitutes a form of "parallel processing," in which the effects of different levels of stress are measured using as many sample batches as there are stress levels. This "brute-force" approach is particularly appropriate when a relatively new dispersion—i.e., one that has not been well characterized with respect to stability and/or quality—is being investigated by accelerated stress testing. This approach is effective for establishing an optimal stress "profile" for the dispersion of interest—i.e., for establishing an effective range of stress levels for a given stress factor. This useful first step would typically be applied in a research and development phase, prior to the start of routine manufacturing of the dispersion of interest.

However, once an optimal stress profile has been established for a dispersion of interest, it should be clear that the methods of this invention could be applied with equal effectiveness using a different approach, that of "serial processing." That is, a single batch of the starting sample could be repeatedly (i.e., periodically) stressed at increasing level, in order to achieve the accelerated onset of instability. A given stress factor at a given stress level could be applied to the single sample batch at the outset—i.e., t=0. After a prescribed, appropriate elapsed time, following calculation of the PDP, the same sample batch would then be further stressed using the same stress factor, applied at a higher level. This procedure would be repeated periodically, each time with determination of the PDP. The resulting plot of PDP vs t can be expected to consist of a monotonically increasing ("concave up") curve, in which the detailed behavior of the curve—i.e. $\partial(PDP)/\partial t$ vs t—reveals the underlying stability of the dispersion of interest. The more stable the starting (unstressed) dispersion, the "flatter" (less-curved) the resulting plot of PDP vs t, for a given set of increasing applied stress levels. Comparison of the resulting curve with a reference, or benchmark, curve obtained previously for a sample of known, acceptable stability would permit the quality of the production batch to be monitored and verified. Consequently, the routine commercial or private use of this invention would generally entail its application as part of a standard quality assurance/quality control (QA/QC) protocol, resulting in an evolving database that becomes further refined over time, becoming part of the standard operating procedure for a given dispersion.

The novel methods of this invention are based on the supposition that the response of a given dispersion—i.e., the growth in particle agglomeration over a given size range, $d \geq d_0$, measured by SPOS or another sufficiently sensitive technique—to the application of a given stress factor is a sensitive and reproducible function of the magnitude of the stress level, the elapsed time and the underlying stability of the dispersion. Therefore, independent of theoretical models of colloidal stability (e.g., based on DLVO theory), the relative stability of a given type of dispersion or emulsion can be judged from the behavior of PDP vs t (elapsed time after application of stress) for one or more levels (i.e., magnitudes) of applied stress. This concept can be more easily understood by comparing hypothetical and actual plots of PDP vs t for dispersions that are either more or less stable (i.e., higher or lower quality, respectively) than the particular sample that is being evaluated using the methods of this invention.

Figure 24A:
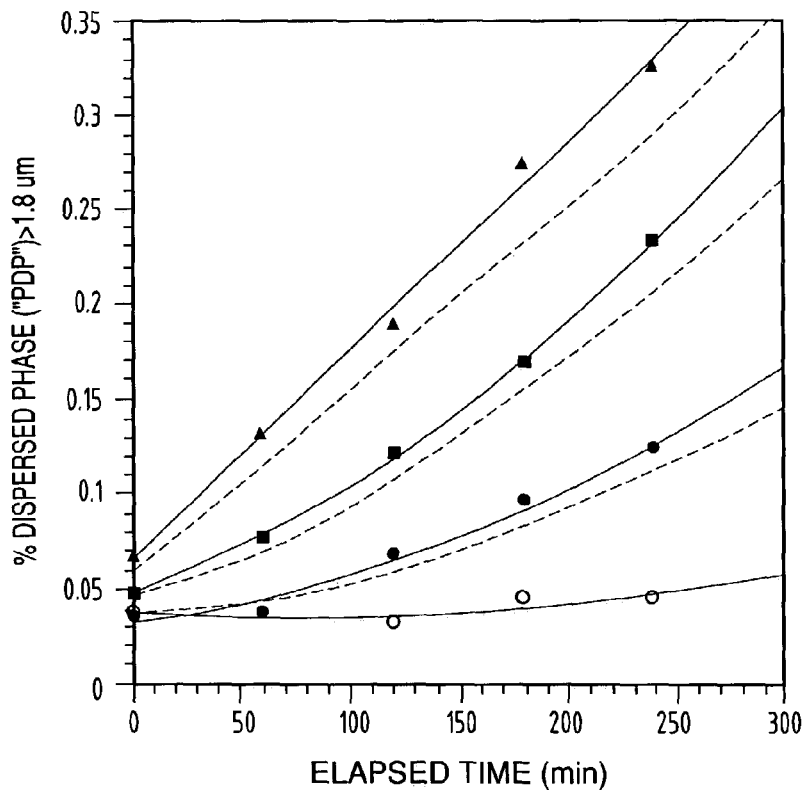
FIG. 24A shows the measured PDP vs t behavior (solid curves, same as FIG. 18) obtained for the vegetable fat emulsion after application of acid stress, plus the hypothetical behavior (dashed curves) that would be obtained for a similar, but moderately more stable, sample.

FIG. 24A contains two sets of plots of PDP vs t, pH. One set of plots (solid curves) represents the actual response obtained from a system—i.e., the vegetable fat emulsion plus destabilizing mixed ionic species (added at t=0) discussed earlier. The other set of plots (dashed curves) indicates a "hypothetical" response from a similar, but more stable, emulsion. The solid curves (and related data points) are identical to the results shown in FIG. 18, representing the response of the emulsion, containing negatively charged droplets, to "acid-stress." Successive lowering of the pH, from 6.56 (control, open circles), to 5.65 (closed circles), 5.13 (closed squares) and 4.46 (closed triangles), gives rise to the time-dependent growth in droplet coalescence shown in both FIGS. 18 and 24A. The dashed curves represent the hypothetical response that might have been obtained for a similar sample, assuming that it was moderately more stable than the emulsion represented by the solid curves. One still observes an increase in PDP with elapsed time for a given stress level (i.e., lower pH value). However, the magnitude of the response—i.e., the extent of droplet coalescence—is lower for any given value of t, given the (presumed) greater stability of the hypothetical sample before the application of stress. The difference in the PDP values obtained for the actual and hypothetical samples, for any given value of t, is expected to grow with increasing stress level, for reasons discussed previously.

Figure 24B:
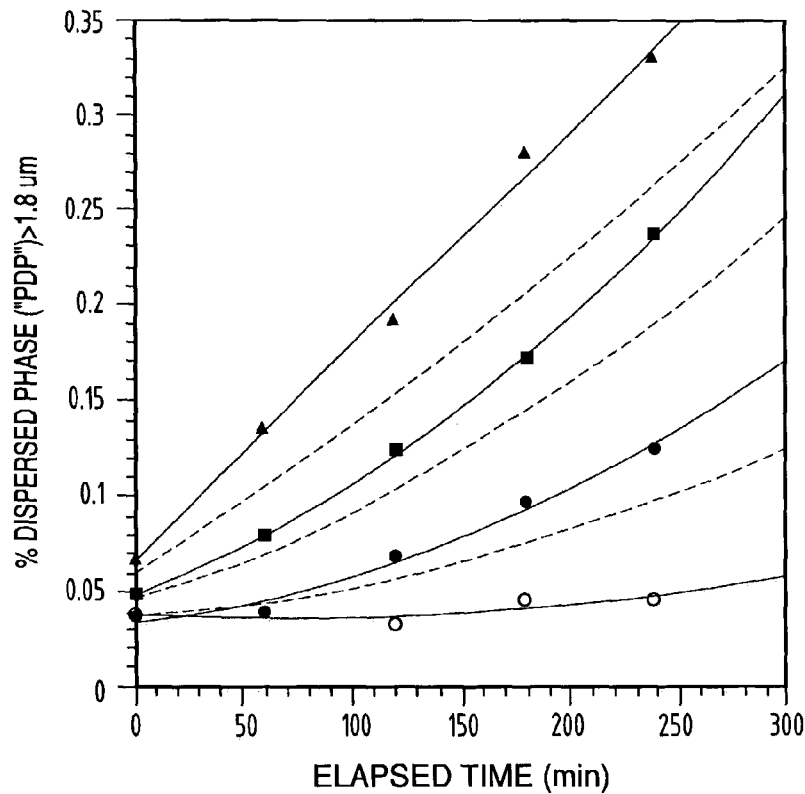
FIG. 24B is the same as FIG. 24A, except the hypothetical PDP vs t behavior (dashed curves) is that which would be obtained for a sample that is significantly more stable than that portrayed in FIG. 24A.
Figure 25A:
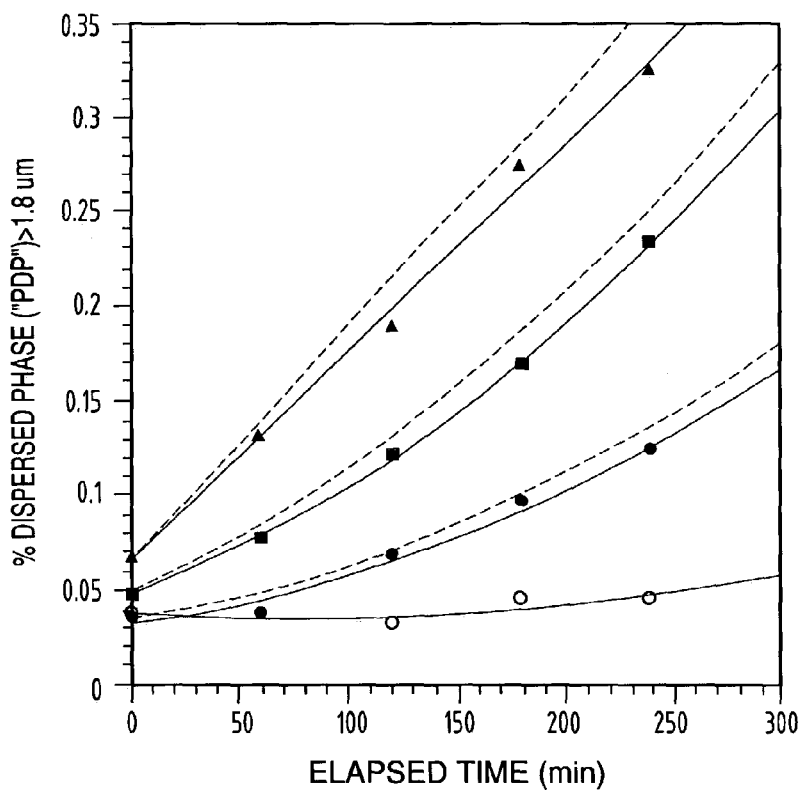
FIG. 25A shows the measured PDP vs t behavior (solid curves, same as FIG. 18) obtained for the vegetable fat emulsion after application of acid stress, plus the hypothetical behavior (dashed curves) that would be obtained for a similar, but moderately less stable, sample.
Figure 25B:
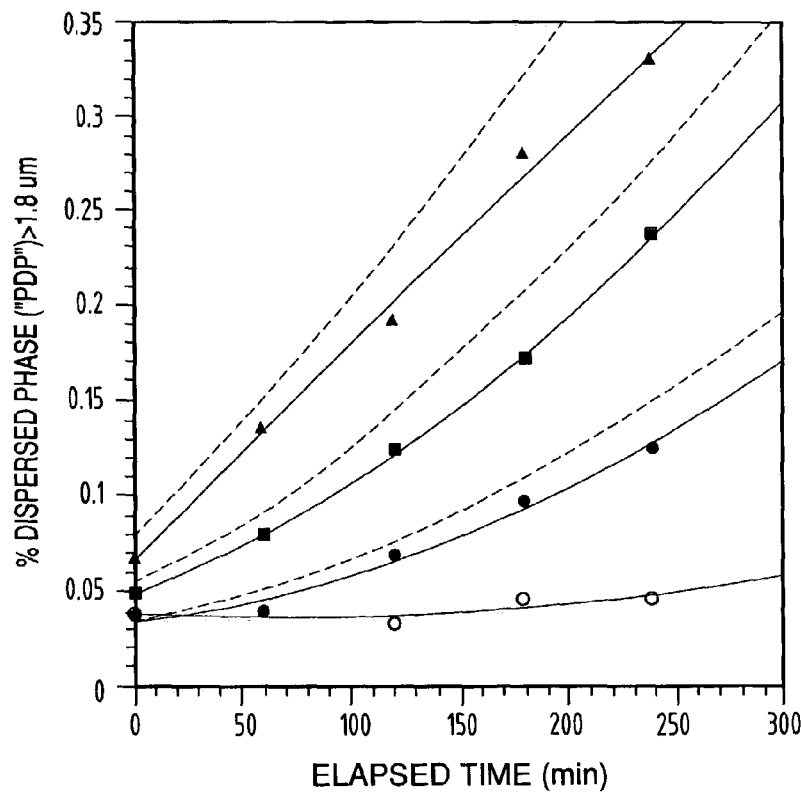
FIG. 25B is the same as FIG. 25A, except the hypothetical PDP vs t behavior (dashed curves) is that which would be obtained for a sample that is significantly less stable than that portrayed in FIG. 25A.

FIG. 24B shows a similar comparison between actual and hypothetical PDP vs t, pH results, assuming that the hypothetical emulsion (dashed curves) is even more stable than the one represented in FIG. 24A. In this case, there is an even larger "suppression" of the hypothetical PDP vs t plots obtained for this second, presumably more stable, hypothetical sample, compared to the plots obtained for the emulsion actually measured (solid curves). Similarly, FIGS. 25A and 25B show comparisons between actual and hypothetical PDP vs t, pH plots for the same kind of emulsion, where the two hypothetical samples (dashed curves) are moderately less stable and considerably less stable, respectively, than the actual sample tested (solid curves, same in all figures).

As an extension of the above concepts regarding the utility of this invention, the observed differences in the way the experimental emulsion responded to certain stress factors is worthy of further comment. The studies of the vegetable fat emulsion again serve to illustrate one way of applying the methods of the current invention, as there are several independent factors, such as time, stress factor and stress level that greatly influence the main dependent variable, "PDP." Specifically, an illustrative example of the effects of time-dependent stress factor on the PDP is helpful. To review, FIG. 16 shows the behavior of PDP vs t over 28 hours for the vegetable fat emulsion, that was "pushed" toward instability by the addition of low concentrations of mixed ionic species. Clear evidence of instability did not appear until approximately 24 hours had elapsed. With this result in mind, the same emulsion was systematically challenged by two different stress factors in an effort to accelerate the manifestation of instability (i.e., a significant increase in PDP) to a much shorter elapsed time. Consequently, studies were carried out using two different stress factors of various levels, or "intensities," designed to elicit significant measurable effects of instability in just one-fourth the normal required time—i.e., only (approximately) 240 minutes or less.

For example, the vegetable fat emulsion (plus destabilizing mixed ionic species) was subjected to acid (i.e., reduced pH) stress, with the results shown in FIG. 18 and Table IV. The measured response of the emulsion, the PDP, was found to increase approximately linearly with elapsed time, t, for each level of applied stress, or pH value. As the pH decreased, an increasingly positive correlation of the PDP with t was observed, with the correlation coefficient, r, increasing from 0.972 for pH=5.65 ($\Delta$pH=−0.91) to 0.996 for pH=4.46 ($\Delta$pH=−2.1). These high values confirm the strong correlation that exists between the measured PDP values and the elapsed time after application of pH stress.

These findings are consistent with concentration-dependent, specific adsorption of hydrogen ions ($H^+$) to the droplet surfaces, causing a progressive reduction in the interparticle repulsive potential energy, $V_R$, and height of the resulting energy barrier, $V_{MAX}$, resulting in accelerated coalescence. Clearly, the higher the level of acid stress, the better the correlation of the increased PDP values with different elapsed times. In order to design the most effective stress test(s) for this emulsion, a series of additional studies would be warranted, focusing on a smaller range of pH values that yield the highest r-values. In the preliminary study (Table IV), the highest r-values (0.99) were obtained for the pH values of 5.13 and 4.46. Therefore, the next set of experiments might be designed around these pH values. As there were immediate changes at time t=0 for pH=5.13, incremental increases in pH above 5.13, such as 5.48 and 5.31, would establish the threshold level below which immediate changes are not induced in the PDP. Similarly, incremental increases in pH above 4.46, such as 4.69 and 4.91, could be used to show the progressive effects at time t=0 of decreasing the pH from 5.13 to 4.46. These and additional experiments would be conducted to optimize the stress level(s) for a given emulsion. Hence, the purpose of using $\Delta$PDP correlations under various experimental conditions is to identity a meaningful range of stress factor(s) and concentrations that best characterize the stability of a given emulsion or dispersion.

Finally, these illustrations have focused on liquid dispersions, but it must be emphasized that the methods taught in this invention may be usefully applied to true solutions. That is, certain stress factors may also be applied on solutions, in order to induce precipitation of either active or inactive components contained therein, ultimately leading to adverse alterations in the use or application of the solution. The appearance or growth of particles in a solution from either baseline or historical levels for a given product would imply inferiority compared to products devoid of such particulate matter. Thus, for true solutions, precipitation would be the main outcome that can be induced by mild perturbations of stress in inferior products. Again, analysis techniques that are sufficiently sensitive to changes in the PSD (e.g., particle size growth associated with precipitation) can be combined with the application of appropriate stress factors/levels to solutions of interest. Such an approach permits accelerated stress testing of solution-based products, allowing inferior products to be distinguished from superior ones.

The endpoint of the accelerated stress study predictions described herein is contingent upon the nature of the individual product being analyzed and its applications, together with what are considered to be acceptable stability criteria. For example, in the case of a very costly (i.e., valuable) product, for which a decision to accept or reject a manufactured batch based on accelerated stress testing has great economic consequences, application of this invention should be based on highly specific endpoints that minimize the number of false positives. That is, the specificity of the test(s) should be as close to 100% as possible, recognizing that there will be a higher tolerance for false negatives. Conversely, in the case of a product that has major health consequences, the outcome of applying a stress factor to a given dispersion or emulsion should be based on highly sensitive endpoints(s) that minimize the number of false negatives. That is, the sensitivity of the test(s) should be as close to 100% as possible, recognizing that there will necessarily be a higher tolerance for false positives, because the outcome may be a matter of life or death. Clearly, sensitivity bears an inverse relationship to specificity—i.e., as sensitivity increases, specificity decreases, and vice-versa. The usual technique that relates sensitivity and specificity is known as the receiver/operating characteristic. In other cases, where the costs or consequences of applying these methods are not critical, and neither the end product nor the test requires such rigorous specifications, a cost-effective balance between the types of tests employed, and their sensitivity and specificity, can be reached. Clearly, the manufacturer will make such determinations on an individual basis. Whenever possible, more than one stress factor and/or condition for each product should be applied when making these critical decisions. Ultimately, the cumulative data/experience over time with a given product will determine the optimal application of the methods taught in this invention.

The present invention is intended to be used for evaluating the quality of dispersions and emulsions, where the response obtained by selective particle size analysis is highly sensitive and/or specific in identifying inferior products, ideally prior to their use or administration. The procedures taught in this invention have been portrayed as "performance assessment" methods, to be employed at the end of a production cycle, prior to packaging, as well as for testing a certain number of final packaged units prior to commercial distribution. Although the invention has been described above in terms of accelerated stability testing, this emphasis is merely illustrative and is not meant to be limiting in any way. Those skilled in the field of dispersion technology will determine other appropriate modifications of the invention. For example, use of the methods taught in this invention to optimize the production of large-scale commercial dispersion manufacturing and processing procedures, so as to minimize end-batch failures and/or commercial product losses, would be expected. Therefore, these methods can also be applied to products at pre-defined "in-process" points during their manufacture. There are a variety of ways the data generated by these studies may be applied to specific manufacturing or commercial operations. It would be desirable to apply this invention in a manner that improves the quality of the manufactured product, such as constructing certain product specifications to determine "pass" or "fail" conditions of performance. These may be applied at varying times during the manufacture, distribution and/or application of a product during its life-use cycle.

Critical "moments" in the manufacturing of dispersions or emulsions on any scale can occur at key processing intervals. These moments are frequently related to different mixing or application steps; the physicochemical conditions are specific to the composition, processing or final use of the dispersion, or emulsion, as well as to the individual manufacturer. The critical moments may also differ even when the dispersion is produced by the same manufacturer, but made at different production sites. Thus, application of the methods taught in this invention will permit optimization of many aspects of the manufactured product throughout its production and life-use cycle. The industrial or private manufacturer of a commercial or specially-prepared dispersion or emulsion may not only improve its final quality or safety profile, but also extend the shelf-life customarily assigned to currently available products, further decreasing the potential for economic loss or waste. The application of the methods introduced herein may also improve the physicochemical tolerance of the product to stresses that may occur during the transport, storage and final use condition to which it will be exposed or applied by the end-user. These include high-risk events that can occur during the handling of the product at any level until use. Ultimately, the methods described herein will be uniquely applied in ways that, in many cases, are proprietary in nature. For example, these may depend on (but are not limited to), the following general conditions: composition of the dispersion or emulsion; types of stress factors applied; means of achieving the desired dispersion or emulsion (e.g., mechanical stirring, milling, homogenization, polymerization, etc.); sequences of mixing; experience of production personnel; and physical conditions of manufacturing, transportation and end-user environments. Thus, the methods and embodiments described herein can be applied at a variety of stages in the development and distribution of dispersions and emulsions in an effort to routinely produce high quality and safe consumable products.

While the invention has been particularly shown and described with reference to preferred embodiments thereof, it will be understood by those skilled in the art that the foregoing and other changes in form and detail may be made therein without departing from the spirit and scope of the invention.

TABLE I

Regression Analysis of PDP vs t, pH Data Obtained for an Acid-Stressed Dairy Fat (Whole Milk) Emulsion (FIGS. 5–7)

| Time (min) | PDP (Control) | PDP (pH = 6.1) | PDP (pH = 5.7) |
|---|---|---|---|
| | Batch #1 (0608) | | |
| 0 | 0.876 | 0.782 | 0.780 |
| 80 | 0.863 | 0.749 | 0.863 |
| 160 | 0.903 | 0.773 | 0.767 |
| 240 | 0.811 | 0.745 | 0.813 |

TABLE I-continued

Regression Analysis of PDP vs t, pH Data Obtained for an
Acid-Stressed Dairy Fat (Whole Milk) Emulsion (FIGS. 5–7)

| Time (min) | PDP (Control) | PDP (pH = 6.1) | PDP (pH = 5.7) |
|---|---|---|---|
| Correlation coefficient (r) | −0.520 | −0.630 | 0.005 |
| Slope (PDP vs t) | −0.00018 | −0.00011 | 0.000002 |
| PDP-intercept (t = 0) | 0.887 | 0.775 | 0.806 |
| Batch #2 (0612) | | | |
| 0 | 0.906 | 0.768 | 0.753 |
| 80 | 0.850 | 0.885 | 1.002 |
| 160 | 0.830 | 1.070 | 1.200 |
| 240 | 0.835 | 1.261 | 1.390 |
| Correlation coefficient (r) | −0.865 | 0.995 | 0.997 |
| Slope (PDP vs t) | −0.00029 | 0.00204 | 0.00260 |
| PDP-intercept (t = 0) | 0.890 | 0.747 | 0.771 |
| Batch #3 (0615) | | | |
| 0 | 1.072 | 0.823 | 0.899 |
| 80 | 1.018 | 0.860 | 0.851 |
| 160 | 1.016 | 0.789 | 0.781 |
| 240 | 1.122 | 0.831 | 0.892 |
| Correlation coefficient (r) | 0.054 | −0.210 | −0.230 |
| Slope (PDP vs t) | 0.00005 | −0.00006 | −0.00012 |
| PDP-intercept (t = 0) | 1.0213 | 0.833 | 0.870 |

TABLE II

Regression Analysis of PDP vs t, [CaCl$_2$] Data Obtained for a
Calcium Chloride-Stressed Dairy Fat (Whole Milk) Emulsion
(FIGS. 10–13)

| Time (min) | PDP (Control) | PDP (0.005 M CaCl$_2$) | PDP (0.01 M CaCl$_2$) |
|---|---|---|---|
| Batch #1 (0608) | | | |
| 0 | 0.927 | 0.826 | 0.843 |
| 80 | 0.848 | 0.844 | 1.035 |
| 160 | 0.902 | 0.890 | 1.096 |
| 240 | 0.897 | 0.880 | 1.276 |
| 660 | 0.852 | 0.819 | 1.385 |
| 1440 | 0.854 | 0.840 | 1.565 |
| Correlation coefficient (r) | −0.566 | −0.253 | 0.897 |
| Slope (PDP vs t) | −0.00003 | −0.00001 | 0.00043 |
| PDP-intercept (t = 0) | 0.895 | 0.856 | 1.013 |
| Batch #2 (0612) | | | |
| 0 | 0.956 | 0.952 | 1.217 |
| 80 | 0.874 | 1.075 | 1.313 |
| 160 | 0.945 | 1.040 | 1.374 |
| 240 | 0.988 | 1.105 | 1.409 |
| 660 | 0.967 | 1.241 | 1.611 |
| 1440 | 1.078 | 1.324 | 6.815 |
| Correlation coefficient (r) | 0.838 | 0.927 | 0.934 |
| Slope (PDP vs t) | 0.00010 | 0.00023 | 0.00038 |
| PDP-intercept (t = 0) | 0.924 | 1.023 | 0.6516 |
| Batch #3 (0615) | | | |
| 0 | 1.033 | 1.000 | 0.992 |
| 80 | 0.985 | 1.019 | 1.073 |
| 160 | 1.027 | 1.050 | 1.121 |
| 240 | 1.026 | 1.050 | 1.138 |
| 660 | 1.044 | 1.037 | 1.088 |
| 1440 | 0.955 | 1.012 | 1.163 |
| Correlation coefficient (r) | −0.613 | −0.157 | 0.639 |
| Slope (PDP vs t) | −0.00004 | −0.000006 | 0.00007 |
| PDP-intercept (t = 0) | 1.028 | 1.031 | 1.065 |

TABLE III

Regression Analysis of PDP vs t, [salt] Data Obtained for a
Sodium Chloride-Stressed Oil-in-Water Vegetable Fat Emulsion
(FIG. 17)

| Time (min) | PDP (Control) | PDP (0.05 M NaCl) | PDP (0.10 M NaCl) | PDP (0.15 M NaCl) |
|---|---|---|---|---|
| 0 | 0.053 | 0.087 | 0.089 | 0.172 |
| 60 | 0.048 | 0.103 | 0.122 | 0.218 |
| 120 | 0.048 | 0.145 | 0.222 | 0.308 |
| 180 | 0.063 | 0.226 | 0.351 | 0.528 |
| 240 | 0.080 | 0.310 | 0.469 | 0.641 |
| Correlation coefficient (r) | 0.779 | 0.958 | 0.980 | 0.973 |
| Slope (PDP vs t) | 0.000098 | 0.00085 | 0.00152 | 0.00195 |
| PDP-intercept (t = 0) | 0.0444 | 0.0582 | 0.0510 | 0.1220 |

TABLE IV

Regression Analysis of PDP vs t, pH Data Obtained for an
Acid-Stressed Oil-in-Water Vegetable Fat Emulsion (FIG. 18)

| Time (min) | PDP (Control) | PDP (pH = 5.65) | PDP (pH = 5.13) | PDP (pH = 4.46) |
|---|---|---|---|---|
| 0 | 0.038 | 0.036 | 0.049 | 0.067 |
| 60 | 0.039 | 0.038 | 0.079 | 0.136 |
| 120 | 0.032 | 0.068 | 0.124 | 0.192 |
| 180 | 0.045 | 0.098 | 0.172 | 0.281 |
| 240 | 0.047 | 0.126 | 0.238 | 0.331 |
| Correlation coefficient (r) | 0.609 | 0.972 | 0.987 | 0.996 |
| Slope (PDP vs t) | 0.00003 | 0.00037 | 0.00072 | 0.00099 |
| PDP-intercept (t = 0) | 0.0353 | 0.0246 | 0.0405 | 0.0607 |

We claim:

1. A method for determining a measure of the stability of a sample comprising a dispersion of solid or liquid droplet particles suspended in a liquid carrier, wherein an interparticle potential energy barrier inhibits neighboring particles from approaching each other closely enough to permit irreversible agglomeration due to strong, short-range attractive forces, said method comprising:
    applying a stress factor to said sample to reduce a height of said interparticle potential energy barrier so as to accelerate particle agglomeration;
    computing a rate of change of a percentage of dispersed phase (PDP) associated with relatively large particles representing particle agglomerates with elapsed time for an applied level of stress factor; and
    detecting an increase in rate of said particle agglomeration as a measure of the stability.

2. The method of claim 1, wherein said step of detecting the increase in rate of said particle agglomeration comprises the use of a high sensitivity detector.

3. The method of claim 2, wherein said high sensitivity detector is a single-particle sensor.

4. The method of claim 3, wherein said detector is a single-particle optical sensor (SPOS).

5. The method of claim 2, wherein said high sensitivity detector comprises a detector sensing a value X responsive to said particles passing through a given region for a given time interval.

6. The method of claim 5, wherein said value X is a measure of the attenuation of light in response to the turbidity of said sample dispersion.

7. The method of claim 5, wherein said value X is a measure of the intensity of light scattered over a given range of angles from said particles of said sample dispersion.

8. The method of claim 1, wherein said step of detecting the increase in rate of said particle agglomeration comprises using sensitive, quantitative means for determining the extent to which said sample has become less stable by virtue of said application of said stress factor.

9. The method of claim 8, wherein said sensitive, quantitative means produces a particle size distribution (PSD) showing the concentration of particles as a function of size over a range of normal particle sizes and a tail of large-diameter outlier particles larger than said normal particle sizes and indicative of particle agglomerates.

10. The method of claim 1, wherein said stress factor reduces a surface charge on said particles by changing the pH of said sample.

11. The method of claim 10, wherein said particles have a net negative charge, and wherein said stress factor is an acid or buffered acid added to said sample to reduce the pH of said sample, thereby reducing the net negative charge on the particles.

12. The method of claim 10, wherein said particles have a net positive charge, and wherein said stress factor is a base or buffered base added to said sample to raise the pH of said sample, thereby reducing the net positive charge on the particles.

13. The method of claim 1, wherein said stress factor is an absorbing electrolyte added to said sample allowing dissociated ions of appropriate charge to be adsorbed to oppositely charged surfaces of said particles to reduce a net charge on said particles.

14. The method of claim 13, wherein said particles have a net negative charge and said ions dissociated from adsorbing electrolyte include positively charged ions that bind to the surfaces of said particles and reduce the net charge on said particles and thereby reduce said height of said interparticle potential energy barrier.

15. The method of claim 13, wherein said particles have a net postive charge and said ions dissociated from adsorbing electrolyte include negatively charged ions that bind to the surfaces of said particles and reduce the net charge on said particles and thereby reduce said height of said interparticle potential energy barrier.

16. The method of claim 1, wherein said stress factor is a salt added to said sample, giving rise to dissociated, mobile ions that partially screen electrostatic repulsions between charged particles, thus promoting their agglomeration.

17. The method of claim 16, wherein said stress factor is applied as a simple monovalent salt.

18. The method of claim 17, wherein said monovalent salt is sodium chloride.

19. The method of claim 1, wherein said stress factor is applied in successive increments at spaced time intervals resulting in successively higher stress levels in said sample being stressed and said step of detecting the increase in rate of said particle agglomeration is repeated after each stress factor increment.

20. The method of claim 1, wherein said sample is divided into two or more batches, wherein said step of applying said stress factor to said sample comprises applying different levels of said stress factor to each batch, and wherein said step of detecting the increase in rate of said particle agglomeration in each batch is performed after the passage of one or more time intervals Δt.

21. The method of claim 20, further providing a control batch of said sample, applying no stress factor to said control batch, and detecting the increase in particle agglomeration in said control batch after the passage of said time interval Δt.

22. The method of claim 20, wherein immediately after said application of said stress factor, there is a step of detecting the extent of particle agglomeration in each of said batches.

23. The method of claim 20, wherein said step of detecting the increase in rate of said particle agglomeration further comprises measuring a particle size distribution (PSD) of each batch over an appropriate range of particle sizes and calculating a percentage of the dispersed phase (PDP) describing the fraction of the total particle volume or mass contained in the tail of large-diameter outlier particles representing particle agglomerates from each measured PSD.

24. The method of claim 23, further comprising computing the increase in said PDP per unit change in said stress factor level for a given value of elapsed time.

25. The method of claim 24, wherein a figure of merit (FM) is derived from said increase in said PDP per unit change in said stress factor level for a given value of elapsed time, said elapsed time being sufficiently long to permit a measurable acceleration in instability and resulting detectable increase in particle agglomeration to be established, whereby the larger the value of a FM for a given value of elapsed time and level of applied stress factor, the less stable is said sample.

26. The method of claim 20, wherein said stress factor reduces a surface charge on said particles by changing the pH of said batches.

27. The method of claim 26, wherein said particles have a net negative charge, and wherein said stress factors are acid or buffered acid added in different concentrations to said batches to reduce the pH of said batches of said sample by different amounts, thereby decreasing the net negative charge on the particles in said batches by different amounts.

28. The method of claim 26, wherein said particles have a net positive charge, and wherein said stress factors are base or buffered base added in different concentrations to said batches to raise the pH of said batches of said sample by different amounts, thereby decreasing the net positive charge on the particles in said batches by different amounts.

29. The method of claim 20, wherein said stress factor is adsorbing electrolyte added to said batches of said sample allowing dissociated ions of appropriate charge to be adsorbed to oppositely-charged surfaces of said particles to reduce a net charge on said particles.

30. The method of claim 29, wherein said particles have a net negative charge, and said ions dissociated from said adsorbing electrolyte include positively-charged ions that bind to the surfaces of said particles and reduce the net charge on said particles and thereby reducing said height of said interparticle potential energy barrier.

31. The method of claim 29, wherein said particles have a net positive charge, and said ions dissociated from said adsorbing electrolyte include negatively charged ions that bind to the surfaces of said particles and reduce the net charge on said particles and thereby reducing said height of said interparticle potential energy barrier.

32. The method of claim 20, wherein said stress factor is salt added to said sample, giving rise to dissociated, mobile ions that partially screen electrostatic repulsions between charged particles, thus promoting their agglomeration.

33. The method of claim 32, wherein said stress factor is applied as a simple monovalent salt.

34. The method of claim 33, wherein monovalent salt is sodium chloride.

35. The method of claim 20, wherein said steps of detecting the increase in rate of said particle agglomeration in each batch are performed serially using a common detector, and wherein said passage of time Δt is different for each batch.

36. The method of claim 20, wherein said steps of detecting the increase in rate of said particle agglomeration in each batch are performed in parallel using separate detectors.

37. The method of claim 36, wherein said passage of time Δt is the same for each batch.

38. The method of claim 1, wherein a figure of merit (FM) for said sample is derived from said rate of change of said PDP with elapsed time for a given stress factor level, whereby stable dispersions or emulsions will have relatively small values of FM, corresponding to relatively small rates of change of said PDP with elapsed time, and inferior, less stable, dispersions or emulsions will have relatively large values of FM, corresponding to relatively large rates of change of said PDP with elapsed time.

39. The method of claim 1, further comprising computing the increase in said PDP per unit change in said stress factor level for a given value of elapsed time.

40. The method of claim 39, wherein a figure of merit (FM) is derived from said rate of increase of said PDP with elapsed time for each stress factor level combined with said increase in said PDP per unit change in said stress factor level for a given value of elapsed time.

41. A method for determining the stability of a sample comprising a dispersion of solid or liquid droplet particles suspended in a liquid carrier, wherein an interparticle potential energy barrier inhibits neighboring particles from approaching each other closely enough to permit irreversible agglomeration due to strong, short-range attractive forces, said method comprising the steps of:
 applying a stress factor to said sample to reduce a height of said interparticle potential energy barrier so as to accelerate agglomeration of said particles;
 detecting an increase in rate of said agglomeration using sensitive, quantitative means for determining the extent to which said sample has become less stable by producing a particle size distribution (PSD) showing the concentration of particles as a function of size over a range of normal particle sizes and a tail of relatively large-diameter outlier particles larger than said normal particle sizes indicative of particle agglomerates;
 calculating a percentage of the dispersed phase (PDP) associated with said tail of large-diameter outlier particles from said measured PSD; and
 computing a rate of change of said PDP with elapsed time.

42. The method of claim 41, wherein a figure of merit (FM) for said sample is derived from said rate of change of said PDP with elapsed time for a given stress factor level, whereby stable dispersions or emulsions will have relatively small values of FM, corresponding to relatively small rates of change of said PDP with elapsed time, and inferior, less stable, dispersions or emulsions will have relatively large values of FM, corresponding to relatively large rates of change of said PDP with elapsed time.

43. A method for determining the stability of a sample comprising a dispersion of solid or liquid droplet particles suspended in a liquid carrier, wherein an interparticle potential energy barrier inhibits neighboring particles from approaching each other closely enough to permit irreversible agglomeration due to strong, short-range attractive forces, said method comprising the steps of:
 applying a stress factor to said sample to reduce a height of said interparticle potential energy barrier so as to accelerate agglomeration of said particles;
 detecting an increase in rate of said agglomeration using sensitive, quantitative means for determining the extent to which said sample has become less stable by producing a particle size distribution (PSD) showing the concentration of particles as a function of size over a range of normal particle sizes and a tail of large-diameter outlier particles larger than said normal particle sizes indicative of the increase in particle agglomerates;
 calculating a percentage of the dispersed phase (PDP) associated with said tail of large-diameter outlier particles from said measured PSD; and
 computing the increase in said PDP per unit change in said applied stress factor for a given value of elapsed time.

44. The method of claim 43, wherein a figure of merit (FM) is derived from said increase in said PDP per unit change in said stress factor level for a given value of elapsed time, said elapsed time being sufficiently long to permit a measurable acceleration in instability and detectable increase in particle agglomeration to be established, whereby the larger the value of FM for a given value of elapsed time and level of applied stress factor, corresponding to a larger increase in said PDP per unit change in said stress factor level, the less stable is said sample.

45. The method of claim 43, further comprising computing a rate of change of said PDP with elapsed time.

46. The method of claim 45, wherein a figure of merit (FM) is derived from said rate of change of said PDP with elapsed time for each stress factor level combined with said increase in said PDP per unit change in said stress factor level for a given value of elapsed time.

47. An apparatus for determining the stability of a sample comprising a dispersion of solid or liquid droplet particles suspended in a liquid carrier, wherein an interparticle potential energy barrier inhibits neighboring particles from approaching each other closely enough to permit irreversible agglomeration due to strong, short-range attractive forces, said apparatus comprising:
 means supplying said sample to a test container;
 means applying a stress factor to said sample in said container to reduce a height of said interparticle potential energy barrier so as to accelerate particle agglomeration;
 means for computing a rate of change of a percentage of dispersed phase (PDP) associated with relatively large particles representing particle agglomerates with elapsed time for a given applied level of stress factor; and
 means for detecting an increase in rate of said particle agglomeration as a measure of the stability.

48. The apparatus of claim 47, wherein said means for detecting an increase in rate of said particle agglomeration comprises a high sensitivity detector.

49. The apparatus of claim 48, wherein said high sensitivity detector is a single particle sensor.

50. The apparatus of claim 49, wherein said detector is a single particle optical sensor (SPOS).

51. The apparatus of claim 48, wherein said high sensitivity detector comprises a detector sensing a value X responsive to said particles passing through a given region for a given time interval.

52. The apparatus of claim 51, wherein said value X is a measure of the attenuation of light in response to the turbidity of said sample dispersion.

53. The apparatus of claim 51, wherein said value X is a measure of the intensity of light scattered over a given range of angles from said particles of said sample dispersion.

54. The apparatus of claim 47, wherein said means for detecting an increase in rate of said particle agglomeration comprises sensitive, quantitative means for determining the extent to which said sample has become less stable by virtue of said application of said stress factor.

55. The apparatus of claim 54, wherein said sensitive, quantitative means produces a particle size distribution (PSD) showing the concentration of particles as a function of size over a range of normal particle sizes and a tail of relatively large-diameter outlier particles larger than said normal particle sizes and indicative of particle agglomerates.

56. The apparatus of claim 54, wherein said means for detecting an increase in rate of said particle agglomeration comprises a detector sensing a value X responsive to said particles passing through a given region for a given time interval.

57. The apparatus of claim 56, wherein said value X is a measure of the attenuation of light in response to the turbidity of said sample dispersion.

58. The apparatus of claim 56, wherein said value X is a measure of the intensity of light scattered over a given range of angles from said particles of said sample dispersion.

59. The apparatus of claim 47, wherein said stress factor reduces a surface charge on said particles by changing the pH of said sample.

60. The apparatus of claim 59, wherein said particles have a net negative charge, and wherein said stress factor is an acid or buffered acid added to said sample to reduce the pH of said sample, thereby reducing the net negative charge on the particles.

61. The apparatus of claim 59, wherein said particles have a net positive charge, and wherein said stress factor is a base or buffered base added to said sample to raise the pH of said sample, thereby reducing the net positive charge on the particles.

62. The apparatus of claim 47, wherein said stress factor is adsorbing electrolyte added to said sample allowing dissociated ions of appropriate charge to be absorbed to oppositely charged surfaces of said particles to reduce a net charge on said particles.

63. The apparatus of claim 62, wherein said particles have a net negative charge and said ions dissociated from said adsorbing electrolyte include positively charged ions that bind to the surfaces of said particles and reduce the net charge on said particles and thereby reduce the height of said interparticle potential energy barrier.

64. The apparatus of claim 62, wherein said particles have a net positive charge and said ions dissociated from said adsorbing electrolyte include negatively charged ions that bind to the surfaces of said particles and reduce the net charge on said particles and thereby reduce the height of said interparticle potential energy barrier.

65. The apparatus of claim 47, wherein said stress factor is salt added to said sample, giving rise to dissociated, mobile ions that partially screen electrostatic repulsions between charged particles, thus promoting their agglomeration.

66. The apparatus of claim 65, wherein said stress factor is applied as a simple monovalent salt.

67. The apparatus of claim 65, wherein said stress factor is applied as a divalent or trivalent salt.

68. The apparatus of claim 47, wherein said means applying a stress factor to said sample in said container is applied in successive increments at spaced time intervals, and wherein said means for detecting an increase in rate of said particle agglomeration measures the increase in said particle agglomeration after each application of said stress factor increment.

69. The apparatus of claim 47 further comprising a plurality of said test containers, wherein said means for supplying said sample supplies said sample as separate batches in said plurality of test containers, and wherein said means applying a stress factor applies different levels of said stress factor to each of said batches in said test containers, and wherein said means for detecting an increase in rate of said particle agglomeration detects the increase in said particle agglomeration after the passage of one or more time intervals $\Delta t$.

70. The apparatus of claim 69, further comprising an additional test container, said means for supplying said sample supplies a control batch to said additional test container, said means for applying a stress factor applies no stress factor to said control batch in said additional test container, and said means for detecting an increase in rate of said particle agglomeration measures the increase in particle agglomeration in said control batch after the passage of one or more of said time intervals $\Delta t$.

71. The apparatus of claim 69, wherein said means for detecting an increase in rate of said particle agglomeration further detects the extent of particle agglomeration in each of said batches immediately after said application of said stress factor to each of said batches.

72. The apparatus of claim 47, wherein said means for detecting an increase in rate of said particle agglomeration comprises sensitive, quantitative means producing a particle size distribution (PSD) showing the concentration of particles as a function of size over a range of normal particle sizes and a tail of relatively large diameter outlier particles larger than said normal particle sizes indicative of the particle agglomerates; and wherein said apparatus further comprises means calculating a percentage of the dispersed phase (PDP) from said measured PSD.

73. The apparatus of claim 72, wherein said apparatus further comprises means for computing the increase in said PDP per unit change in said stress factor level for a given value of elapsed time.

74. The apparatus of claim 73, wherein said apparatus further comprises means for deriving a figure of merit (FM) from said increase in said PDP per unit change in said stress factor level for a given value of elapsed time, said elapsed time being sufficiently long to permit a measurable acceleration in instability and detectable increase in particle agglomeration to be established, whereby the larger the value of FM for a given value of elapsed time and level of applied stress factor, the less stable is said sample.

75. The apparatus of claim 47, wherein said apparatus further comprises means for deriving a figure of merit (FM) from said rate of change of said PDP with elapsed time for a given stress factor level, whereby stable dispersions or emulsions will have relatively small values of FM, corresponding to relatively small rates of change of said PDP with elapsed time, and inferior, less stable, dispersions or emulsions will have relatively large values of FM, corresponding to relatively large rates of chance of said PDP with elapsed time.

76. The apparatus of claim 47, further comprising means for computing the increase in said PDP per unit change in said stress level for a given value of elapsed time.

77. The apparatus of claim 76, further comprising means for deriving a figure of merit (FM) from said rate of change of said PDP with elapsed time for each stress factor level combined with said increase in said PDP per unit change in said stress factor level for a given value of elapsed time.

* * * * *